(12) United States Patent
Moore et al.

(10) Patent No.: US 9,932,400 B2
(45) Date of Patent: Apr. 3, 2018

(54) BI-SPECIFIC MONOVALENT DIABODIES THAT ARE CAPABLE OF BINDING TO GPA33 AND CD3, AND USES THEREOF

(71) Applicant: MacroGenics, Inc., Rockville, MD (US)

(72) Inventors: Paul A. Moore, Bethesda, MD (US); Jonathan Li, Millbrae, CA (US); Francine Zhifen Chen, San Francisco, CA (US); Leslie S. Johnson, Damestown, MD (US); Kalpana Shah, Boyds, MD (US); Ezio Bonvini, Potomac, MD (US)

(73) Assignee: MacroGenics, Inc., Rockville, MD (US)

( * ) Notice: Subject to any disclaimer, the term of this patent is extended or adjusted under 35 U.S.C. 154(b) by 13 days.

(21) Appl. No.: 14/913,654

(22) PCT Filed: Aug. 20, 2014

(86) PCT No.: PCT/US2014/051793
§ 371 (c)(1),
(2) Date: Feb. 22, 2016

(87) PCT Pub. No.: WO2015/026894
PCT Pub. Date: Feb. 26, 2015

(65) Prior Publication Data
US 2016/0222105 A1 Aug. 4, 2016

Related U.S. Application Data

(60) Provisional application No. 61/869,528, filed on Aug. 23, 2013, provisional application No. 61/907,691, filed on Nov. 22, 2013.

(30) Foreign Application Priority Data

Dec. 20, 2013 (EP) .................................... 13198859

(51) Int. Cl.
*C07K 16/28* (2006.01)
*C07K 16/30* (2006.01)
*A61K 39/00* (2006.01)

(52) U.S. Cl.
CPC .......... *C07K 16/28* (2013.01); *C07K 16/2803* (2013.01); *C07K 16/2809* (2013.01); *C07K 16/3046* (2013.01); *A61K 2039/505* (2013.01); *A61K 2039/545* (2013.01); *C07K 2317/24* (2013.01); *C07K 2317/31* (2013.01); *C07K 2317/33* (2013.01); *C07K 2317/35* (2013.01); *C07K 2317/52* (2013.01); *C07K 2317/524* (2013.01); *C07K 2317/526* (2013.01); *C07K 2317/56* (2013.01); *C07K 2317/624* (2013.01); *C07K 2317/626* (2013.01); *C07K 2317/64* (2013.01); *C07K 2317/73* (2013.01); *C07K 2317/732* (2013.01); *C07K 2317/92* (2013.01); *C07K 2317/94* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 4,526,938 A | 7/1985 | Churchill et al. |
| 4,752,601 A | 6/1988 | Hahn |
| 4,800,078 A | 1/1989 | Prince et al. |
| 4,980,286 A | 12/1990 | Morgan et al. |
| 5,116,964 A | 5/1992 | Capon et al. |
| 5,128,326 A | 7/1992 | Balazs et al. |

(Continued)

FOREIGN PATENT DOCUMENTS

| | | |
|---|---|---|
| EP | 0327378 | 8/1989 |
| EP | 1354600 | 10/2003 |

(Continued)

OTHER PUBLICATIONS

US 6,331,391, 12/2001, Wittrup et al. (withdrawn)

(Continued)

*Primary Examiner* — Nelson B Moseley, II
(74) *Attorney, Agent, or Firm* — William C. Schrot; AuerbachSchrot LLC

(57) ABSTRACT

The present invention is directed to bi-specific monovalent diabodies that comprise two polypeptide chains and which possess at least one binding site specific for an epitope of CD3 and one binding site specific for an epitope of gpA33 (i.e., a "gpA33×CD3 bi-specific monovalent diabody"). The present invention also is directed to bi-specific monovalent diabodies that comprise an immunoglobulin Fc Domain ("bi-specific monovalent Fc diabodies") and are composed of three polypeptide chains and which possess at least one binding site specific for an epitope of gpA33 and one binding site specific for an epitope of CD3 (i.e., a "gpA33×CD3 bi-specific monovalent Fc diabody"). The bi-specific monovalent diabodies and bi-specific monovalent Fc diabodies of the present invention are capable of simultaneous binding to gpA33 and CD3. The invention is directed to pharmaceutical compositions that contain such bi-specific monovalent diabodies or such bi-specific monovalent Fc diabodies. The invention is additionally directed to methods for the use of such diabodies in the treatment of cancer and other diseases and conditions.

20 Claims, 20 Drawing Sheets

(56) References Cited

U.S. PATENT DOCUMENTS

| | | | |
|---|---|---|---|
| 5,169,933 A | 12/1992 | Anderson et al. |
| 5,290,540 A | 3/1994 | Prince et al. |
| 5,348,876 A | 9/1994 | Michaelson et al. |
| 5,576,184 A | 11/1996 | Better et al. |
| 5,585,089 A | 12/1996 | Queen et al. |
| 5,624,821 A | 4/1997 | Winter et al. |
| 5,648,260 A | 7/1997 | Winter et al. |
| 5,679,377 A | 10/1997 | Bernstein et al. |
| 5,698,449 A | 12/1997 | Baumann et al. |
| 5,723,584 A | 3/1998 | Schatz |
| 5,736,135 A | 4/1998 | Goeddel et al. |
| 5,736,137 A | 4/1998 | Anderson et al. |
| 5,855,913 A | 1/1999 | Hanes et al. |
| 5,874,064 A | 2/1999 | Edwards et al. |
| 5,874,239 A | 2/1999 | Schatz |
| 5,888,533 A | 3/1999 | Dunn |
| 5,912,015 A | 6/1999 | Bernstein et al. |
| 5,916,597 A | 6/1999 | Lee et al. |
| 5,932,433 A | 8/1999 | Schatz |
| 5,934,272 A | 8/1999 | Lloyd et al. |
| 5,945,115 A | 8/1999 | Dunn et al. |
| 5,985,309 A | 11/1999 | Edwards et al. |
| 5,985,320 A | 11/1999 | Edwards et al. |
| 5,985,599 A | 11/1999 | McKenzie et al. |
| 5,989,463 A | 11/1999 | Tracy et al. |
| 6,019,968 A | 2/2000 | Platz et al. |
| 6,025,485 A | 2/2000 | Kamb et al. |
| 6,114,147 A | 9/2000 | Frenken et al. |
| 6,165,745 A | 12/2000 | Ward et al. |
| 6,194,551 B1 | 2/2001 | Idusogie et al. |
| 6,242,195 B1 | 6/2001 | Idusogie et al. |
| 6,277,375 B1 | 8/2001 | Ward |
| 6,300,065 B1 | 10/2001 | Kieke et al. |
| 6,423,538 B1 | 7/2002 | Wittrup et al. |
| 6,455,263 B2 | 9/2002 | Payan |
| 6,492,123 B1 | 12/2002 | Holliger et al. |
| 6,528,624 B1 | 3/2003 | Idusogie et al. |
| 6,538,124 B1 | 3/2003 | Idusogie et al. |
| 6,613,884 B1 | 9/2003 | Johansson et al. |
| 6,623,940 B1 | 9/2003 | Ledbetter et al. |
| 6,737,056 B1 | 5/2004 | Presta |
| 6,821,505 B2 | 11/2004 | Ward |
| 7,122,646 B2 | 10/2006 | Holliger et al. |
| 7,315,786 B2 | 1/2008 | Dahiyat et al. |
| 7,317,091 B2 | 1/2008 | Lazar et al. |
| 7,425,619 B2 | 9/2008 | Koenig et al. |
| 7,521,542 B2 | 4/2009 | Johnson et al. |
| 7,632,497 B2 | 12/2009 | Stavenhagen |
| 7,700,100 B2 | 4/2010 | Johnson et al. |
| 7,960,512 B2 | 6/2011 | Stavenhagen et al. |
| 8,003,774 B2 | 8/2011 | Stavenhagen et al. |
| 8,044,180 B2 | 10/2011 | Koenig et al. |
| 8,133,982 B2 | 3/2012 | Johnson et al. |
| 8,187,593 B2 | 5/2012 | Koenig et al. |
| 8,192,737 B2 | 6/2012 | Stavenhagen et al. |
| 8,193,318 B2 | 6/2012 | Koenig et al. |
| 8,216,574 B2 | 7/2012 | Stavenhagen et al. |
| 8,216,579 B2 | 7/2012 | Johnson et al. |
| 8,217,147 B2 | 7/2012 | Stavenhagen et al. |
| 8,586,713 B2 | 11/2013 | Davis et al. |
| 8,642,743 B2 | 2/2014 | Herne |
| 2002/0193571 A1 | 12/2002 | Carter et al. |
| 2003/0077282 A1 | 4/2003 | Bigler et al. |
| 2003/0158389 A1 | 8/2003 | Idusogie et al. |
| 2003/0229208 A1 | 12/2003 | Queen et al. |
| 2004/0002587 A1 | 1/2004 | Watkins et al. |
| 2004/0038339 A1 | 2/2004 | Kufer et al. |
| 2004/0058400 A1 | 3/2004 | Holliger et al. |
| 2004/0082039 A1 | 4/2004 | Gillies et al. |
| 2004/0110226 A1 | 6/2004 | Lazar et al. |
| 2004/0132101 A1 | 7/2004 | Lazar et al. |
| 2004/0185045 A1 | 9/2004 | Koenig et al. |
| 2004/0220388 A1 | 11/2004 | Mertens et al. |
| 2004/0259075 A1 | 12/2004 | Dimitrov et al. |
| 2005/0037000 A1 | 2/2005 | Stavenhagen et al. |
| 2005/0054832 A1 | 3/2005 | Lazar et al. |
| 2005/0100543 A1 | 5/2005 | Hansen et al. |
| 2005/0142539 A1 | 6/2005 | Herman |
| 2005/0257285 A1 | 11/2005 | Gupta |
| 2005/0260213 A1 | 11/2005 | Koenig et al. |
| 2006/0099216 A1 | 5/2006 | Cardy et al. |
| 2006/0193849 A1 | 8/2006 | Krauss et al. |
| 2007/0004909 A1 | 1/2007 | Johnson et al. |
| 2007/0036799 A1 | 2/2007 | Stavenhagen et al. |
| 2007/0135338 A1 | 6/2007 | O'Neil et al. |
| 2007/0140966 A1 | 6/2007 | Chang et al. |
| 2007/0274998 A1 | 11/2007 | Utku |
| 2008/0085277 A1 | 4/2008 | Cho et al. |
| 2008/0187517 A1 | 8/2008 | Herne |
| 2010/0174053 A1 | 7/2010 | Johnson et al. |
| 2010/0178298 A1* | 7/2010 | Lindhofer .......... C07K 16/2809 424/174.1 |
| 2010/0196362 A1 | 8/2010 | Stavenhagen et al. |
| 2010/0196372 A1 | 8/2010 | Johnson et al. |
| 2010/0322924 A1 | 12/2010 | Johnson et al. |
| 2011/0243941 A1 | 10/2011 | Stavenhagen et al. |
| 2011/0305714 A1 | 12/2011 | Stavenhagen et al. |
| 2012/0009186 A1 | 1/2012 | Koenig et al. |
| 2012/0014957 A1 | 1/2012 | Ghayur et al. |
| 2012/0034160 A1 | 2/2012 | Ghayur et al. |
| 2012/0087858 A1 | 4/2012 | Ghayur et al. |
| 2012/0141476 A1 | 6/2012 | Johnson et al. |
| 2012/0184716 A1 | 7/2012 | Fischer et al. |
| 2012/0189541 A1 | 7/2012 | Wu |
| 2012/0195900 A1 | 8/2012 | Ghayur et al. |
| 2012/0201746 A1 | 8/2012 | Liu et al. |
| 2012/0219551 A1 | 8/2012 | Johnson et al. |
| 2012/0237442 A1 | 9/2012 | Rossi et al. |
| 2012/0258108 A1 | 10/2012 | Ghayur et al. |
| 2012/0263711 A1 | 10/2012 | Stavenhagen et al. |
| 2012/0263722 A1 | 10/2012 | Ghayur et al. |
| 2012/0269811 A1 | 10/2012 | Johnson et al. |
| 2012/0276094 A1 | 11/2012 | Stavenhagen et al. |
| 2012/0276608 A1 | 11/2012 | Chang et al. |
| 2012/0289418 A1 | 11/2012 | Willard-Gallo et al. |
| 2012/0294796 A1 | 11/2012 | Johnson et al. |
| 2013/0149236 A1 | 6/2013 | Moore et al. |

FOREIGN PATENT DOCUMENTS

| | | |
|---|---|---|
| JP | 2007-531788 | 10/2005 |
| WO | WO 88/07089 | 9/1988 |
| WO | WO 89/07142 | 8/1989 |
| WO | WO 91/05548 | 5/1991 |
| WO | WO 92/16562 | 10/1992 |
| WO | WO 92/19244 | 12/1992 |
| WO | WO 93/22332 | 11/1993 |
| WO | WO 94/18330 | 8/1994 |
| WO | WO 94/29351 | 12/1994 |
| WO | WO 95/05468 | 2/1995 |
| WO | WO 96/20698 | 7/1996 |
| WO | WO 97/28267 | 8/1997 |
| WO | WO 97/34631 | 9/1997 |
| WO | WO 97/44013 | 11/1997 |
| WO | WO 97/44362 | 11/1997 |
| WO | WO 97/32572 | 12/1997 |
| WO | WO 98/05787 | 2/1998 |
| WO | WO 98/23289 | 6/1998 |
| WO | WO 98/31346 | 7/1998 |
| WO | WO 98/52975 | 11/1998 |
| WO | WO 99/15154 | 4/1999 |
| WO | WO 99/20253 | 4/1999 |
| WO | WO 99/43713 | 9/1999 |
| WO | WO 99/51642 | 10/1999 |
| WO | WO 99/58572 | 11/1999 |
| WO | WO 00/09560 | 2/2000 |
| WO | WO 99/66903 | 2/2000 |
| WO | WO 00/42072 | 7/2000 |
| WO | WO 01/11059 | 2/2001 |
| WO | WO 02/02781 | 1/2002 |
| WO | WO 02/060919 | 8/2002 |
| WO | WO 02/086070 | 10/2002 |
| WO | WO 03/074679 | 9/2003 |
| WO | WO 03/101485 | 12/2003 |

(56) References Cited

FOREIGN PATENT DOCUMENTS

| | | |
|---|---|---|
| WO | WO 04/001064 | 12/2003 |
| WO | WO 2004/016750 | 2/2004 |
| WO | WO 2004/029207 | 4/2004 |
| WO | WO 2004/065423 | 8/2004 |
| WO | WO 2004/074455 | 9/2004 |
| WO | WO 2004/099249 | 11/2004 |
| WO | WO 2005/070963 | 8/2005 |
| WO | WO 2005/097202 | 10/2005 |
| WO | WO 2006/020114 | 2/2006 |
| WO | WO 2006/113665 | 10/2006 |
| WO | WO 2008/157379 | 12/2008 |
| WO | WO 2010/080538 | 12/2009 |
| WO | WO 2012/018687 | 7/2011 |
| WO | WO 2012/162068 | 5/2012 |
| WO | WO 2012/162067 | 11/2012 |

OTHER PUBLICATIONS

Zuo et al. (2000) "*An efficient route to the production of an IgG-like bispecific antibody,*" PE 13(5):361-367.
Extended European Search Report (EP14837376.4; dated Apr. 3, 2017; 8 pages).
Abud H.E. et al. (2000) "The Murine A33 Antigen Is Expressed at Two Distinct Sites During Development, The ICM of the Blastocyst and the Intestinal Epithelium," Mech. Dev. 98(1-2):111-114.
Ackerman, M.E. et al. (2008) "A33 Antigen Displays Persistent Surface Expression," Cancer Immunol. Immunother. 57(7):1017-1027.
Agliano, A. et al. (2008) "Human Acute Leukemia Cells Injected in NOD/Ltsz-Scid/IL-2Rgamma Null Mice Generate a Faster and More Efficient Disease Compared to Other NOD/Scid-Related Strains," Int. J. Cancer 123(9):2222-2227.
Alt et al., "Novel Tetravalent and Bispecific IgG-Like Antibody Molecules Combining Single-Chain Diabodies with the Immunoglobin Gamma 1 Fc or CH3 Region," FEBS Letters 454: 90-94, 1999.
Altman et al., "Phenotypic Analysis of Antigen-Specific T Lymphocytes", Science 274:94-96, 1996.
Angal et al., "A single amino acid substitution abolishes the heterogeneity of chimeric mouse-human (IgG4) antibody," Mol Immunol 30 :105-108, 1993.
Anonymous, "Boehringer Ingelheim and MacroGenics Announce Global Alliance to discover, Develop and Commercialize DART(tm)-Based Antibody Therapeutics;" Press Release of MacroGenics, Inc.; Oct. 26, 2010; 3 pages.
Anonymous, "MacroGenics Enters Global Research Collaboration and License Agreement with Pfizer;" Press Release of MacroGenics, Inc.; Oct. 26, 2010; 2 pages.
Apostolovic, B. et al. (2008) "pH-Sensitivity of the E3-K3 Heterodimeric Coiled Coil," Biomacromolecules 9:3173-3180.
Armour et al., "Differential binding to human FcgammaRIIa and FcgammaRIIb receptors by human IgG wildtype and mutant antibodies," Mol Immunol 40 :585-593, 2003.
Armour et al., "Recombinant human IgG molecules lacking Fcgamma receptor I binding and monocyte triggering activities," Eur J Immunol 29:2613-2624, 1999.
Armour et al., "The contrasting IgG-binding interactions of human and herpes simplex virus Fc receptors," Biochemical Society Transactions 30:495-500, 2002.
Armstrong, S. et al. "Heterogeneity of IgG1 monoclonal anti-Rh(D): an investigation using ADCC and macrophage binding assays," Brit. J. Haematol. 66:257-262 (1987).
Arndt, K.M. et al. (2001) "Helix-stabilized Fx (hsFv) Antibody Fragments: Substituting the Constant Domains of a Fab Fragment for a Heterodimeric Coiled-coil Domain," J. Molec. Biol. 312:221-228.
Arndt, K.M. et al. (2002) "Comparison of in Vivo Selection and Rational Design of Heterodimeric Coiled Coils," Structure 10:1235-1248.

Asano, R. et al.(2004) "A Diabody for Cancer Immunotherapy and Its Functional Enhancement by Fusion of Human Fc Region," Abstract 3P-683, J. Biochem. 76(8):992.
Atwell et al. (1997) "Stable Heterodimers from Remodeling the Domain Interface of a Homodimer Using a Phase Display Library," J. Mol. Biol. 270:26-35.
Baeuerle, P.A. et al. (2009) "Bispecific T-Cell Engaging Antibodies for Cancer Therapy," Cancer Res. 69(12):4941-4944.
Baggiolini M, Dewald B. "Cellular models for the detection and evaluation of drugs that modulate human phagocyte activity," Experientia. Oct. 15;44(10):841-848, 1988.
Barendswaard, E.C. et al. (1998) "Rapid and Specific Targeting of Monoclonal Antibody A33 to a Colon Cancer Xenograft in Nude Mice," Int. J. Oncol. 12(1):45-53.
Barendswaard, E.C. et al. (2001) "Relative Therapeutic Efficacy of (125) I- and (131) I-Labeled Monoclonal Antibody A33 in a Human Colon Cancer Xenograft," J. Nucl. Med. 42(8):1251-1256.
Bedzyk et al. (1989) "Comparison of Variable Region Primary Structures Within an Anti-Fluorescein Idiotype Family," J. Biol. Chem, 264(3):1565-1569.
Boder and Wittrup, "Optimal screening of surface-displayed polypeptide libraries," Biotechnol Prog 14:55-62, 1998.
Boder and Wittrup, "Yeast surface display for directed evolution of protein expression, affinity, and stability," Methods in Enzymology 328:430-444, 2000.
Boder and Wittrup, 1997, "Yeast surface display for screening combinatorial polypeptide libraries", Nature Biotechnology 15:553-557.
Boder et al., "Directed evolution of antibody fragments with monovalent femtomolar antigen-binding affinity," Proc. Natl. Acad. Sci. USA 97:10701-10705, 2000.
Boucher, C. et al. (2010) "Protein Detection by Western Blot Via Coiled-Coil Interactions," Analytical Biochemistry 399:138-140.
Bredius et al., "Role of neutrophil Fc gamma RIIa (CD32) and Fc gamma RIIIb (CD16) polymorphic forms in phagocytosis of human IgG1- and IgG3-opsonized bacteria and erythrocytes," Immunology 83:624-630, 1994.
Brekke et al., "Human IgG isotype-specific amino acid residues affecting complement-mediated cell lysis and phagocytosis.," Eur J Immunol 24:2542-2547, 1994.
Brown EJ., "In Vitro Assays of Phagocytic Function of Human Peripheral Blood Leukocytes: Receptor Modulation and Signal Transduction," vol. 45 (Microbes as Tools for Cell Biology) in Methods in Cell Biololgy, Russell ed. Academic Press Inc. pp. 147-164, 1994.
Buchwald et al. (1980) "Long-Term, Continuous Intravenous Heparin Administration by an Implantable Infusion Pump in Ambulatory Patients with Recurrent Venous Thrombosis," Surgery 88:507-516.
Burmeister et al., "Crystal structure of the complex of rat neonatal Fc receptor with Fc," Nature 372:379-383, 1994.
Burton and Woof, "Human antibody effector function," Advances in Immunology 51:1-84, 1992.
Burton et al., "Molecular recognition of antibody (IgG) by cellular Fc receptor (FcRI)," Mol Immunol 25:1175-1181, 1988.
Burton, "Immunoglobulin G: functional sites," Mol Immunol 22:161-206, 1985.
Cachia, P.J. et al. (2004) "Synthetic Peptide Vaccine Development: Measurement of Polyclonal Antibody Affinity and Cross-Reactivity Using a New Peptide Capture and Release System for Surface Plasmon Resonance Spectroscopy," J. Mol. Recognit. 17:540-557.
Canfield and Morrison, "The binding affinity of human IgG for its high affinity Fc receptor is determined by multiple amino acids in the CH2 domain and is modulated by the hinge region," J Exp Med 173:1483-1491, 1991.
Cao et al., (2003) "Bispecific Antibody Conjugates in Therapeutics," Adv. Drug Deliv. Rev. 55:171-197.
Caron et al., "Engineered humanized dimeric forms of IgG are more effective antibodies," J Exp Med 176:1191-5, 1992.
Carrasquillo, J. A. et al. (2011) "(124) I-huA33 Antibody Pet of Colorectal Cancer," J. Nucl. Med. 52(8):1173-1180.
Carter et al., "Humanization of an anti-p185HER2 antibody for human cancer therapy," Proc. Natl. Acad. Sci. USA 89:4285-4289, 1992.

(56) References Cited

OTHER PUBLICATIONS

Cartron et al., "Therapeutic activity of humanized anti-CD20 monoclonal antibody and polymorphism in IgG Fc receptor FcgammaRIIIa gene,"Blood 99 :754-758, 2002.

Chappel et al., "Identification of a secondary Fc gamma RI binding site within a genetically engineered human IgG antibody," J Biol. Chem 268:25124-25131, 1993.

Chappel et al., "Identification of the Fc gamma receptor class I binding site in human IgG through the use of recombinant IgG1-IgG2 hybrid and point-mutated antibodies," Proc. Natl. Acad. Sci USA 88:9036-9040, 1991.

Chetty, R. et al. (1994) "CD3: Structure, Function and the Role of Immunostaining in Clinical Practice," J. Pathol. 173:303-307.

Choi, B. et al. (2011) "Human B Cell Development and Antibody Production in Humanized NOD/SCID/IL-2Rγ(Null) NSG Mice Conditioned by Busulfan," J. Clin. Immunol. 31(2):253-264.

Chong, G. et al. (2005) "Phase I Trial of 131I-HuA33 in Patients with Advanced Colorectal Carcinoma," Clin. Cancer Res. 11(13):4818-4826.

Chu, P. G. et al. (2001) "CD79: A Review," Appl. Immunohistochem. Molec. Morphol. 9(2):97-106.

Ciccimarra et al., "Localization of the IgG effector site for monocyte receptors," Proc. Natl. Acad. Sci. U.S.A. 72 :2081-2083, 1975.

Clynes and Ravetch, "Cytotoxic antibodies trigger inflammation through Fc receptors," Immunity 3:21-26, 1995.

Clynes et al., "Fc receptors are required in passive and active immunity to melanoma," Proc. Natl. Acad. Sci USA 95:652-656, 1998.

Clynes et al., "Inhibitory Fc receptors modulate in vivo cytoxicity against tumor targets," Nature Medicine 6 :443-446, 2000.

Clynes et al., "Modulation of immune complex-induced inflammation in vivo by the coordinate expression of activation and inhibitory Fc receptors," J Exp Med 189:179-185, 1999.

Clynes et al., "Uncoupling of immune complex formation and kidney damage in autoimmune glomerulonephritis," Science 279:1052-1054, 1998.

Coelho, V. et al. (2007) "Design, Construction, and in Vitro Analysis of A33scFv: CDy, A Recombinant Fusion Protein for Antibody-Directed Enzyme Prodrug Therapy in Colon Cancer," Int. J. Oncol. 31(4)951-957.

Cuesta, A.M. et al. (2010) "Multivalent Antibodies: When Design Surpasses Evolution," Trends in Biotechnol., 28(7):355-362.

De Crescenzo, G.D. et al. (2003) "Real-Time Monitoring of the Interactions of Two-Stranded de novo Designed Coiled-Coils: Effect of Chain Length on the Kinetic and Thermodynamic Constants of Binding," Biochemistry 42:1754-1763.

de Haas, Wien Kin "IgG-Fc receptors and the clinical relevance of their polymorphisms," Wien Klin Wochenscha 113:825-831, 2001.

de Kruif, J. et al. (1996) "Leucine Zipper Dimerized Bivalent and Bispecific scFv Antibodies from a Semi-Synthetic Antibody Phage Display Library," J. Biol. Cherm. 271(13):7630-7634.

Deckert, P.M. et al. (2000) "Pharmacokinetics and Microdistribution of PolyEthylene Glycol-Modified Humanized A33 Antibody Targeting Colon Cancer Xenografts," Int. J. Cancer. 87(3):382-390.

Deisenhofer, "Crystallographic refinement and atomic models of a human Fc fragment and its complex with fragment B of protein a Form *Staphylococcus aureus* at 2.9- and 2.8-A resolution," Biochem. 20:2361-2370, 1981.

Deo et al., "Clinical significance of IgG Fc receptors and Fc Gamma R-directed immunotherapies," Immunology Today 18:127-135, 1997.

Duncan and Winter, "Localization of the binding site for the human high-affinity Fc receptor on IgG," Nature 332:563-564, 1988.

Duncan and Winter, "The binding site for C1q on IgG," Nature 332 :738-740, 1988.

During et al. (1989) "Controlled Release of Dopamine from a Polymeric Brain Implant: In Vivo Characterization," Am. Neurol. 25:351-356.

Edberg et al., "Modulation of Fcgamma and Complement Receptor Function by the Glycosyl-Phosphatidylinositol-Anchored Form of FcgammaRIII," Journal of Immunology 152: 5826-5835, 1994.

European Search Report EP 06750508 (dated 2010) (19 pages).

European Search Report EP 08771050 (dated 2010) (13 pages).

Fernandez-Rodriguez, J. et al. (2012) "Induced Heterodimerization and Purification of Two Target Proteins by a Synthetic Coiled-Coil Tag," Protein Sci. 21:511-519.

FitzGerald, et al., "Improved tumour targeting by disulphide stabilized diabodies expressed in Pichia pastoris," Protein Engineering 10(10): 1221-1225, 1997.

Flesch and Neppert, "Functions of the Fc receptors for immunoglobulin G," J Clin Lab Anal 14:141-156, 2000.

Gao, Y. et al. (2004) "Efficient Inhibition of Multidrug-Resistant Human Tumors with a Recombinant Bispecific Anti-P-Glycoprotein X Anti-CD3 Diabody," Leukemia 18(3):513-520.

Gergeley et al., "Fc receptors on lymphocytes and K cells," Biochemical Society Transactions 12:739-743, 1984.

Gergely and Sarmay, "The two binding-site models of human IgG Binding Fc gamma receptors," FASEB J 4:3275-3283, 1990.

Ghosh, T.S. et al. (2009) "End-To-End and End-To-Middle Interhelical Interactions: New Classes of Interacting Helix Pairs in Protein Structures," Acta Cryst. D65:1032-1041.

Greenwood and Clark, "Effector functions of matched sets of recombinant human IgG subclass antibodies". (final version edited Feb. 11, 1993).

Greenwood et al., "Engineering multiple-domain forms of the therapeutic antibody CAMPATH-1H: effects on complement lysis," Therapeutic Immunology 1:247-255, 1994.

Greenwood et al., "Structural motifs involved in human IgG antibody effector functions," Eur J Immunol 23:1098-1104, 1993.

Grigoryan, G. et al. (2008) "Structural Specificity in Coiled-Coil Interactions," Curr. Opin. Struc. Biol. 18:477-483.

Guo, J. et al. (2003) "[New Type Recombinant Antibody Fragment Scfv Multimer and Cancer Targeting]," Sheng Wu Yi Xue Gong Cheng Xue Za Zhi 20(2):361-365 (Abstract Only; Article in Chinese).

Guo, N. et al. (2005) "The Development of New Formats of Engineered Bispecific Antibodies," in Trends in Immunology Research, Veskler, Ed. Nova Science Publishers. Chapter 3:33-47.

Hadley et al., "The functional activity of Fc gamma RII and Fc gamma RIII on subsets of human lymphocytes," Immunology 76:446-451, 1992.

Hatta et al., "Association of Fc gamma receptor IIIB, but not of Fc gamma receptor IIA and IIIA polymorphisms with systemic lupus erythematosus in Japanese," Genes and Immunity 1:53-60, 1999.

Hayes, Fc Engineering to Enhance Monoclonal Antibody Effector Functions. (Presentation) Xecor, CA, 2003.

Heath J. K. et al. (1997) "The Human A33 Antigen Is a Transmembrane Glycoprotein and a Novel Member of the Immunoglobulin Superfamily," Proc. Natl. Acad. Sci. (U.S.A.) 94(2):469-474.

Herzenberg et al., "The history and future of the fluorescence activated cell sorter and flow cytometry: a view from Stanford," Clinical Chem. 2002:48:1819-1827, 2002.

Heyman, "Regulation of antibody responses via antibodies, complement, and Fc receptors," Annu Rev Innnunol 18:709-737, 2000.

Hogarth et al., "Characterization of FcR Ig-binding sites and epitope mapping," Immunomethods 4 :17-24, 1994.

Holler et al., "In vitro evolution of a T cell receptor with high affinity for peptide-MHC," Proc. Natl. Acad. Sci. U.S.A. 97 :5387-92, 2000.

Holliger et al. (1996) "Specific Killing of Lymphoma Cells by Cytotoxic T-Cells Mediated by a Bispecific Diabody," Protein Eng. 9:299-305.

Holliger et al., (1999) "Carcinoembryonic Antigen (CEA)-Specific T-cell Activation in Colon Carcinoma Induced by Anti-CD3 x Anti-CEA Bispecific Diabodies and B7 x Anti-CEA Bispecific Fusion Proteins," Cancer Res. 59:2909-2916.

Holliger et al., "Engineered antibody fragments and the rise of single domains," Nature Biotechnology 23(9): 1126-1135, Sep. 2005.

(56) References Cited

OTHER PUBLICATIONS

Holliger, et al. (1993) "'Diabodies': Small Bivalent and Bispecific Antibody Fragments," Proc. Natl. Acad. Sci. (U.S.A.) 90:6444-6448.
Howard et al. (1989) "Intracerebral Drug Delivery in Rats with Lesion-Induced Memory Deficits," J. Neurosurg. 7(1):105-112.
Hudson, P.J. et al. (1999) "High avidity scFv multimers; diabodies and triabodies," J. Immunol. Methods 231(1-2):177-189.
Hulett et al., "Chimeric Fc receptors identify functional domains of the murine high affinity receptor for IgG," J Immunol 147 :1863-1868, 1991.
Hulett et al., "Identification of the IgG binding site of the human low affinity receptor for IgG Fc gamma RII. Enhancement and ablation of binding by site-directed mutagenesis," J. Biol. Chem. 269:15287-15293, 1994.
Hulett et al., "Multiple regions of human Fc gamma RII (CD32) contribute to the binding of IgG," J. Biol. Chem. 270:21188-21194, 1995.
Idusogie et al., "Engineered antibodies with increased activity to recruit complement," J Immunol 166 :2571-2575, 2001.
Idusogie et al., "Mapping of the C1q binding site on rituxan, a chimeric antibody with a human IgG1 Fc," J Immunol 164: 4178-4184, 2000.
Infante, J. R. et al. (2013) "Safety, Pharmacokinetics and Pharmacodynamics of the Anti-A33 Fully-Human Monoclonal Antibody, KRN330, in Patients with Advanced Colorectal Cancer," Eur. J. Cancer. 49(6):1169-1175.
International Search Report and Written Opinion PCT/US2009/068577 (dated 2010) (14 pages).
International Search Report and Written Opinion PCT/US2011/045922 (dated 2011) (4 pages).
International Search Report and Written Opinion PCT/US2014/051793 (dated 2015) (32 pages).
Isaacs et al., "A therapeutic human IgG4 monoclonal antibody that depletes target cells in humans," Clin Exp Immunol 106 :427-433, 1996.
Isaacs et al., "Therapy with monoclonal antibodies. An in vivo model for the assessment of therapeutic potential," J Immunol 148 :3062-3071, 1992.
Isaacs et al., "Therapy with monoclonal antibodies. II. The contribution of Fc gamma receptor binding and the influence of C(H)1 and C(H)3 domains on in vivo effector function," J Immunol 161 :3862-3869, 1998.
Jassal et al., "Remodeling glycans on IgG by genetic re-engineering," Biochem Soc Trans 26: S113, 1998.
Jefferis and Lund, "Interaction sites on human IgG-Fc for FcgammaR: current models," Immunology Letters 82 :57-65, 2002.
Jefferis et al., "IgG-Fc-mediated effector functions: molecular definition of interaction sites for effector ligands and the role of glycosylation," Immunol Rev 163:59-76, 1998.
Jefferis et al., "Molecular definition of interaction sites on human IgG for Fc receptors (huFc gamma R)," Mol Immunol 27 :1237-1240, 1990.
Jefferis et al., "Recognition sites on human IgG for FC gamma receptors: the role of glycosylation," Immunol Lett 44 :111-7, 1995.
Jendeberg et al., "Engineering of Fc (1) and Fc (3) from human immunoglobulin G to analyse subclass specificity for staphlococcal protein A," J Immunological Methods 201 :25-34, 1997.
Johnson et al., (2010) "Effector Cell Recruitment with Novel Fv-based Dual-affinity Re-targeting Protein Leads to Potent Tumor Cytolysis and in Vivo B-cell Depletion," J. Mol. Biol (399) pp. 436-449.
Johnston, A.P. et al. (2012) "Targeting Cancer Cells: Controlling the Binding and Internalization of Antibody-Funcitonalized Capsules" ACS Nano. 6(8):6667-6674.
Johnstone, C. N. et al. (2000) "Characterization of Mouse A33 Antigen, A Definitive Marker for Basolateral Surfaces of Intestinal Epithelial Cells," Am. J. Physiol. Gastrointest. Liver Physiol. 279(3): G500-G510.

Joliot et al. (1991) "Antennapedia Homeobox Peptide Regulates Neural Morphogenesis," Proc. Natl. Acad. Sci. (U.S.A.) 88:1864-1868.
Kadar et al., "Modulatory effect of synthetic human IgG Fc peptides on the in vitro immune response of murine spleen cells," Int J Immunpharmacol 13 :1147-55, 1991.
Kadar et al., "Synthetic peptides comprising defined sequences of CH-2 and CH-3 domains of human IgG1 induce prostaglandin E2 production from human peripheral blood mononuclear cells," Immunol Lett 32:59-63, 1992.
Kato et al., "Structural basis of the interaction between IgG and Fcγ receptors," J Mol Biol 295:213-224, 2000.
Keler et al., "Differential effect of cytokine treatment on Fc alpha receptor I- and Fc gaimna receptor I-mediated tumor cytotoxicity by monocyte-derived macrophages," J. of Immunol. 164:5746-52, 2000.
Kieke et al., "Selection of functional T cell receptor mutants from a yeast surface-display library," Proc. Natl. Acad. Sci. U.S.A. 96 :5651-56, 1999.
Kim et al., "Analysis of FcγRIII and IgG Fc polymorphism reveals functional and evolutionary implications of protein-protein interaction," J Mol Evol 53:1-9, 2001.
Klein et al., "Expression of biological effector functions by immunoglobulin G molecules lacking the hinge region," Proc. Natl. Acad. Sci. U.S.A. 78 :524-528, 1981.
Koene et al., "Fc gammaRIIIa-158V-F polymorphism influences the binding of IgG by natural killer cell Fc gammaRIIIa, independently of the Fc gammaRIIIa-48L-R-H phenotype," Blood 90 :1109-1114, 1997.
Kontermann, R.E. (2005) "Recombinant Bispecific Antibodies for Cancer Therapy," Acta. Pharmacology. Sin. 26(1):1-9.
Koppe, M.J. et al. (2005) "Radioimmunotherapy and Colorectal Cancer," Br. J. Surg. Mar;92(3):264-276.
Korn, A.A. et al. (2001) "Dimeric and Trimeric Antibodies: High Avidity Scfvs for Cancer Targeting," Biomol. Eng. 18(3):95-108.
Kranz et al., "Mechanisms of ligand binding by monoclonal anti-fluorescyl antibodies," J. Biol. Chem. 257:6987-6995, 1982.
Kuhns, M.S. et al. (2006) "Deconstructing the Form and Function of the TCR/CD3 Complex," Immunity. Feb. 2006; 24(2):133-139.
Kumpel, B.M. Brit. "Human monoclonal anti-D antibodies," J. Haematol. 71:415-420 (1989).
Langer (1990) "New Methods of Drug Delivery," Science 249:1527-1533.
Le Gall, F. et al. (Epub May 4, 2004) "Effect of Linker Sequences Between the Antibody Variable Domains on the Formation, Stability and Biological Activity of a Bispecific Tandem Diabody," Protein Eng des Sel. 17(4):357-366.
Le, P.U. et al. (2009) "*Escherichia coli* Expression and Refolding of E-K-Coil-Tagged EGF Generates Fullybioactive EGF for Diverse Applications," Protein Expression and Purification 64:108-117.
Lehmann et al., "Phagocytosis: measurement by flow cytometry," J Immunol Methods. 243(1-2):229-42, 2000.
Lehrnbecher et al., "Variant genotypes of the low-affinity Fcgamma receptors in two control populations and a review of low-affinity Fcgamma receptor polymorphisms in control and disease populations," Blood 94:4220-4232, 1999.
Levy et al. (1985) "Inhibition of Calcification of Bioprosthetic Heart Valves by Local Controlled-Release Diphosphonate," Science 228:190-192.
Li et al., "Reconstitution of human Fc gamma RIII cell type specificity in transgenic mice," J Exp Med 183 :1259-1263, 1996.
Litowski, J.R. et al. (2002) "Designing Heterodimeric Two-Stranded α-Helical Coiled-Coils: The Effects of Hydrophobicity and α-Helical Propensity on Protein Folding, Stability, and Specificity," J. Biol. Chem. 277:37272-37279.
Liu et al., "Production of a mouse-human chimeric monoclonal antibody to CD20 with potent Fc-dependent biologic activity," J. Immunol. 139:3521-3526, 1987.
Lu, D. et al., (2003) "Di-cliabody: a novel tetravalent bispecific antibody molecule by design," J. Immunol. Meth. 279:219-232.
Lu, D. et al., (2004) "The effect of variable domain orientation and arrangement on the antigen-binding activity of a recombinant human bispecific diabody," BBRC 318: 507-513.

(56) References Cited

OTHER PUBLICATIONS

Lu, et al., (2005) "A Fully Human Recombinant IgG-like Bispecific Antibody to Both the Epidermal Growth Factor Receptor and the Insulin-like Growth Factor Receptor for Enhanced Antitumor Activity," The Journal of Biological Chemistry, vol. 280(20) pp. 19665-19672.

Lund et al., "Expression and characterization of truncated forms of humanized L243 IgG1. Architectural features can influence synthesis of its oligosaccharide chains and affect superoxide production triggered through human Fcgamma receptor I," Eur J Biochem 267 :7246-57, 2000.

Lund et al., "Human Fc gamma RI and Fc gamma RII interact with distinct but overlapping sites on human IgG," J Immunol 147 :2657-62, 1991.

Lund et al., "Multiple binding sites on the CH2 domain of IgG for mouse Fc gamma RII," Molecular Immunology 29:53-59, 1992.

Lund et al., "Multiple interactions of IgG with its core oligosaccharide can modulate recognition by complement and human Fc gamma receptor I and influence the synthesis of its oligosaccharide chains," J Immunol 157 :4963-4969, 1996.

Lund et al., "Oligosaccharide-protein interactions in IgG can modulate recognition by Fc gamma receptors," FASEB J 9 :115-119, 1995.

Luo et al. (1995) "VL-Linker-VH Orientation-Dependent Expression of Single Chain Fv Containing an Engineered Disulfide-Stabilized Bond in the Framework Regions," J. Biochem. 4(118):825-831.

Maenaka et al., "The human low affinity Fcgamma receptors IIa, IIb, and III bind IgG with fast kinetics and distinct thermodynamic properties," J Biol Chem 48 :48898-904, 2001.

Mariuzza et al, (1987) "The Structural Basis of Antigen-Antibody Recognition," Annual Review of Biophysics and Biophysical Chemistry 16:139-159.

Marvin et al., "Recombinant approaches to IgG-like bispecific antibodies," Acta Pharmacologica Sinica, 26(6): 649-658, Jun. 2005.

Mertens, N. et al., "New Recombinant Bi- and Trispecific Antibody Derivatives," In: Novel Frontiers in the Production of Compounds for Biomedical Use, vol. 1; van Broekhoven, A. et al. (Eds.); Kluwer Academic Publishers, Dordrecht, The Netherlands (2001).

Michaelsen et al., "One disulfide bond in front of the second heavy chain constant region is necessary and sufficient for effector functions of human IgG3 without a genetic hinge," Immunology 91 :9243-9247, 1994.

Moore, P.A. et al., (2011) "Application of Dual Affinity Retargeting Molecules to Achieve Optimal Redirected T-Cell Killing of B-Cell Lymphoma," Blood 117:4542-4551.

Morgan et al., "The N-terminal end of the CH2 domain of chimeric human IgG1 anti-HLA-DR is necessary for C1q, Fc gamma RI and Fc gamma RIII binding," Immunology 86 :319-324, 1995.

Morrison et al., "Structural determinants of IgG structure," Immunologist 2 :119-124, 1994.

Munn et al., "Phagocytosis of tumor cells by human monocytes cultured in recombinant macrophage colony-stimulating factor," J Exp Med. 172(1):231-7, 1990.

Nagarajan et al., "Ligand binding and phagocytosis by CD16 (Fc gamma receptor III) isoforms. Phagocytic signaling by associated zeta and gamma subunits in Chinese hamster ovary cells," J Biol Chem 270 :25762-25770, 1995.

Nakamura, T. et al. (1992) "Heterogeneity of Immunoglobulin-Associated Molecules on Human B Cells Identified by Monoclonal Antibodies," Proc. Natl. Acad. Sci. (USA) 89:8522-8526).

Neuberger et al., "Recombinant antibodies possessing novel effector functions," Nature 312 :604-608, 1984.

Ning et al. (1996) "Intratumoral Radioimmunotherapy of a Human Colon Cancer Xenograft Using a Sustained-Release Gel," Radiotherapy & Oncology 39:179-189.

Norderhaug et al., "Chimeric mouse human IgG3 antibodies with an IgG4-like hinge region induce complement-mediated lysis more efficiently than IgG3 with normal hinge," Eur J Immunol 21:2379-84, 1991.

Nose and Leanderson, "Substitution of asparagine324 with aspartic acid in the Fc portion of mouse antibodies reduces their capacity for C1q binding," Eur J Immunol 19 :2179-81, 1989.

Okazaki et al., "Fucose depletion from human IgG1 oligosaccharide enhances binding enthalpy and association rate between IgG1 and FcgammaRIIIa," J Mol Biol 336 :1239-1249, 2004.

Olafsen et al., "Covalent disulfide-linked anti-CEA diabody allows site-specific conjugation and radiolabeling for tumor targeting applications," Protein Engineering, Design & Selection, 17(1): 21-27, 2004.

Orfao and Ruiz-Arguelles, "General concepts about cell sorting techniques," Clinical Biochem. 29:5-9, 1996.

Pack, P. : et al (1992) "Miniantibodies: Use of Amphipathic Helices to Produce Functional, Flexibly Linked Dimeric Fv Fragments with High Avidity in *Escherichia coli*," 31(6):1579-1584.

Panjideh, H. et al. (2008) "Biodistribution and Efficacy of [131I] A33scFv: CDy, A Recombinant Antibody-Enzyme Protein for Colon Cancer," Int. J. Oncol. 32(4):925-930.

Partridge et al., "The use of anti-IgG monoclonal antibodies in mapping the monocyte receptor site on IgG," Mol Immunol. 23(12):1365-72, 1986.

Perussia "Human Natural Killer Cell Protocols" in Methods Molecular Biology. vol. 121 (Campbell et al. eds.) Humana Press Inc., Totowa, NJ. 179-92, 2000.

Racki, W.J. et al. (2010) "NOD-Scid IL2rgamma(Null) Mouse Model of Human Skin Transplantation and Allograft Rejection," Transplantation 89(5):527-536.

Radaev and Sun, "Recognition of immunoglobulins by Fcgamma receptors," Molecular Immunology 38 :1073-1083, 2001.

Rankin et al. "CD32B, The Human Inhibitory Fc-γ Receptor IIB, As a Target for Monoclonal Antibody Therapy of B-Cell Lymphoma," (2006) Blood 108(7):2384-2391.

Ravetch (1994) "Fc Receptors: Rubor Redux," Cell 78:553-560.

Ravetch and Bolland, "IgG Fc receptors," Annu Rev Immunol 19:275-90, 2001.

Ravetch and Clynes, "Divergent roles for Fc receptors and complement in vivo," Annu Rev Immunol 16:421-432, 1998.

Ravetch and Kinet, "Fc receptors," Annu Rev Immunol 9:457-492, 1991.

Ravetech and Lanier, "Immune inhibitory receptors," Science 290:84-89, 2000.

Redpath et al., "The influence of the hinge region length in binding of human IgG to human Fcgamma receptors," Hum Immunol 59 :720-727, 1998.

Reff et al., "Depletion of B cells in vivo by a chimeric mouse human monoclonal antibody to CD20," Blood 83:435-445, 1994.

Ridgway et al. (1996) "Knobs-Into-Holes' Engineering of Antibody CH3 Domains for Heavy Chain Heterodimerization," Protein Engr. 9:617-621.

Riechmann et al., "Reshaping human antibodies for therapy," Nature. 332(6162):323-7, 1988.

Ritter, G. et al. (1997) "Characterization of Posttranslational Modifications of Human A33 Antigen, A Novel Palmitoylated Surface Glycoprotein of Human Gastrointestinal Epithelium," Biochem. Biophys. Res. Commun. 236(3):682-686.

Rothlisberger, D. et al. (2005) "Domain Interactions in the Fab Fragment: A Comparative Evaluation of the Single-chain Fv and Fab Format Engineered with Variable Domains of Different Stability," J. Molec. Biol. 347:773-789.

Sakamoto, J. et al. (2006) "A Phase I Radioimmunolocalization Trial of Humanized Monoclonal Antibody HuA33 in Patients with Gastric Carcinoma," Cancer Sci. 97(11):1248-1254.

Sanchez, P.V. et al. (2009) "A Robust Xenotransplantation Model for Acute Myeloid Leukemia," Leukemia 23(11):2109-2117.

Sarmay et al., "Ligand inhibition studies on the role of Fc receptors in antibody-dependent cell-mediated cytotoxicity," Mol Immunol 21 :43-51, 1984.

Sarmay et al., "Mapping and comparison of the interaction sites on the Fc region of IgG responsible for triggering antibody dependent

(56) References Cited

OTHER PUBLICATIONS cellular cytotoxicity (ADCC) through different types of human Fc gamma receptor," Mol Immunol 29 :633-639, 1992.
Sarmay et al., "The effect of synthetic peptides corresponding to Fc sequences in human IgG1 on various steps in the B cell activation pathway," Eur J Immunol 18 :289-294, 1988.
Sartelet, H. et al. (2012) "Description of a New Xenograft Model of Metastatic Neuroblastoma Using NOD/SCID/Il2rg Null (NSG) Mice," In Vivo 26(1):19-29.
Saudek et al. (1989) "A Preliminary Trial of the Programmable Implantable Medication System for Insulin Delivery," N. Engl. J. Med. 321:574-579.
Sautes-Fridman et al., "Fc gamma receptors: a magic link with the outside world," ASHI Quarterley, 4$^{th}$ Quarter:148-151, 2003.
Schaffner et al., "Chimeric interleukin 2 receptor alpha chain antibody derivatives with fused mu and gamma chains permit improved recruitment of effector functions," Mol Immunol 32 :9-20, 1995 (Erratum in 32 :1299, 1995).
Schatz et al., "Use of peptide libraries to map the substrate specificity of a peptide-modifying enzyme: a 13 residue consensus peptide specifies biotinylation in *Escherichia coli*," Bio-Technology 11:1138-1143, 2000.
Scott, A.M. et al. (2005) "A Phase I Trial of Humanized Monoclonal Antibody A33 in Patients with Colorectal Carcinoma; Biodistribution, Pharmacokinetics, and Quantitative Tumor Uptake," Clin. Cancer Res. 11(13):4810-4817.
Sensel et al., "Amino acid differences in the N-terminus of C(H)2 influence the relative abilities of IgG2 and IgG3 to activate complement," Molecular Immunology 34:1019-1029, 1997.
Shields et al., "High resolution mapping of the binding site on human IgG1 for Fc gamma RI, Fc gamma RH, Fc gamma RIII, and FcRn and design of IgG1 variants with improved binding to the Fc Gamma R," J Biol Chem 276 :6591-6604, 2001.
Shopes et al., "Recombinant human IgG1-murine IgE chimeric Ig. Construction, expression, and binding to human Fc gamma receptors," J Immunol 145 :3842-3848, 1990.
Shopes, "A genetically engineered human IgG mutant with enhanced cytolytic activity," J Immunol 148 :2918-2922, 1992.
Shopes, "A genetically engineered human IgG with limited flexibility fully initiates cytolysis via complement," Molecular Immunology 30 :603-609, 1993.
Shusta et al., "Directed evolution of a stable scaffold for T-cell receptor engineering," Nature Biotechnology 18:754-759, 2000.
Shusta et al., "Increasing the secretory capacity of *Saccharomyces cerevisiae* for production of single-chain antibody fragments," Nature Biotechnology 16:773-777, 1998.
Shusta et al., "Yeast polypeptide fusion surface display levels predict thermal stability and soluble secretion efficiency," J Mol Biol 292:949-956, 1999.
Silverberg, E. et al. (1989) "Cancer Statistics, 1989," CA Cancer J Clin. 39(1):3-20.
Smith and Morrison, "Recombinant polymeric IgG: an approach to engineering more potent antibodies," Bio-Technology 12:683-688, 1994.
Sondermann and Oosthuizen, "The structure of Fc Receptor-Ig complexes: considerations on stoichiometry and potential inhibitors," Immunology Letters, 82:51-56, 2002.
Sondermann et al., "Crystal structure of the soluble form of the human fcgamma-receptor IIb: a new member of the immunoglobulin superfamily at 1.7 A resolution," EMBO J 18:1095-1103, 1999.
Sondermann et al., "Molecular basis for immune complex recognition: a comparison of Fc-receptor structures," J. Mol. Biol. 309:737-749, 2001.
Sondermann et al., "The 3.2-A crystal structure of the human IgG1 Fc Fragment-Fc gammaRIII complex," Nature 406:267-273, 2000.
Song et al. (1995) "antibody Mediated Lung Targeting of Long-Circulating Emulsions," PDA Journal of Pharmaceutical Science & Technology 50:372-397.

Spranger, S. et al. (2012) "NOD/scid IL-2Rg(null) Mice: A Preclinical Model System to Evaluate Human Dendritic Cell-Based Vaccine Strategies in vivo," J. Transl. Med. 10:30.
Staerz et al. (1985) "Hybrid Antibodies Can Target Sites for Attack by T Cells," Nature 314:628-631.
Steinkruger, J.D. et al. (2012) "The d'—d—d' Vertical Triad is Less Discriminating Than the a'—a—a' Vertical Triad in the Antiparallel Coiled-coil Dimer Motif," J. Amer. Chem. Soc. 134(5):2626-2633.
Steplewski et al., "Biological activity of human-mouse IgG1, IgG2, IgG3, and IgG4 chimeric monoclonal antibodies with antitumor specificity," Proc. Natl. Acad. Sci. U.S.A. 85:4852-4856, 1988.
Stork, R. et al. (2007) "A Novel Tri-Functional Antibody Fusion Protein with Improved Pharmacokinetic Properties Generated by Fusing a Bispecific Single-Chain Diabody with an Albumin-Binding Domain from Streptococcal Protein G," Protein Engineering, Design & Selection 20(11):569-576.
Straussman, R. et al. (2007) "Kinking the Coiled Coil—Negatively Charged Residues at the Coiled-coil Interface," J. Molec. Biol. 366:1232-1242.
Strohmeier et al., "Role of the Fc Gamma R Subclasses Fc gamma RII and Fc gamma RIII in the activation of human neutrophils by low and high valency immune complexes," J Leukocyte Biol 58:415-422, 1995.
Sun, Z.J. et al. (2001) "Mechanisms Contributing to T-Cell Receptor Signaling and Assembly Revealed by the Solution Structure of an Ectodomain Fragment of the CD3ϵ: γ Heterodimer," Cell 105(7):913-923.
Sylvestre and Ravetch, "A dominant role for mast cell Fc receptors in the Arthus reaction," Immunity 5:387-390, 1996.
Sylvestre and Ravetch, "Fc receptors initiate the Arthus reaction: redefining the inflammatory cascade," Science 265:1095-1098, 1994.
Takai et al., "Augmented humoral and anaphylactic responses in Fc gamma RII-deficient mice," Nature 379:346-349, 1996.
Takai et al., "FcR gamma chain deletion results in pleiotrophic effector cell defects," Cell 76 :519-529, 1994.
Takai, "Roles of Fc receptors in autoimmunity," Nature Reviews 2:580-592, 2002.
Takemura, S. et al. (2000) "Construction of a Diabody (Small Recombinant Bispecific Antibody) Using a Refolding System," Protein Eng. 13(8):583-588.
Tamm et al., "The IgG binding site of human FcγRIIIB receptor involves CC' and FG loops of the membrane-proximal domain," J Biol Chem 271:3659-3666, 1996.
Tao et al., "Structural features of human immunoglobulin G that determine isotype-specific differences in complement activation," J Exp Med 178:661-667, 1993.
Tao et al., "The differential ability of human IgG1 and IgG4 to activate complement is determined by the COOH-terminal sequence of the CH2 domain," J Exp Med 173:1025-1028, 1991.
Thomas, S. et al. (2010) "Molecular Immunology Lessons from Therapeutic T-Cell Receptor Gene Transfer," Immunology 129(2):170-177.
Todorovska, A. et al. (2001) "Design and Application of Diabodies, Triabodies and Tetrabodies for Cancer Targeting," J. Immunol. Methods 248(1-2):47-66.
Trindandapani et al. (2002) "Regulated Expression and Inhibitory Function of FcgammaRIIB in Human Monocytic Cells," J. Biol. Chem. 277(7):5082-5089.
Tripet, B. et al. (2002) "Kinetic Analysis of the Interactions between Troponin C and the C-terminal Troponin I Regulatory Region and Validation of a New Peptide Delivery-Capture System used for Surface Plasmon Resonance," J. Molec. Biol. 323:345-362.
Tschmelitsch, J. et al. (1997) "Enhanced Antitumor Activity of Combination Radioimmunotherapy ($^{131}$I-Labeled Monoclonal Antibody A33) With Chemotherapy (Fluorouracil)," Cancer Res. 57(11):2181-2186.
Unkeless, J.C. et al. (1995) "Function of Human Fc Gamma RIIA and Fc Gamma RIIIB," Semin. Immunol. 7(1):37-44.
Van Sorge et al., "FcgammaR polymorphisms: Implications for function, disease susceptibility and immunotherapy," Tissue Antigens 61:189-202, 2003.

(56) References Cited

OTHER PUBLICATIONS

VanAntwerp and Wittrup, "Fine affinity discrimination by yeast surface display and flow cytometry," Biotechnol Prog 16:31-37, 2000.
Veri et al. (Epub Mar. 26, 2007) "Monoclonal antibodies capable of discriminating the human inhibitory Fcgamma-receptor IIB (CD32B) from the activating Fcgamma-receptor IIA (CD32A): biochemical, biological and functional characterization," Immunology 121(3):392-404.
Veri, et al. (Jul. 2010) "Therapeutic Control of B Cell Activation via Recruitment of Fcy Receptor IIb (CD32B) Inhibitory Function with a Novel Bispecific Antibody Scaffold," Arthritis & Rheumatism, vol. 62(7): 1933-1943.
Vidarte, "Serine 132 is the C3 covalent attachment point on the CH1 domain of human IgG1," J Biol Chem 276:38217-38233, 2001.
Von Bonin, M. et al. (2013) "In vivo Expansion of Co-Transplanted T Cells Impacts on Tumor Re-Initiating Activity of Human Acute Myeloid Leukemia in NSG Mice," PLoS One. 8(4): e60680.
Ward and Ghetie, "The effector functions of immunoglobulins: implications for therapy," Therapeutic Immunology 2:77-94, 1995.
Weng and Levy, "Two immunoglobulin G Fragment C receptor polymorphisms independently predict response to rituximab in patients with follicular lymphoma," J Clin Oncol 21:3940-3947, 2003.
Wiener, E. et al. "Differences between the activities of human monoclonal IgG1 and IgG3 anti-D antibodies of the Rh blood group system in their abilities to mediate effector functions of monocytes," Immunol. 65:159-163 (1988).
Wing et al., "Mechanism of first-dose cytokine-release syndrome by CAMPATH 1-H: Involvement of CD16 (FcγRIII) and CD11a-CD18 (LFA-1) on NK cells," J Clin Invest 98 :2819-2826, 1996.
Wingren et al., "Comparison of surface properties of human IgA, IgE, IgG and IgM antibodies with identical and different specificities," Scand J Immunol 44:430-436, 1996.
Wittrup, "The single cell as a microplate well," Nat Biotechnol 18:1039-1040, 2000.
Wittrup, "Protein engineering by cell-surface display," Curr, Opin. Biotechnol. 12:395-399, 2001.
Wong, N.A. et al. (2006) "EpCAM and gpA33 Are Markers of Barrett's Metaplasia," J. Clin. Pathol. 59(3):260-263.
Woof et al., "Localisation of the monocyte-binding region on human immunoglobulin G," Mol Immunol 23 :319-330, 1986.
Woolfson, D.N. (2005) "The Design of Coiled-Coil Structures and Assemblies," Adv. Prot. Chem. 70:79-112.
Wu et al. (1987) "Receptor-Mediated in Vitro Gene Transformation by a Soluble DNA Carrier System," J. Biol. Chem. 262:4429-4432.
Wu et al., "A novel polymorphism of FcγRIIIa (CD16) alters receptor function and predisposes to autoimmune disease," J Clin Invst 100 :1059-1070, 1997.
Wu et al., "Multimerization of a chimeric anti-CD20 single-chain Fv-Fc fusion protein is mediated through variable domain exchange," Protein Engineering 14(2): 1025-1033 (2001).
Wu, A.M et al. (1999) "Designer Genes: Recombinant Antibody Fragments for Biological Imaging," Q. J. Nucl. Med. 44(3):268-283.
Wucherpfennig, K.W. et al. (2010) "Structural Biology of the T-Cell Receptor: Insights into Receptor Assembly, Ligand Recognition, and Initiation of Signaling," Cold Spring Harb. Perspect. Biol. 2(4): a005140; pp. 1-14.
Xie et al. (2005) "A New Format of Bispecific Antibody: Highly Efficient Heterodimerization, Expression and Tumor Cell Lysis," J. Immunol. Methods 296:95-101.
Xiong, D. et al. (2002) "Efficient Inhibition of Human B-Cell Lymphoma Xenografts with an Anti-CD20 x Anti-CD3 Bispecific Diabody," Cancer Lett. (2002) 177(1):29-39.
Xu et at., "Residue at position 331 in the IgG1 and IgG4 CH2 domains contributes to their differential ability to bind and activate complement," J Biol Chem 269 :3469-3474, 1994.
Yeung and Wittrup, "Quantitative screening of yeast surface-displayed polypeptide libraries by magnetic bead capture," Biotechnol Prog 18:212-220, 2002.
Zeidler et al., "The Fc-region of a new class of intact bispecific antibody mediates activation of accessory cells and NK cells and induces direct phagocytosis of tumour cells," British J Cancer 83:261-266, 2000.
Zeng, Y. et al. (2008) "A Ligand-Pseudoreceptor System Based on de novo Designed Peptides for the Generation of Adenoviral Vectors with Altered Tropism," J. Gene Med. 10:355-367.
Zhu, Z. . et al (1997) "Remodeling Domain Interfaces to Enhance Heterodimer Formation," Protein Sci. 6:781-788.
Zuckier et al., "Chimeric human-mouse IgG antibodies with shuffled constant region exons demonstrate that multiple domains contribute to in vivo half-life," Cancer Res 58 :3905-3908, 1998.

\* cited by examiner

Figure 9A: Day 2 Imaging Data (Vehicle):
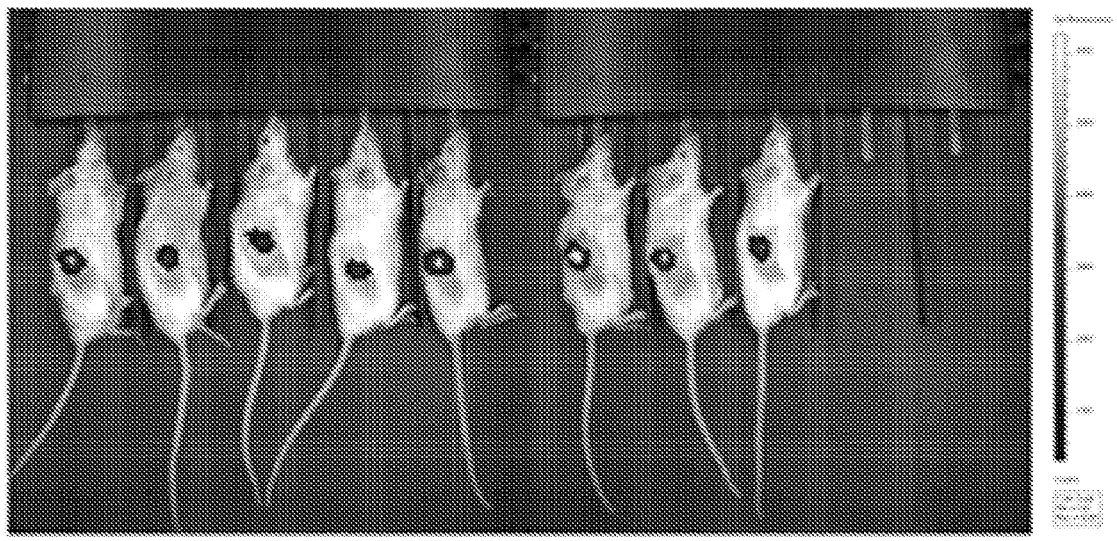
Figure 9B: Day 2 Imaging Data (gpA33 x CD3 DART-1 (0.5 mg/kg)):
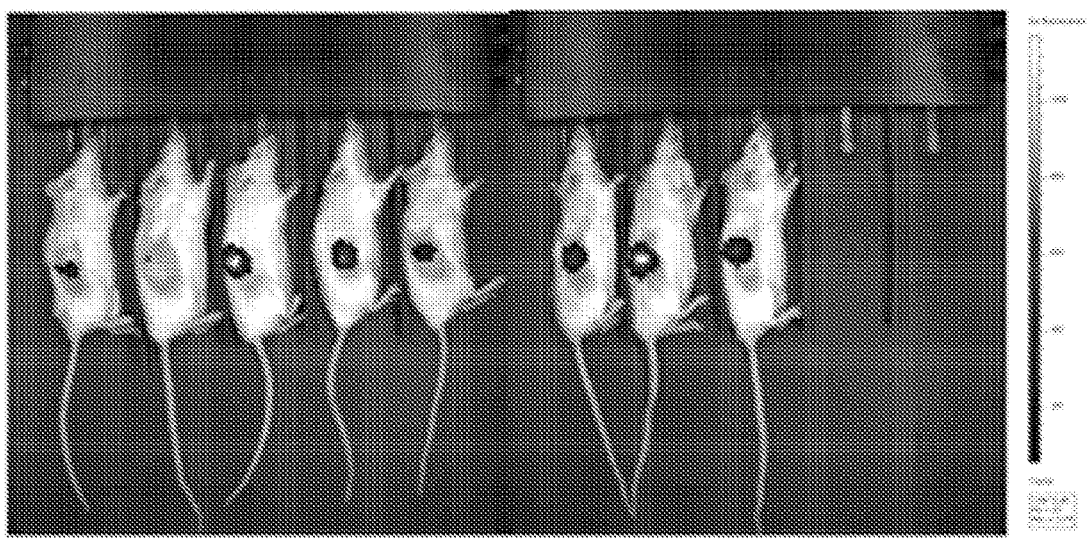

Figure 9C: Day 12 Imaging Data (Vehicle):
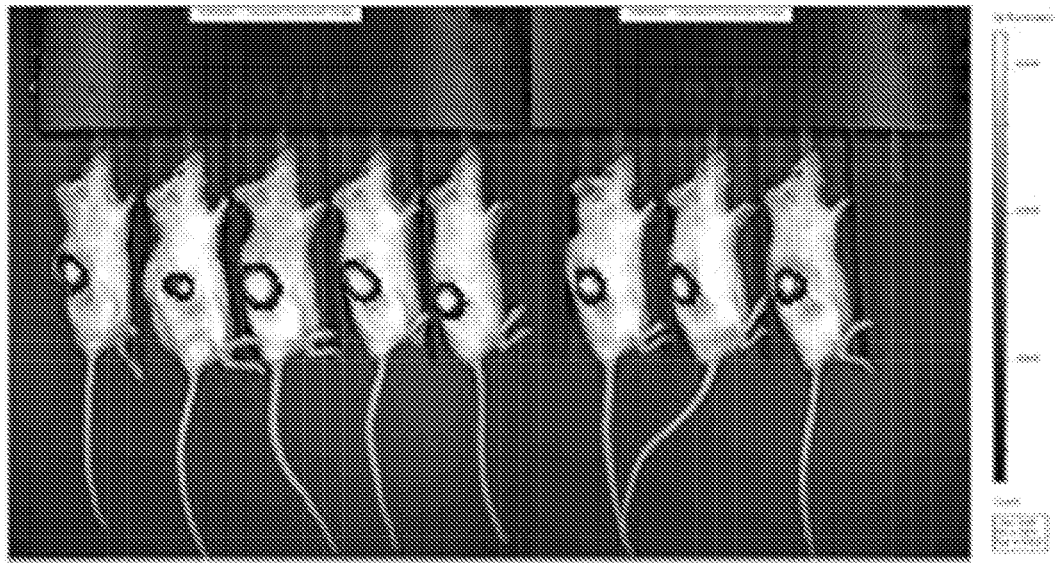
Figure 9D: Day 12 Imaging Data (gpA33 x CD3 DART-1 (0.5 mg/kg)):
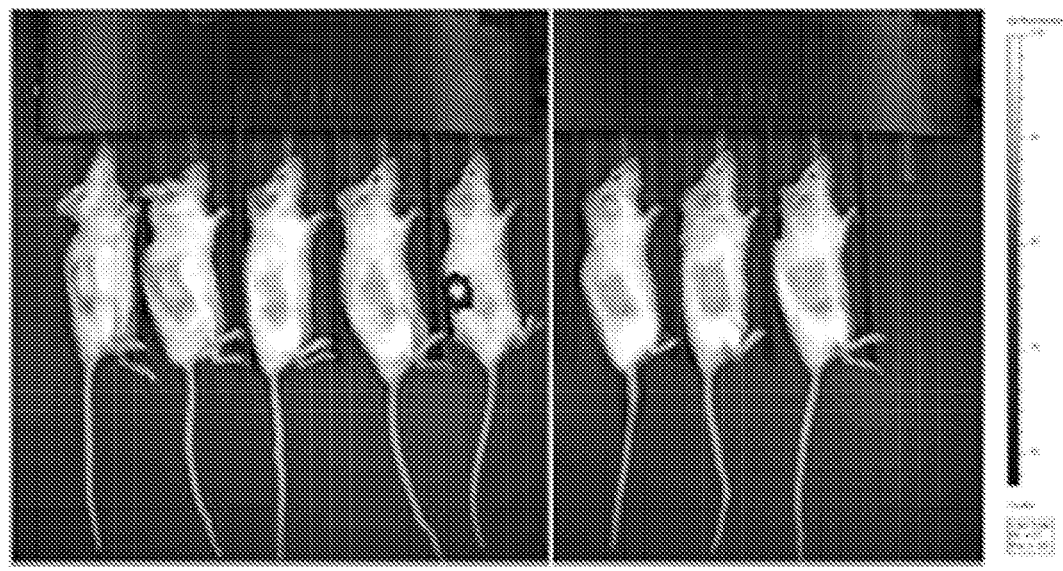

DART-2 w/Fc Version 1 Binding of Human CD3

DART-2 w/Fc Version 1 Binding of Cynomolgus CD3

DART-2 w/Fc Version 1 Binding of Human gpA33

DART-2 w/Fc Version 1 Binding of Cynomolgus gpA33

BI-SPECIFIC MONOVALENT DIABODIES THAT ARE CAPABLE OF BINDING TO GPA33 AND CD3, AND USES THEREOF

CROSS-REFERENCE TO RELATED APPLICATIONS

This Application is a § 371 National Stage Application of PCT/US2014/051793 (filed Aug. 20, 2014; pending) which application claims priority to U.S. Patent Applications No. 61/869,528 (filed on Aug. 23, 2013) and 61/907,691 (filed on Nov. 22, 2013), and to European Patent Application No. 13198859 (filed on Dec. 20, 2013), each of which applications is herein incorporated by reference in its entirety.

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entirety.

BACKGROUND OF THE INVENTION

Field of the Invention

The present invention is directed to bi-specific monovalent diabodies that comprise two polypeptide chains and which possess one binding site specific for an epitope of gpA33 and one binding site specific for an epitope of CD3 (i.e., a "gpA33×CD3 bi-specific monovalent diabody"). The present invention also is directed to bi-specific monovalent diabodies that comprise an immunoglobulin Fc Domain ("bi-specific monovalent Fc diabodies") and are composed of three polypeptide chains and which possess one binding site specific for an epitope of gpA33 and one binding site specific for an epitope of CD3 (i.e., a "gpA33×CD3 bi-specific monovalent Fc diabody"). The bi-specific monovalent diabodies and bi-specific monovalent Fc diabodies of the present invention are capable of simultaneous binding to gpA33 and CD3. The invention is directed to pharmaceutical compositions that contain such bi-specific monovalent diabodies or such bi-specific monovalent Fc diabodies. The invention is additionally directed to methods for the use of such diabodies in the treatment of cancer and other diseases and conditions.

Description of Related Art

I. gpA33

Colorectal cancer is among the most common malignancies of the Western world and is a leading cause of cancer deaths (Silverberg, E. et al. (1989) "*Cancer Statistics, 1989*," CA Cancer J Clin. 39(1):3-20). One potentially useful target for colon cancer is the 43 kD transmembrane glycoprotein A33 (gpA33) ((Heath, J. K. et al. (1997) "*The Human A33 Antigen Is A Transmembrane Glycoprotein And A Novel Member Of The Immunoglobulin Superfamily*," Proc. Natl. Acad. Sci. (U.S.A.) 94(2):469-474; Ritter, G. et al. (1997) "*Characterization Of Posttranslational Modifications Of Human A33 Antigen, A Novel Palmitoylated Surface Glycoprotein Of Human Gastrointestinal Epithelium*," Biochem. Biophys. Res. Commun. 236(3):682-686). gpA33 was first discovered through raising monoclonal murine antibodies against the human pancreatic carcinoma derived cell line ASPC1. One antibody (MAb A33) was found to react with a surface cell protein of 43 kDa, which was therefore designated "gpA33" (Wong, N. A. et al. (2006) "*EpCAM and gpA33 Are Markers Of Barrett's Metaplasia*," J. Clin. Pathol. 59(3):260-263).

gpA33 is a transmembrane protein of the junctional adhesion molecule family; Abud, H. E. et al. (2000) "*The Murine A33 Antigen Is Expressed At Two Distinct Sites During Development, The ICM Of The Blastocyst And The Intestinal Epithelium*," Mech. Dev. 98(1-2):111-114; Barendswaard, E. C. et al. (1998) "*Rapid And Specific Targeting Of Monoclonal Antibody A33 To A Colon Cancer Xenograft In Nude Mice*," Int. J. Oncol. 12(1):45-53; Panjideh, H. et al. (2008) "*Biodistribution And Efficacy Of [131I] A33scFv:: CDy, A Recombinant Antibody-Enzyme Protein For Colon Cancer*," Int. J. Oncol. 32(4):925-930). Although the functional significance of the A33 antigen is not yet understood, it has been shown to mediate colonic mucosal repair in an animal model of colitis and is homogeneously expressed in >95% of all colorectal carcinomas. A33 expression is uniform across both disease stage and degree of histological differentiation, and the antigen is not detectably secreted or shed into the blood stream (Infante, J. R. et al. (2013) "*Safety, Pharmacokinetics And Pharmacodynamics Of The Anti-A33 Fully-Human Monoclonal Antibody, KRN330, In Patients With Advanced Colorectal Cancer*," Eur. J. Cancer. 49(6):1169-1175; Panjideh, H. et al. (2008) "*Biodistribution And Efficacy Of [131I] A33scFv::CDy, A Recombinant Antibody-Enzyme Protein For Colon Cancer*," Int. J. Oncol. 32(4):925-930). Conversely, only a few instances of non-gastrointestinal A33 antigen expression have been identified (Johnstone, C. N. et al. (2000) "*Characterization Of Mouse A33 Antigen, A Definitive Marker For Basolateral Surfaces Of Intestinal Epithelial Cells*," Am. J. Physiol. Gastrointest. Liver Physiol. 279(3):G500-G510).

In light of the highly restricted expression of the A33 antigen, researchers have explored the possibility of treating A33-associated cancers with antibodies (Infante, J. R. et al. (2013) "*Safety, Pharmacokinetics And Pharmacodynamics Of The Anti-A33 Fully-Human Monoclonal Antibody, KRN330, In Patients With Advanced Colorectal Cancer*," Eur. J. Cancer. 49(6):1169-1175; Ackerman, M. E. et al. (2008) "*A33 Antigen Displays Persistent Surface Expression*," Cancer Immunol. Immunother. 57(7):1017-1027; Barendswaard, E. C. et al. (2001) "*Relative Therapeutic Efficacy Of (125)I-And (131)I-Labeled Monoclonal Antibody A33 In A Human Colon Cancer Xenograft*," J. Nucl. Med. 42(8):1251-1256; Carrasquillo, J. A. et al. (2011) "*(124)I-huA33 Antibody PET Of Colorectal Cancer*," J. Nucl. Med. 52(8):1173-1180; Chong, G. et al. (2005) "*Phase I Trial Of 131I-HuA33 In Patients With Advanced Colorectal Carcinoma*," Clin. Cancer Res. 11(13):4818-4826; Deckert, P. M. et al. (2000) "*Pharmacokinetics And Microdistribution Of Polyethylene Glycol-Modified Humanized A33 Antibody Targeting Colon Cancer Xenografts*," Int. J. Cancer. 87(3): 382-390; Johnston, A. P. et al. (2012) "*Targeting Cancer Cells: Controlling The Binding And Internalization Of Antibody-Functionalized Capsules*" ACS Nano. 6(8):6667-6674; Koppe, M. J. et al. (2005) "*Radioimmunotherapy And Colorectal Cancer*," Br. J. Surg. March; 92(3):264-276; Sakamoto, J. et al. (2006) "*A Phase I Radioimmunolocalization Trial Of Humanized Monoclonal Antibody HuA33 In Patients With Gastric Carcinoma*," Cancer Sci. 97(11): 1248-1254; Scott, A. M. et al. (2005) "*A Phase I Trial Of Humanized Monoclonal Antibody A33 In Patients With Colorectal Carcinoma: Biodistribution, Pharmacokinetics, And Quantitative Tumor Uptake*," Clin. Cancer Res. 11(13): 4810-4817; Tschmelitsch, J. et al. (1997) "*Enhanced Antitumor Activity Of Combination Radioimmunotherapy ($^{131}$I-Labeled Monoclonal Antibody A33) With Chemotherapy*

(*Fluorouracil*)," Cancer Res. 57(11):2181-2186). Likewise fragments of such antibodies have also been evaluated for their potential therapeutic role (Coelho, V. et al. (2007) "*Design, Construction, And In Vitro Analysis Of A33scFv:: CDy, A Recombinant Fusion Protein For Antibody-Directed Enzyme Prodrug Therapy In Colon Cancer*," Int. J. Oncol. 31(4):951-957).

II. CD3

CD3 is a T cell co-receptor composed of four distinct chains (Wucherpfennig, K. W. et al. (2010) "*Structural Biology Of The T-Cell Receptor: Insights Into Receptor Assembly, Ligand Recognition, And Initiation Of Signaling*," Cold Spring Harb. Perspect. Biol. 2(4):a005140; pages 1-14; Chetty, R. et al. (1994) "*CD3: Structure, Function And The Role Of Immunostaining In Clinical Practice*," J. Pathol. 173:303-307).

In mammals, the CD3 complex contains a CD3γ chain, a CD3δ chain, and two CD3ε chains. These chains associate with a molecule known as the T cell receptor (TCR) in order to generate an activation signal in T lymphocytes. In the absence of CD3, TCRs do not assemble properly and are degraded (Thomas, S. et al. (2010) "*Molecular Immunology Lessons From Therapeutic T-Cell Receptor Gene Transfer*," Immunology 129(2):170-177). CD3 is found bound to the membranes of all mature T cells, and in virtually no other cell type (see, Janeway, C. A. et al. (2005) In: IMMUNOBIOLOGY: THE IMMUNE SYSTEM IN HEALTH AND DISEASE," 6th ed. Garland Science Publishing, NY, pp. 214-216; Sun, Z. J. et al. (2001) "*Mechanisms Contributing To T Cell Receptor Signaling And Assembly Revealed By The Solution Structure Of An Ectodomain Fragment Of The CD3ε:γ Heterodimer*," Cell 105(7):913-923; Kuhns, M. S. et al. (2006) "*Deconstructing The Form And Function Of The TCR/CD3 Complex*," Immunity. 2006 February; 24(2):133-139).

III. Bi-Specific Diabodies

The ability of an intact, unmodified antibody (e.g., an IgG) to bind an epitope of an antigen depends upon the presence of variable domains on the immunoglobulin light and heavy chains (i.e., the VL and VH domains, respectively). The design of a diabody is based on the single chain Fv construct (scFv) (see, e.g., Holliger et al. (1993) "'*Diabodies': Small Bivalent And Bispecific Antibody Fragments*," Proc. Natl. Acad. Sci. (U.S.A) 90:6444-6448; US Patent Publication No. 2004/0058400 (Holliger et al.); US 2004/0220388 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672; WO 02/02781 (Mertens et al.); Olafsen, T. et al. (2004) "*Covalent Disulfide-Linked Anti-CEA Diabody Allows Site-Specific Conjugation And Radiolabeling For Tumor Targeting Applications*," Protein Eng. Des Sel. 17(1):21-27; Wu, A. et al. (2001) "*Multimerization Of A Chimeric Anti-CD20 Single Chain Fv-Fc Fusion Protein Is Mediated Through Variable Domain Exchange*," Protein Engineering 14(2):1025-1033; Asano et al. (2004) "*A Diabody For Cancer Immunotherapy And Its Functional Enhancement By Fusion Of Human Fc Region*," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8):583-588; Baeuerle, P. A. et al. (2009) "*Bispecific T-Cell Engaging Antibodies For Cancer Therapy*," Cancer Res. 69(12):4941-4944).

Interaction of an antibody light chain and an antibody heavy chain and, in particular, interaction of its VL and VH domains forms one of the epitope binding sites of the antibody. In contrast, the scFv construct comprises a VL and VH Domain of an antibody contained in a single polypeptide chain wherein the domains are separated by a flexible linker of sufficient length to allow self-assembly of the two domains into a functional epitope binding site. Where self-assembly of the VL and VH domains is rendered impossible due to a linker of insufficient length (less than about 12 amino acid residues), two of the scFv constructs interact with one another other to form a bivalent molecule in which the VL of one chain associates with the VH of the other (reviewed in Marvin et al. (2005) "*Recombinant Approaches To IgG-Like Bispecific Antibodies*," Acta Pharmacol. Sin. 26:649-658).

Natural antibodies are capable of binding to only one epitope species (i.e., mono-specific), although they can bind multiple copies of that species (i.e., exhibiting bi-valency or multi-valency). The art has noted the capability to produce diabodies that differ from such natural antibodies in being capable of binding two or more different epitope species (i.e., exhibiting bi-specificity or multispecificity in addition to bi-valency or multi-valency) (see, e.g., Holliger et al. (1993) "'*Diabodies': Small Bivalent And Bispecific Antibody Fragments,*" Proc. Natl. Acad. Sci. (U.S.A.) 90:6444-6448; US 2004/0058400 (Holliger et al.); US 2004/0220388 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672; WO 02/02781 (Mertens et al.); Mertens, N. et al., "*New Recombinant Bi- and Trispecific Antibody Derivatives,*" In: NOVEL FRONTIERS IN THE PRODUCTION OF COMPOUNDS FOR BIOMEDICAL USE, A. VanBroekhoven et al. (Eds.), Kluwer Academic Publishers, Dordrecht, The Netherlands (2001), pages 195-208; Wu, A. et al. (2001) "*Multimerization Of A Chimeric Anti-CD20 Single Chain Fv-Fc Fusion Protein Is Mediated Through Variable Domain Exchange*," Protein Engineering 14(2):1025-1033; Asano et al. (2004) "*A Diabody For Cancer Immunotherapy And Its Functional Enhancement By Fusion Of Human Fc Region*," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8):583-588; Baeuerle, P. A. et al. (2009) "*Bispecific T-Cell Engaging Antibodies For Cancer Therapy*," Cancer Res. 69(12):4941-4944).

The provision of non-monospecific diabodies provides a significant advantage: the capacity to co-ligate and co-localize cells that express different epitopes. Bivalent diabodies thus have wide-ranging applications including therapy and immunodiagnosis. Bi-valency allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the field of tumor imaging (Fitzgerald et al. (1997) "*Improved Tumour Targeting By Disulphide Stabilized Diabodies Expressed In Pichia pastoris*," Protein Eng. 10:1221). Of particular importance is the co-ligating of differing cells, for example, the cross-linking of cytotoxic T cells to tumor cells (Staerz et al. (1985) "*Hybrid Antibodies Can Target Sites For Attack By T Cells*," Nature 314:628-

631, and Holliger et al. (1996) "*Specific Killing Of Lymphoma Cells By Cytotoxic T-Cells Mediated By A Bispecific Diabody*," Protein Eng. 9:299-305).

Diabody epitope binding domains may also be directed to a surface determinant of any immune effector cell such as CD3, CD16, CD32, or CD64, which are expressed on T lymphocytes, natural killer (NK) cells or other mononuclear cells. In many studies, diabody binding to effector cell determinants, e.g., Fcγ receptors (FcγR), was also found to activate the effector cell (Holliger et al. (1996) "*Specific Killing Of Lymphoma Cells By Cytotoxic T-Cells Mediated By A Bispecific Diabody*," Protein Eng. 9:299-305; Holliger et al. (1999) "*Carcinoembryonic Antigen (CEA)-Specific T-cell Activation In Colon Carcinoma Induced By Anti-CD3×Anti-CEA Bispecific Diabodies And B7×Anti-CEA Bispecific Fusion Proteins*," Cancer Res. 59:2909-2916; WO 2006/113665; WO 2008/157379; WO 2010/080538; WO 2012/018687; WO 2012/162068). Normally, effector cell activation is triggered by the binding of an antigen bound antibody to an effector cell via Fc-FcγR interaction; thus, in this regard, diabody molecules of the invention may exhibit Ig-like functionality independent of whether they comprise an Fc Domain (e.g., as assayed in any effector function assay known in the art or exemplified herein (e.g., ADCC assay)). By cross-linking tumor and effector cells, the diabody not only brings the effector cell within the proximity of the tumor cells but leads to effective tumor killing (see e.g., Cao et al. (2003) "*Bispecific Antibody Conjugates In Therapeutics*," Adv. Drug. Deliv. Rev. 55:171-197).

However, the above advantages come at salient cost. The formation of such non-monospecific diabodies requires the successful assembly of two or more distinct and different polypeptides (i.e., such formation requires that the diabodies be formed through the heterodimerization of different polypeptide chain species). This fact is in contrast to monospecific diabodies, which are formed through the homodimerization of identical polypeptide chains. Because at least two dissimilar polypeptides (i.e., two polypeptide species) must be provided in order to form a non-monospecific diabody, and because homodimerization of such polypeptides leads to inactive molecules (Takemura, S. et al. (2000) "*Construction Of A Diabody (Small Recombinant Bispecific Antibody) Using A Refolding System*," Protein Eng. 13(8): 583-588), the production of such polypeptides must be accomplished in such a way as to prevent covalent bonding between polypeptides of the same species (Takemura, S. et al. (2000) "*Construction Of A Diabody (Small Recombinant Bispecific Antibody) Using A Refolding System*," Protein Eng. 13(8):583-588). The art has therefore taught the non-covalent association of such polypeptides (see, e.g., Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27; Asano et al. (2004) "*A Diabody For Cancer Immunotherapy And Its Functional Enhancement By Fusion Of Human Fc Region*," Abstract 3P-683, J. Biochem. 76(8): 992; Takemura, S. et al. (2000) "*Construction Of A Diabody (Small Recombinant Bispecific Antibody) Using A Refolding System*," Protein Eng. 13(8):583-588; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

However, the art has recognized that bi-specific monovalent diabodies composed of non-covalently-associated polypeptides are unstable and readily dissociate into non-functional monomers (see, e.g., Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

In the face of this challenge, the art has succeeded in developing stable, covalently bonded heterodimeric non-monospecific diabodies (see, e.g., WO 2006/113665; WO/2008/157379; WO 2010/080538; WO 2012/018687; WO/2012/162068; Johnson, S. et al. (2010) "*Effector Cell Recruitment With Novel Fv-Based Dual-Affinity Re-Targeting Protein Leads To Potent Tumor Cytolysis And In Vivo B-Cell Depletion*," J. Molec. Biol. 399(3):436-449; Veri, M. C. et al. (2010) "*Therapeutic Control Of B Cell Activation Via Recruitment Of Fcgamma Receptor IIb (CD32B) Inhibitory Function With A Novel Bispecific Antibody Scaffold*," Arthritis Rheum. 62(7):1933-1943; Moore, P. A. et al. (2011) "*Application Of Dual Affinity Retargeting Molecules To Achieve Optimal Redirected T-Cell Killing Of B-Cell Lymphoma*," Blood 117(17):4542-4551; US Patent Publications No. 2012/0294796 and 2013/0149236). Such approaches involve engineering one or more cysteine residues into each of the employed polypeptide species. For example, the addition of a cysteine residue to the C-terminus of such constructs has been shown to allow disulfide bonding between the polypeptide chains, stabilizing the resulting heterodimer without interfering with the binding characteristics of the bivalent molecule.

Diabodies and other immunoglobulins have been described purporting to have specificity for either or both of gpA33 and CD3 (see, e.g., US Patent Publications No. 2012/0014957; 2012/0034160; 2012/0087858; 2012/0189541; 2012/0195900; 2012/0201746; 2012/0237442; 2012/0263722; 2012/0258108; and 2012/0276608).

Notwithstanding such success, the production of stable, functional heterodimeric, non-monospecific diabodies can be further improved by the careful consideration and placement of the domains employed in the polypeptide chains. The present invention is thus directed to the provision of specific polypeptides that are particularly designed to form, via covalent bonding, heterodimeric diabodies and heterodimeric Fc diabodies that are capable of simultaneously binding gpA33 and CD3.

SUMMARY OF THE INVENTION

The invention is directed to "gpA33×CD3 bi-specific monovalent diabodies." In particular embodiments, the diabodies of the present invention further have a domain of an immunoglobulin Fc region (i.e., an "Fc Domain") ("gpA33×CD3 bi-specific monovalent Fc diabodies") or an Albumin-Binding Domain ("ABD") ("gpA33×CD3 bi-specific monovalent diabodies with ABD") to extend half-life in vivo. The gpA33×CD3 bi-specific monovalent diabodies of the invention and the gpA33×CD3 bi-specific monovalent Fc diabodies of the invention comprise two different polypeptide chains that associate with one another in a heterodimeric manner to form one binding site specific for an epitope of gpA33 and one binding site specific for an epitope of CD3. The gpA33×CD3 bi-specific monovalent diabodies and gpA33×CD3 bi-specific monovalent Fc diabodies of the invention are thus monovalent in that they are capable of binding to only one copy of an epitope of gpA33 and to only one copy of an epitope of CD3, but bi-specific in that a single diabody is able to bind simultaneously to the epitope of gpA33 and to the epitope of CD3.

The gpA33×CD3 bi-specific monovalent diabodies of the invention are composed of two polypeptide chains (a "first" and a "second" polypeptide chain), which are covalently bonded to one another, for example by disulfide bonding of cysteine residues located within each polypeptide chain. The gpA33×CD3 bi-specific monovalent Fc diabodies of the invention are composed of three polypeptide chains (a "first," "second" and "third" polypeptide chain), wherein the first and second polypeptide chains are covalently bonded to one another and the first and third polypeptide chains are covalently bonded to one another. The bi-specific monovalent diabodies and bi-specific monovalent Fc diabodies of the present invention are capable of simultaneous binding to gpA33 and CD3. The invention is directed to such gpA33×CD3 bi-specific monovalent diabodies and bi-specific monovalent gpA33×CD3 Fc diabodies, and to pharmaceutical compositions that contain such bi-specific monovalent diabodies or such bi-specific monovalent Fc diabodies. The invention is additionally directed to methods for the use of such diabodies in the treatment of cancer and other diseases and conditions.

In detail, the invention provides a bi-specific monovalent diabody, wherein the bi-specific monovalent diabody is capable of specific binding to an epitope of gpA33 and to an epitope of CD3, wherein the bi-specific monovalent diabody comprises a first polypeptide chain and a second polypeptide chain, wherein the first and second polypeptide chains are covalently bonded to one another, and wherein:

A. the first polypeptide chain comprises, in the N-terminal to C-terminal direction:
  i. a Domain 1, comprising a sub-Domain (1A), which comprises a VL Domain of a monoclonal antibody capable of binding to CD3 ($VL_{CD3}$) (SEQ ID NO:5); and a sub-Domain (1B), which comprises a VH Domain of a monoclonal antibody capable of binding to gpA33 ($VH_{gpA33}$) (SEQ ID NO:27); wherein the sub-Domains (1A) and (1B) are separated from one another by a peptide linker (SEQ ID NO:1);
  ii. a Domain 2, wherein the Domain 2 is a K-coil Domain (SEQ ID NO:4) or an E-coil Domain (SEQ ID NO:3), wherein the Domain 2 is separated from the Domain 1 by a peptide linker (SEQ ID NO:2);
B. the second polypeptide chain comprises, in the N-terminal to C-terminal direction:
  i. a Domain 1, comprising a sub-Domain (1A), which comprises a VL Domain of a monoclonal antibody capable of binding to gpA33 ($VL_{gpA33}$) (SEQ ID NO:26) and a sub-Domain (1B), which comprises a VH Domain of a monoclonal antibody capable of binding to CD3 ($VH_{CD3}$) (SEQ ID NO:25), wherein the sub-Domains (1A) and (1B) are separated from one another by a peptide linker (SEQ ID NO:1);
  ii. a Domain 2, wherein the Domain 2 is an E-coil Domain (SEQ ID NO:3) or a K-coil Domain (SEQ ID NO:4), wherein the Domain 2 is separated from the Domain 1 by a peptide linker (SEQ ID NO:2); and wherein the Domain 2 of the first polypeptide chain and the Domain 2 of the second polypeptide chain are not both E-coil Domains or both K-coil Domains;

and wherein:
(a) the VL Domain of the first polypeptide chain and the VH Domain of the second polypeptide chain form an Antigen Binding Domain capable of specific binding to an epitope of CD3; and
(b) the VH Domain of the first polypeptide chain and the VL Domain of the second polypeptide chain form an Antigen Binding Domain capable of specific binding to an epitope of gpA33.

The invention additionally concerns the embodiment of the above-described bi-specific monovalent diabody wherein the first polypeptide chain or the second polypeptide chain comprises, an Albumin-Binding Domain (SEQ ID NO:34), linked C-terminally to Domain 2 or N-terminally to Domain 1A via a Linker 3 (SEQ ID NO:32).

The invention additionally concerns a bi-specific monovalent Fc diabody, wherein the bi-specific monovalent Fc diabody is capable of specific binding to an epitope of gpA33 and to an epitope of CD3, and possesses an IgG Fc Domain, wherein the bi-specific monovalent Fc diabody comprises a first polypeptide chain, a second polypeptide chain and a third polypeptide chain, wherein the first and second polypeptide chains are covalently bonded to one another and the first and third polypeptide chains are covalently bonded to one another, and wherein:

A. the first polypeptide chain comprises, in the N-terminal to C-terminal direction:
  i. a Domain 1, comprising a sub-Domain (1A), which comprises a VL Domain of a monoclonal antibody capable of binding to gpA33 ($VL_{gpA33}$) (SEQ ID NO:26) and a sub-Domain (1B), which comprises a VH Domain of a monoclonal antibody capable of binding to CD3 ($VH_{CD3}$) (SEQ ID NO:25), wherein the sub-Domains (1A) and (1B) are separated from one another by a peptide linker (SEQ ID NO:1);
  ii. a Domain 2, wherein the Domain 2 is an E-coil Domain (SEQ ID NO:3) or a K-coil Domain (SEQ ID NO:4), wherein the Domain 2 is separated from the Domain 1 by a peptide linker (SEQ ID NO:2); and
  iii. a Domain 3, comprising a sub-Domain (3A), which comprises a cysteine-containing peptide (Peptide 1) (SEQ ID NO:39) and a sub-Domain (3B), which comprises a polypeptide portion of an IgG Fc Domain having CH2 and CH3 domains of an IgG immunoglobulin Fc Domain; wherein the Domains 3 and 2 are separated from one another by a spacer peptide (Linker 5) (GGG);
B. the second polypeptide chain comprises, in the N-terminal to C-terminal direction:
  i. a Domain 1, comprising a sub-Domain (1A), which comprises a VL Domain of a monoclonal antibody capable of binding to CD3 ($VL_{CD3}$) (SEQ ID NO:5), and a sub-Domain (1B), which comprises a VH Domain of a monoclonal antibody capable of binding to gpA33 ($VH_{gpA33}$) (SEQ ID NO:27); wherein the sub-Domains (1A) and (1B) are separated from one another by a peptide linker (SEQ ID NO:1);
  ii. a Domain 2, wherein the Domain 2 is a K-coil Domain (SEQ ID NO:4) or an E-coil Domain (SEQ ID NO:3), wherein the Domain 2 is separated from the Domain 1 by a peptide linker (SEQ ID NO:2); and wherein the Domain 2 of the first polypeptide chain and the Domain 2 of the second polypeptide chain are not both E-coil Domains or both K-coil Domains; and
C. the third polypeptide chain comprises, in the N-terminal to C-terminal direction, a Domain 3 comprising:
  (1) a sub-Domain (3A), which comprises a cysteine-containing peptide (Peptide 1) (SEQ ID NO:39); and
  (2) a sub-Domain (3B), which comprises a polypeptide portion of an IgG Fc Domain having CH2 and CH3 domains of an IgG immunoglobulin Fc Domain;

and wherein:
(a) the polypeptide portions of the IgG Fc domains of the first and third polypeptide chain form the IgG Fc Domain;
(b) the VL Domain of the first polypeptide chain and the VH Domain of the second polypeptide chain form an Antigen Binding Domain capable of specific binding to an epitope of CD3; and
(c) the VH Domain of the first polypeptide chain and the VL Domain of the second polypeptide chain form an Antigen Binding Domain capable of specific binding to an epitope of gpA33.

The invention additionally concerns a bi-specific monovalent Fc diabody, wherein the bi-specific monovalent Fc diabody is capable of specific binding to an epitope of gpA33 and to an epitope of CD3, and possesses an IgG Fc Domain, wherein the bi-specific monovalent Fc diabody comprises a first polypeptide chain, a second polypeptide chain and a third polypeptide chain, wherein the first and second polypeptide chains are covalently bonded to one another and the first and third polypeptide chains are covalently bonded to one another, and wherein:
A. the first polypeptide chain comprises, in the N-terminal to C-terminal direction:
  i. a Domain 3, comprising a sub-Domain (3A), which comprises a cysteine-containing peptide (Peptide 1) (SEQ ID NO:39) and a sub-Domain (3B), which comprises a polypeptide portion of an IgG Fc Domain having CH2 and CH3 domains of an IgG immunoglobulin Fc Domain;
  ii. a Domain 1, comprising a sub-Domain (1A), which comprises a VL Domain of a monoclonal antibody capable of binding to gpA33 (VL$_{gpA33}$) (SEQ ID NO:26) and a sub-Domain (1B), which comprises a VH Domain of a monoclonal antibody capable of binding to CD3 (VH$_{CD3}$) (SEQ ID NO:25), wherein the sub-Domains (1A) and (1B) are separated from one another by a peptide linker (SEQ ID NO:1); wherein the Domains 1 and 3 are separated from one another by a spacer peptide (Linker 4) (SEQ ID NO:38);
  iii. a Domain 2, wherein the Domain 2 is an E-coil Domain (SEQ ID NO:3) or a K-coil Domain (SEQ ID NO:4), wherein the Domain 2 is separated from the Domain 1 by a peptide linker (SEQ ID NO:2); and
B. the second polypeptide chain comprises, in the N-terminal to C-terminal direction:
  i. a Domain 1, comprising a sub-Domain (1A), which comprises a VL Domain of a monoclonal antibody capable of binding to CD3 (VL$_{CD3}$) (SEQ ID NO:5); and a sub-Domain (1B), which comprises a VH Domain of a monoclonal antibody capable of binding to gpA33 (VH$_{gpA33}$) (SEQ ID NO:27); wherein the sub-Domains (1A) and (1B) are separated from one another by a peptide linker (SEQ ID NO:1);
  ii. a Domain 2, wherein the Domain 2 is a K-coil Domain (SEQ ID NO:4) or an E-coil Domain (SEQ ID NO:3), wherein the Domain 2 is separated from the Domain 1 by a peptide linker (SEQ ID NO:2); and wherein the Domain 2 of the first polypeptide chain and the Domain 2 of the second polypeptide chain are not both E-coil Domains or both K-coil Domains; and
C. the third polypeptide chain comprises, in the N-terminal to C-terminal direction, a Domain 3 comprising:
  (1) a sub-Domain (3A), which comprises a cysteine-containing peptide (Peptide 1) (SEQ ID NO:39); and
  (2) a sub-Domain (3B), which comprises a polypeptide portion of an IgG Fc Domain having CH2 and CH3 domains of an IgG immunoglobulin Fc Domain;

and wherein:
(a) the polypeptide portions of the IgG Fc domains of the first and third polypeptide chain form the IgG Fc Domain;
(b) the VL Domain of the first polypeptide chain and the VH Domain of the second polypeptide chain form an Antigen Binding Domain capable of specific binding to an epitope of CD3; and
(c) the VH Domain of the first polypeptide chain and the VL Domain of the second polypeptide chain form an Antigen Binding Domain capable of specific binding to an epitope of gpA33.

The invention further concerns the embodiments of any of the above-described bi-specific monovalent Fc diabodies wherein the sub-Domain (3B) of the first polypeptide chain comprises a sequence different from that of the sub-Domain (3B) of the third polypeptide chain.

The invention further concerns the embodiments of such above-described bi-specific monovalent Fc diabodies wherein the sub-Domain (3B) of the first polypeptide chain has the amino acid sequence of SEQ ID NO:40, and the sub-Domain (3B) of the third polypeptide chain has the amino acid sequence of SEQ ID NO:41.

The invention further concerns the embodiments of such above-described bi-specific monovalent Fc diabodies wherein the sub-Domain (3B) of the first polypeptide chain has the amino acid sequence of SEQ ID NO:41, and the sub-Domain (3B) of the third polypeptide chain has the amino acid sequence of SEQ ID NO:40.

The invention further concerns the embodiments of such above-described bi-specific monovalent Fc diabodies wherein the Domain 3 of the first polypeptide chain and/or the Domain 3 of the third polypeptide chain comprises a variant CH2-CH3 sequence that exhibits altered binding to an Fcγ receptor.

The invention further concerns the embodiments of any of the above-described bi-specific monovalent diabodies or of any of the above-described bi-specific monovalent Fc diabodies, wherein the Domain 2 of the first polypeptide chain comprises an E-coil (SEQ ID NO:3), and the Domain 2 of the second polypeptide chain comprises a K-coil (SEQ ID NO:4).

The invention further concerns the embodiments of any of the above-described bi-specific monovalent diabodies or of any of the above-described bi-specific monovalent Fc diabodies, wherein the Domain 2 of the first polypeptide chain comprises a K-coil (SEQ ID NO:4), and the Domain 2 of the second polypeptide chain comprises an E-coil (SEQ ID NO:3).

The invention further concerns a bi-specific monovalent diabody, wherein the bi-specific monovalent diabody is capable of specific binding to an epitope of CD3 and to an epitope of gpA33, wherein the bi-specific monovalent diabody comprises:
(1) a first polypeptide chain having the amino acid sequence of SEQ ID NO:28, and a second polypeptide chain having the amino acid sequence of SEQ ID NO:30; or
(2) a first polypeptide chain having the amino acid sequence of SEQ ID NO:35, and a second polypeptide chain having the amino acid sequence of SEQ ID NO:30;
wherein the first and the second polypeptide chains are covalently bonded to one another by a disulfide bond.

The invention further concerns a bi-specific monovalent Fc diabody, wherein the bi-specific monovalent Fc diabody is capable of specific binding to an epitope of CD3 and to an epitope of gpA33, and possesses an IgG Fc Domain, wherein the bi-specific monovalent Fc diabody comprises:

(1) a first polypeptide chain having the amino acid sequence of SEQ ID NO:42, a second polypeptide chain having the amino acid sequence of SEQ ID NO:44, and a third polypeptide chain having the amino acid sequence of SEQ ID NO:46; or
(2) a first polypeptide chain having the amino acid sequence of SEQ ID NO:48, a second polypeptide chain having the amino acid sequence of SEQ ID NO:28, and a third polypeptide chain having the amino acid sequence of SEQ ID NO:46;
wherein the first and the second polypeptide chains are covalently bonded to one another by a first disulfide bond and the first and third polypeptide chains are covalently bonded to one another by a second disulfide bond.

The invention further concerns a pharmaceutical composition comprising any of the above-described bi-specific monovalent diabodies or any of the above-described bi-specific monovalent Fc diabodies; and a physiologically acceptable carrier.

The invention further concerns the use of the above-described pharmaceutical composition in the treatment of a cancer characterized by the expression of gpA33, and especially such use wherein the cancer is colorectal cancer, colon cancer, gastric cancer or pancreatic cancer.

The invention further concerns a cell that expresses a polypeptide chain of any of the above-described bi-specific monovalent diabodies or any of the above-described bi-specific monovalent Fc diabodies, as well as a polynucleotide that encodes such expressed polypeptide.

The invention further concerns a cell that expresses an antibody or a polypeptide portion or fragment thereof, wherein the antibody binds to gpA33, and wherein the antibody or polypeptide portion or fragment thereof comprises:
(1) CDR1 (SEQ ID NO:14), CDR2 (SEQ ID NO:15) and CDR3 (SEQ ID NO:16) of a light chain of an anti-human gpA33 antibody;
(2) CDR1 (SEQ ID NO:18), CDR2 (SEQ ID NO:19) and CDR3 (SEQ ID NO:20) of a heavy chain of an anti-human gpA33 antibody; or
(3) both (1) and (2).

BRIEF DESCRIPTION OF THE DRAWINGS

FIGS. 5D-5F: CD4 T cells+colo205 cells (FIG. 5D), CD4 T cells+ASPC-1 cells (FIG. 5E), CD8 T cells alone (FIG. 5F).

FIGS. 9A-9D shows tumor imaging data of NOD scid gamma (NSG) mice implanted with Colo205 cells two days after receiving Vehicle (FIG. 9A) or the gpA33×CD3 bi-specific monovalent diabody (DART-1) (FIG. 9B), and 12 days after receiving Vehicle (FIG. 9C) or the DART-1 (FIG. 9D).

DETAILED DESCRIPTION OF THE INVENTION

Figure 1:
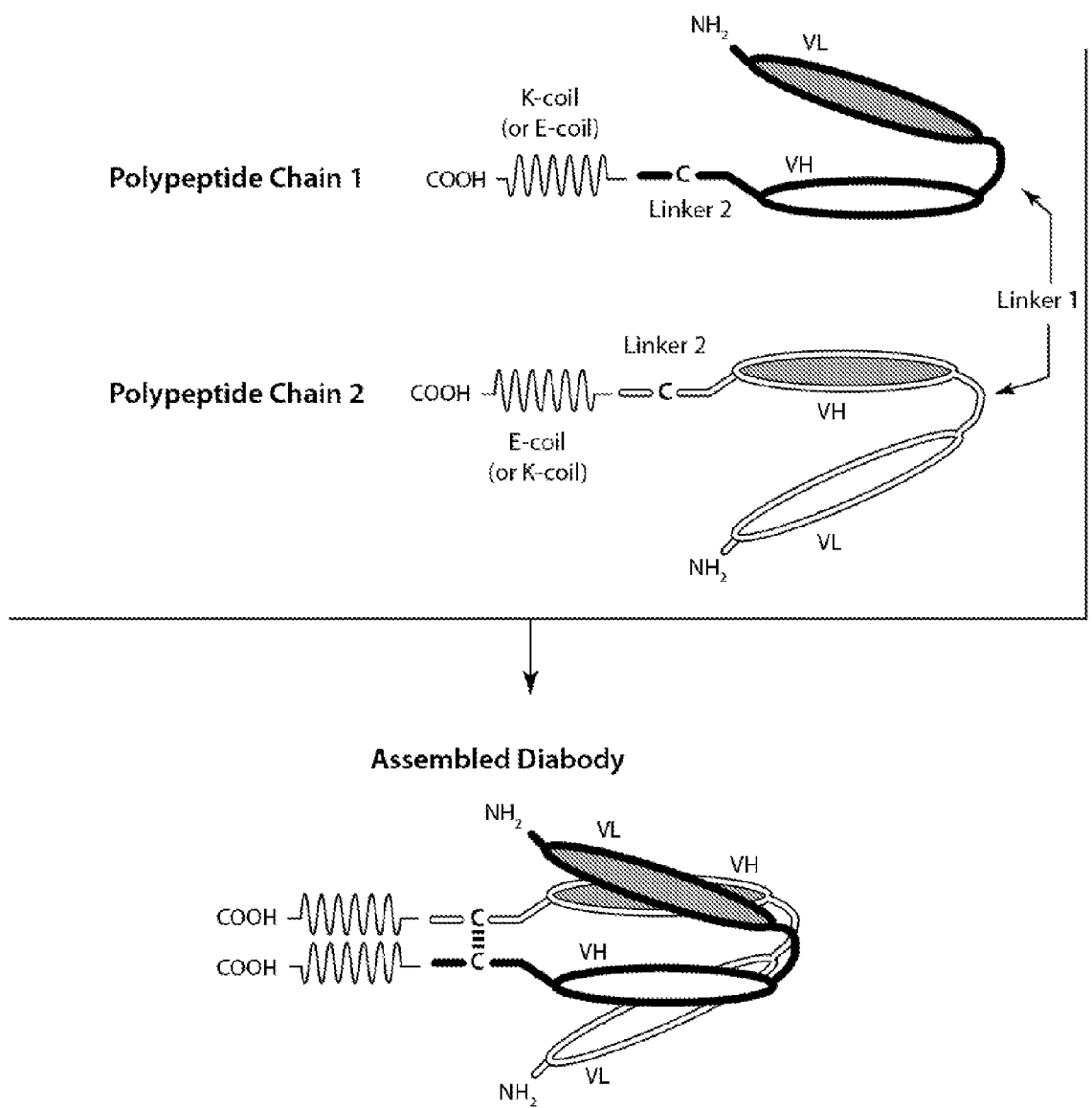
FIG. 1 illustrates the structures of the first and second polypeptide chains of a two chain gpA33×CD3 bi-specific monovalent diabody of the present invention.

The present invention is directed to bi-specific monovalent diabodies that comprise two polypeptide chains and which possess one binding site specific for an epitope of gpA33 and one binding site specific for an epitope of CD3 (i.e., a "gpA33×CD3 bi-specific monovalent diabody"). The present invention also is directed to bi-specific monovalent diabodies that comprise an immunoglobulin Fc Domain ("bi-specific monovalent Fc diabodies") and are composed of three polypeptide chains and which possess one binding site specific for an epitope of gpA33 and one binding site specific for an epitope of CD3 (i.e., a "gpA33×CD3 bi-specific monovalent Fc diabody"). The bi-specific monovalent diabodies and bi-specific monovalent Fc diabodies the present invention are capable of simultaneous binding to gpA33 and CD3. The invention is directed to pharmaceutical compositions that contain such bi-specific monovalent diabodies or such bi-specific monovalent Fc diabodies. The invention is additionally directed to methods for the use of such diabodies in the treatment of cancer and other diseases and conditions.

The gpA33×CD3 bi-specific monovalent diabodies of the present invention are composed of two polypeptide chains that associate with one another to form one binding site specific for an epitope of gpA33 and one binding site specific for an epitope of CD3. The individual polypeptide chains of the diabody are covalently bonded to one another, for example by disulfide bonding of cysteine residues located within each polypeptide chain. Each polypeptide chain contains an Antigen Binding Domain of a Light Chain Variable Domain, an Antigen Binding Domain of a Heavy Chain Variable Domain and a heterodimerization Domain. An intervening linker peptide (Linker 1) separates the Antigen Binding Domain of the Light Chain Variable Domain from the Antigen Binding Domain of the Heavy Chain Variable Domain. The Antigen Binding Domain of the Light Chain Variable Domain of the first polypeptide chain interacts with the Antigen Binding Domain of the Heavy Chain Variable Domain of the second polypeptide chain in order to form a first functional antigen binding site that is specific for the first antigen (i.e., either gpA33 or CD3). Likewise, the Antigen Binding Domain of the Light Chain Variable Domain of the second polypeptide chain interacts with the Antigen Binding Domain of the Heavy Chain Variable Domain of the first polypeptide chain in order to form a second functional antigen binding site that is specific for the second antigen (i.e., either gpA33 or CD3, depending upon the identity of the first antigen). Thus, the selection of the Antigen Binding Domain of the Light Chain Variable Domain and the Antigen Binding Domain of the Heavy Chain Variable Domain of the first and second polypeptide chains are coordinated, such that the two polypeptide chains collectively comprise Antigen Binding Domains of Light and Heavy Chain Variable Domains capable of binding to gpA33 and CD3.

The gpA33×CD3 bi-specific monovalent Fc diabodies of the present invention are composed of a first polypeptide chain, a second polypeptide chain and a third polypeptide chain. The first and second polypeptide chains associate with one another to form one binding site specific for an epitope of gpA33 and one binding site specific for an epitope of CD3. The first polypeptide chain and the third polypeptide chain associate with one another to form an immunoglobulin Fc Domain. The first and second polypeptide chains of the bi-specific monovalent Fc diabody are covalently bonded to one another, for example by disulfide bonding of cysteine residues located within each polypeptide chain. The first and third polypeptide chains are covalently bonded to one another, for example by disulfide bonding of cysteine residues located within each polypeptide chain. The first and second polypeptide chains each contain an Antigen Binding Domain of a Light Chain Variable Domain, an Antigen Binding Domain of a Heavy Chain Variable Domain and a heterodimerization Domain. An intervening linker peptide (Linker 1) separates the Antigen Binding Domain of the Light Chain Variable Domain from the Antigen Binding Domain of the Heavy Chain Variable Domain. The Antigen Binding Domain of the Light Chain Variable Domain of the first polypeptide chain interacts with the Antigen Binding Domain of the Heavy Chain Variable Domain of the second polypeptide chain in order to form a first functional antigen binding site that is specific for the first antigen (i.e., either gpA33 or CD3). Likewise, the Antigen Binding Domain of the Light Chain Variable Domain of the second polypeptide chain interacts with the Antigen Binding Domain of the Heavy Chain Variable Domain of the first polypeptide chain in order to form a second functional antigen binding site that is specific for the second antigen (i.e., either gpA33 or CD3, depending upon the identity of the first antigen). Thus, the selection of the Antigen Binding Domain of the Light Chain Variable Domain and the Antigen Binding Domain of the Heavy Chain Variable Domain of the first and second polypeptide chains are coordinated, such that the two polypeptide chains collectively comprise Antigen Binding Domains of light and Heavy Chain Variable Domains capable of binding to gpA33 and CD3. The first and third polypeptide chains each contain a cysteine-containing peptide (Peptide 1) SEQ ID NO:39: and some or all of the CH2 Domain and/or some or all of the CH3 Domain of a complete immunoglobulin Fc Domain and a cysteine-containing peptide. The some or all of the CH2 Domain and/or the some or all of the CH3 Domain associate to form the immunoglobulin Fc Domain of the bi-specific monovalent Fc diabodies of the present invention. The first and third polypeptide chains of the bi-specific monovalent Fc diabodies of the present invention are covalently bonded to one another, for example by disulfide bonding of cysteine residues located within the cysteine-containing peptide of the polypeptide chains.

The formation of heterodimers of the first and second polypeptide chains of the bi-specific monovalent diabody or bi-specific monovalent Fc diabody can be driven by the heterodimerization domains. Such domains include GVEPKSC (SEQ ID NO:54) (or VEPKSC; SEQ ID NO:55) on one polypeptide chain and GFNRGEC (SEQ ID NO:56) (or FNRGEC; SEQ ID NO:57) on the other polypeptide chain (US2007/0004909). Alternatively, such domains can be engineered to contain coils of opposing charges. The heterodimerization Domain of one of the polypeptide chains comprises a sequence of at least six, at least seven or at least eight positively charged amino acids, and the heterodimerization Domain of the other polypeptide chain comprises a sequence of at least six, at least seven or at least eight negatively charged amino acids. For example, the first or the second heterodimerization Domain may comprise a sequence comprising eight positively charged amino acids and the other of the heterodimerization domains may comprise a sequence comprising eight negatively charged amino acids. The positively charged amino acid may be lysine, arginine, histidine, etc. and/or the negatively charged amino acid may be glutamic acid, aspartic acid, etc. The positively charged amino acid is preferably lysine and/or the negatively charged amino acid is preferably glutamic acid.

The bi-specific monovalent diabodies and bi-specific monovalent Fc diabodies of the present invention are engineered so that such first and second polypeptide chains covalently bond to one another via cysteine residues along their length. Such cysteine residues may be introduced into the intervening linker that separates the VL and VH domains of the polypeptides. Alternatively, and more preferably, a second peptide (Linker 2) is introduced into each polypeptide chain, for example, at the amino-terminus of the polypeptide chains or at a position that places Linker 2 between the heterodimerization Domain and the Antigen Binding Domain of the Light Chain Variable Domain or Heavy Chain Variable Domain.

As indicated above, gpA33 is expressed by colorectal cells. Antibodies capable of immunospecifically binding to gpA33 are capable of binding to such cells. CD3 is expressed on T cells. Thus, antibodies capable of immunospecifically binding to both gpA33 and CD3 are capable of targeting T cells to colorectal and other cancer cells that express gpA33 (e.g., colon carcinoma cells, pancreatic cancer cells, etc.) and of thus providing an improved therapy for such cancers.

I. Preferred gpA33×CD3 Bi-Specific Monovalent Diabodies of the Present Invention A. gpA33×CD3 Bi-Specific Monovalent Diabodies One embodiment of the present invention relates to gpA33×CD3 bi-specific monovalent diabodies that are composed of a first polypeptide chain and a second polypeptide chain, whose sequences permit the polypeptide chains to covalently bind to each other to form a covalently-associated complex that is capable of simultaneously binding to both gpA33 and CD3.

The first polypeptide chain of preferred gpA33×CD3 bi-specific monovalent diabodies comprise, in the N-terminal to C-terminal direction, an N-terminus, the VL Domain of a monoclonal antibody capable of binding to either CD3 or gpA33 (i.e., either VL$_{CD3}$ or VL$_{gpA33}$), a first intervening spacer peptide (Linker 1), a VH Domain of a monoclonal antibody capable of binding to either gpA33 (if such first polypeptide chain contains VL$_{CD3}$) or CD3 (if such first polypeptide chain contains VL$_{gpA33}$), a cysteine-containing second intervening spacer peptide (Linker 2), a heterodimer-promoting Domain and a C-terminus (FIG. 1).

The second polypeptide chain of preferred gpA33×CD3 bi-specific monovalent diabodies comprises, in the N-terminal to C-terminal direction, an N-terminus, a VL Domain of a monoclonal antibody capable of binding to either gpA33 or CD3 (i.e., either VL$_{gpA33}$ or VL$_{CD3}$, depending upon the VL Domain selected for the first polypeptide chain of the diabody), an intervening linker peptide (Linker 1), a VH Domain of a monoclonal antibody capable of binding to either CD3 (if such second polypeptide chain contains VL$_{gpA33}$) or CD3 (if such second polypeptide chain contains VL$_{CD3}$), a cysteine-containing spacer peptide (Linker 2), a heterodimer-promoting Domain, and a C-terminus (FIG. 1).

The VL Domain of the first polypeptide chain of preferred gpA33×CD3 bi-specific monovalent diabodies interacts with the VH Domain of the second polypeptide chain of preferred gpA33×CD3 bi-specific monovalent diabodies in order to form a first functional antigen binding site that is specific for a first antigen (i.e., either CD3 or gpA33). Likewise, the VL Domain of the second polypeptide chain interacts with the VH Domain of the first polypeptide chain in order to form a second functional antigen binding site that is specific for a second antigen (i.e., either gpA33 or CD3, depending upon the identity of the first antigen). Thus, the selection of the VL and VH domains of the first and second polypeptide chains are coordinated, such that the two polypeptide chains of preferred gpA33×CD3 bi-specific monovalent diabodies collectively comprise VL and VH domains capable of binding to gpA33 and CD3 (i.e., they comprise VL$_{CD3}$/VH$_{CD3}$ and VL$_{gpA33}$/VH$_{gpA33}$).

Most preferably, the length of the intervening linker peptide (Linker 1, which separates such VL and VH domains) is selected to substantially or completely prevent the VL and VH domains of the polypeptide chain from binding to one another. Thus the VL and VH domains of the first polypeptide chain are substantially or completely incapable of binding to one another. Likewise, the VL and VH domains of the second polypeptide chain are substantially or completely incapable of binding to one another. A preferred intervening spacer peptide (Linker 1) has the sequence (SEQ ID NO:1): GGGSGGGG.

The cysteine-containing second intervening spacer peptide (Linker 2) will contain 1, 2, 3 or more cysteines. A preferred cysteine-containing spacer peptide (Linker 2) has the sequence is SEQ ID NO:2: GGCGGG.

The heterodimer-promoting domains of the first and second polypeptides differ from one another and are designed to associate with one another so as to promote association of the first and second polypeptide chains. Thus, in a preferred embodiment, one of these polypeptide chains will be engineered to contain a heterodimer-promoting "E-coil" Domain (SEQ ID NO:3):

EVAAL<u>E</u>KEVAAL<u>E</u>KEVAAL<u>E</u>KEVAAL<u>E</u>K whose residues will form a negative charge at pH 7, while the other of the two polypeptide chains will be engineered to contain a heterodimer-promoting "K-coil" Domain (SEQ ID NO:4):

KVAAL<u>KE</u>KVAAL<u>KE</u>KVAAL<u>KE</u>KVAAL<u>KE</u> whose residues will form a positive charge at pH 7. The presence of such charged domains promotes association between the first and second polypeptides, and thus fosters heterodimerization. It is immaterial which coil is provided to which chain, as long as the coils employed on the first and second polypeptide chains differ so as to foster heterodimerization between such chains.

1. The gpA33×CD3 Bi-Specific Monovalent Diabody, "DART-1"

The first and second polypeptide chains of a preferred gpA33×CD3 bi-specific monovalent diabody, designated herein as "DART-1" comprise polypeptide domains having the following sequences:

The VL Domain of an antibody that binds CD3 (VL$_{CD3}$) (SEQ ID NO:5):

QAVVTQEPSLTVSPGGTVTLTCRSSTGAVTTSNYANWVQQKPGQAPRGLI

GGTNKRAPWTPARFSGSLLGGKAALTITGAQAEDEADYYCALWYSNLWVF

GGGTKLTVLG

The Antigen Binding Domain of VL$_{CD3}$ comprises CDR1 having the sequence: (SEQ ID NO:6) RSST-GAVTTSNYAN; CDR2 having the sequence (SEQ ID NO:7): GTNKRAP; and CDR3 having the sequence (SEQ ID NO:8): ALWYSNLWV.

The VH Domain of an antibody that binds CD3 (VH$_{CD3}$) (SEQ ID NO:9):

EVQLVESGGGLVQPGGSLRLSCAASGFTFNTYAMNWVRQAPGKGLEWVAR

IRSKYNNYATYYADSVKDRFTISRDDSKNSLYLQMNSLKTEDTAVYYCVR

HGNFGNSYVSWFAYWGQGTLVTVSS

The Antigen Binding Domain of VH$_{CD3}$ comprises: CDR1 having the sequence (SEQ ID NO:10): TYAMN; CDR2 having the sequence (SEQ ID NO:11) RIRSKYN-NYATYYADSVKD; and CDR3 having the sequence (SEQ ID NO:12): HGNFGNSYVSWFAY.

The VL Domain of a murine antibody that binds gpA33 (VL$_{gpA33}$) (SEQ ID NO:13):

QIVLTQSPAIMSASPGERVTMTCSARSSISFMYWYQQKPGSSPRLLIYDT

SNLASGVPVRFSGSGSGTSYSLTISRMEAEDAATYYCQQWSSYPLTFGSG

TKLELK

The Antigen Binding Domain of VL$_{gpA33}$ comprises CDR1 having the sequence (SEQ ID NO:14): SARSS-ISFMY; CDR2 having the sequence (SEQ ID NO:15): DTSNLAS; and CDR3 having the sequence (SEQ ID NO:16): QQWSSYPLT.

The VH Domain of a murine antibody that binds gpA33 (VH$_{gpA33}$) (SEQ ID NO:17):

QVQLQQSGPELVKPGASVKISCKASGYTFSGSWMNWVKQRPGQGLEWIGR

IYPGDGETNYNGKFKDKATLTADKSSTTAYMELSSLTSVDSAVYFCARIY

GNNVYFDVWGAGTTVTVSS

The Antigen Binding Domain of VH$_{gpA33}$ comprises CDR1 having the sequence (SEQ ID NO:18): GSWMN; CDR2 having the sequence (SEQ ID NO:19): RIYPGDGETNYNGKFKD; and CDR3 having the sequence (SEQ ID NO:20): IYGNNVYFDV.

The first intervening spacer peptide (Linker 1) has the sequence (SEQ ID NO:1): GGGSGGGG. The cysteine-containing spacer peptide (Linker 2) has the sequence is SEQ ID NO:2: GGCGGG.

The heterodimer-promoting Domain of the first polypeptide chain is the "E-coil" Domain (SEQ ID NO:3). The heterodimer-promoting Domain of the second polypeptide chain is the "K-coil" Domain (SEQ ID NO:4).

Thus, the first polypeptide chain of DART-1 has the sequence (SEQ ID NO:21):

QAVVTQEPSLTVSPGGTVTLTCRSSTGAVTTSNYANWVQQKPGQAPRGLI

GGTNKRAPWTPARFSGSLLGGKAALTITGAQAEDEADYYCALWYSNLWVF

GGGTKLTVLGGGSGGGGQVQLQQSGPELVKPGASVKISCKASGYTFSGS

WMNWVKQRPGQGLEWIGRIYPGDGETNYNGKFKDKATLTADKSSTTAYME

LSSLTSVDSAVYFCARIYGNNVYFDVWGAGTTVTVSSGGCGGGEVAALEK

EVAALEKEVAALEKEVAALEK

As will be appreciated, residues 1-110 of SEQ ID NO:21 are the VL Domain of an antibody that binds CD3 (VL$_{CD3}$) (SEQ ID NO:5); residues 111-118 of SEQ ID NO:21 are the first intervening spacer peptide (Linker 1) (SEQ ID NO:1); residues 119-237 of SEQ ID NO:21 are the VH Domain of a murine antibody that binds gpA33 (VH$_{gpA33}$) (SEQ ID NO:17), residues 238-243 of SEQ ID NO:21 are the cysteine-containing spacer peptide (Linker 2) (SEQ ID NO:2) and residues 244-271 of SEQ ID NO:21 are the heterodimer-promoting "E-coil" Domain (SEQ ID NO:3).

A preferred polynucleotide that encodes the first polypeptide chain of DART-1 has the sequence (SEQ ID NO:22):

caggctgtggtgactcaggagccttcactgaccgtgtccccaggcggaac tgtgacctgacatgcagatccagcacaggcgcagtgaccacatctaact acgccaattgggtgcagcagaagccaggacaggcaccaagggcctgatc gggggtacaaacaaaagggctccctggaccctgcacggttttctggaag tctgctgggcgaaaggccgctctgactattaccggggcacaggccgagg acgaagccgattactattgtgctctgtggtatagcaatctgtgggtgttc gggggtggcacaaaactgactgtgctgggaggtggtggatccggcggagg tggacaggtccagctgcagcagtctggacctgagctggtgaagcctgggg cctcagtgaagatttcctgcaaagcttcaggctacacattcagtggctct tggatgaactgggtgaagcagaggcctggacagggtcttgagtggattgg acggatctaccctggagatggagaaactaactacaatgggaagtttaagg acaaggccacactgactgcagacaaatcatccaccacagcctacatggag ctcagcagcctgacctctgtggactctgcggtctatttctgtgcaagaat ctatggtaataacgtttacttcgatgtctggggcgcagggaccacggtca ccgtgtcttccggaggatgtggcggtggagaagtggccgcactggagaaa gaggttgctgctttggagaaggaggtcgctgcacttgaaaaggaggtcgc agccctggagaaa The second polypeptide chain of DART-1 has the sequence (SEQ ID NO:23):

QIVLTQSPAIMSASPGERVTMTCSARSSISFMYWYQQKPGSSPRLLIYDT

SNLASGVPVRFSGSGSGTSYSLTISRMEAEDAATYYCQQWSSYPLTFGSG

TKLELKRGGGSGGGGEVQLVESGGGLVQPGGSLRLSCAASGFTFNTYAMN

WVRQAPGKGLEWVARIRSKYNNYATYYADSVKDRFTISRDDSKNSLYLQM

NSLKTEDTAVYYCVRHGNFGNSYVSWFAYWGQGTLVTVSSGGCGGGKVAA

LKEKVAALKEKVAALKEKVAALKE

As will be appreciated, residues 1-107 of SEQ ID NO:23 are the VL Domain of a murine antibody that binds gpA33 (VL$_{gpA33}$) (SEQ ID NO:13); residues 108-115 of SEQ ID NO:23 are the first intervening spacer peptide (Linker 1) (SEQ ID NO:1); residues 116-240 of SEQ ID NO:23 are the VH Domain of an antibody that binds CD3 (VH$_{CD3}$) (SEQ ID NO:9), residues 241-246 of SEQ ID NO:23 are the cysteine-containing spacer peptide (Linker 2) (SEQ ID NO:2) and residues 247-274 of SEQ ID NO:23 are the heterodimer-promoting "K-coil" Domain (SEQ ID NO:4).

A preferred polynucleotide that encodes the second polypeptide chain of DART-1 has the sequence (SEQ ID NO:24):

caaattgttctcacccagtctccagcaatcatgtctgcatctccagggga gagggtcaccatgacctgcagtgccaggtcaagtataagtttcatgtact ggtaccagcagaagccaggatcctcccccagactcctgatttatgacaca tccaacctggcttctggagtccctgttcgcttcagtggcagtgggtctgg gacctcttattctctcacaatcagccgaatggaggctgaagatgctgcca cttattactgccagcagtggagtagttacccactcacgttcggttctggg accaagctggagctgaaacggggtggaggatccggcggaggcggagaggt -continued

```
gcagctggtggagtctgggggaggcttggtccagcctggagggtccctga gactctcctgtgcagcctctggattcaccttcaacacatacgctatgaat tgggtccgccaggctccagggaaggggctggagtgggttgcaaggatcag gtccaagtacaacaattatgcaacctactatgccgactctgtgaaggata gattcaccatctcaagagatgattcaaagaactcactgtatctgcaaatg aacagcctgaaaaccgaggacacggccgtgtattactgtgtgagacacgg taacttcggcaattcttacgtgtcttggtttgcttattggggacagggga cactggtgactgtgtcttccggaggatgtggcggtggaaaagtggccgca ctgaaggagaaagttgctgctttgaaagagaaggtcgccgcacttaagga aaaggtcgcagccctgaaagag
```

2. The gpA33×CD3 Bi-Specific Monovalent Diabody, "DART-2"

The first and second polypeptide chains of a second preferred gpA33×CD3 bi-specific monovalent diabody, designated herein as "DART-2," comprise polypeptide domains having the following sequences:

The VL Domain of an antibody that binds CD3 (VL$_{CD3}$) (SEQ ID NO:5):

```
QAVVTQEPSLTVSPGGTVTLTCRSSTGAVTTSNYANWVQQKPGQAPRGLI

GGTNKRAPWTPARFSGSLLGGKAALTITGAQAEDEADYYCALWYSNLWVF

GGGTKLTVLG
```

The Antigen Binding Domain of VL$_{CD3}$ comprises CDR1 having the sequence: (SEQ ID NO:6) RSST-GAVTTSNYAN; CDR2 having the sequence (SEQ ID NO:7): GTNKRAP; and CDR3 having the sequence (SEQ ID NO:8): ALWYSNLWV The VH Domain of an antibody that binds CD3 (VH$_{CD3}$) (SEQ ID NO:25):

```
EVQLVESGGGLVQPGGSLRLSCAASGFTFSTYAMNWVRQAPGKGLEWVGR

IRSKYNNYATYYADSVKDRFTISRDDSKNSLYLQMNSLKTEDTAVYYCVR

HGNFGNSYVSWFAYWGQGTLVTVSS
```

The Antigen Binding Domain of VH$_{CD3}$ comprises CDR1 having the sequence (SEQ ID NO:10): TYAMN; CDR2 having the sequence (SEQ ID NO:11): RIRSKYNNYATYY-ADSVKD; and CDR3 having the sequence: (SEQ ID NO:12) HGNFGNSYVSWFAY.

The above-discussed murine antibody that binds to human gpA33 was humanized to provide the VL and VH domains of preferred diabody DART-2. These humanized domains are as follows:

The VL Domain of a humanized antibody that binds gpA33 (VL$_{gpA33}$) (SEQ ID NO:26):

```
DIQLTQSPSFLSASVGDRVTITCSARSSISFMYWYQQKPGKAPKLLIYDT

SNLASGVPSRFSGSGSGTEFTLTISSLEAEDAATYYCQQWSSYPLTFGQG

TKLEIK
```

The Antigen Binding Domain of VL$_{gpA33}$ comprises CDR1 having the sequence (SEQ ID NO:14): SARSS-ISFMY; CDR2 having the sequence (SEQ ID NO:15): DTSNLAS; and CDR3 having the sequence (SEQ ID NO:16): QQWSSYPLT.

The VH Domain of a humanized antibody that binds gpA33 (VH$_{gpA33}$) (SEQ ID NO:27):

```
QVQLVQSGAEVKKPGASVKVSCKASGYTFTGSWMNWVRQAPGQGLEWIGR

IYPGDGETNYNGKFKDRVTITADKSTSTAYMELSSLRSEDTAVYYCARIY

GNNVYFDVWGQGTTVTVSS
```

The Antigen Binding Domain of VH$_{gpA33}$ comprises CDR1 having the sequence (SEQ ID NO:18): GSWMN; CDR2 having the sequence (SEQ ID NO:19): RIYPGDGETNYNGKFKD; and CDR3 having the sequence (SEQ ID NO:20): IYGNNVYFDV.

The first intervening spacer peptide (Linker 1) has the sequence (SEQ ID NO:1): GGGSGGGG. The cysteine-containing spacer peptide (Linker 2) has the sequence is SEQ ID NO:2: GGCGGG.

The heterodimer-promoting Domain of the first polypeptide chain is the "E-coil" Domain (SEQ ID NO:3). The heterodimer-promoting Domain of the second polypeptide chain is the "K-coil" Domain (SEQ ID NO:4).

Thus, the first polypeptide chain of DART-2 has the sequence (SEQ ID NO:28):

```
QAVVTQEPSLTVSPGGTVTLTCRSSTGAVTTSNYANWVQQKPGQAPRGLI

GGTNKRAPWTPARFSGSLLGGKAALTITGAQAEDEADYYCALWYSNLWVF

GGGTKLTVLGGGGSGGGGQVQLVQSGAEVKKPGASVKVSCKASGYTFTGS

WMNWVRQAPGQGLEWIGRIYPGDGETNYNGKFKDRVTITADKSTSTAYME

LSSLRSEDTAVYYCARIYGNNVYFDVWGQGTTVTVSSGGCGGGEVAALEK

EVAALEKEVAALEKEVAALEK
```

As will be appreciated, residues 1-110 of SEQ ID NO:28 are the VL Domain of an antibody that binds CD3 (VL$_{CD3}$) (SEQ ID NO:5); residues 111-118 of SEQ ID NO:28 are the first intervening spacer peptide (Linker 1) (SEQ ID NO:1); residues 119-237 of SEQ ID NO:28 are the VH Domain of an antibody that binds gpA33 (VH$_{gpA33}$) (SEQ ID NO:27), residues 238-243 of SEQ ID NO:28 are the cysteine-containing spacer peptide (Linker 2) (SEQ ID NO:2) and residues 244-271 of SEQ ID NO:28 are the heterodimer-promoting "E-coil" Domain (SEQ ID NO:3).

A preferred polynucleotide that encodes the first polypeptide chain of DART-2 has the sequence (SEQ ID NO:29):

```
caggctgtggtgactcaggagccttcactgaccgtgtcccaggcggaac tgtgaccctgacatgcagatccagcacaggcgcagtgaccacatctaact acgccaattgggtgcagcagaagccaggacaggcaccaaggggcctgatc gggggtacaaacaaaagggctccctggaccctgcacggttttctggaag tctgctgggcggaaaggccgctctgactattaccggggcacaggccgagg acgaagccgattactattgtgctctgtggtatagcaatctgtgggtgttc gggggtggcacaaaactgactgtgctgggaggtggtggatccggcggagg tggacaggtccagctggtccagagcggggccgaagtcaaaaaaccggag caagcgtgaaggtctcctgcaaagcatcaggctatacatttacaggcagc tggatgaactgggtgaggcaggctccaggacagggactggagtggatcgg gcgcatctaccctggagacggcgaaactaactataatggaaagttcaaag
```

-continued

```
accgagtgaccatcacagccgataagtctactagtaccgcctacatggag ctgagctccctgcggtctgaagataccgccgtctactattgcgctagaat ttacggaaacaatgtctattttgacgtgtgggggcagggaacaactgtga ctgtctcctccggaggatgtggcggtggagaagtggccgcactggagaaa gaggttgctgctttggagaaggaggtcgctgcacttgaaaaggaggtcgc agccctggagaaa
```

The second polypeptide chain of DART-2 has the sequence (SEQ ID NO:30):

DIQLTQSPSFLSASVGDRVTITCSARSSISFMYWYQQKPGKAPKLLIYDT

SNLASGVPSRFSGSGSGTEFTLTISSLEAEDAATYYCQQWSSYPLTFGQG

TKLEIKGGGSGGGGEVQLVESGGGLVQPGGSLRLSCAASGFTFSTYAMNW

VRQAPGKGLEWVGRIRSKYNNYATYYADSVKDRFTISRDDSKNSLYLQMN

SLKTEDTAVYYCVRHGNFGNSYVSWFAYWGQGTLVTVSSGGCGGGKVAAL

KEKVAALKEKVAALKEKVAALKE

As will be appreciated, residues 1-106 of SEQ ID NO:30 are the VL Domain of an antibody that binds gpA33 (VL$_{gpA33}$) (SEQ ID NO:26); residues 107-114 of SEQ ID NO:30 are the first intervening spacer peptide (Linker 1) (SEQ ID NO:1); residues 115-239 of SEQ ID NO:30 are the VH Domain of an antibody that binds CD3 (VH$_{CD3}$) (SEQ ID NO:25), residues 240-245 of SEQ ID NO:30 are the cysteine-containing spacer peptide (Linker 2) (SEQ ID NO:2) and residues 246-273 of SEQ ID NO:30 are the heterodimer-promoting "K-coil" Domain (SEQ ID NO:4).

A preferred polynucleotide that encodes the second polypeptide chain of DART-2 has the sequence (SEQ ID NO:31):

```
gacattcagctgactcagtcccctcttttctgtccgcatccgtcggaga tcgagtgactattacttgctctgctaggtcctcaatcagcttcatgtact ggtatcagcagaagcccggcaaagcacctaagctgctgatctacgacaca agcaacctggcctccgggggtgccatctcggttctctggcagtgggtcagg aactgagtttaccctgacaattagctccctggaggctgaagatgccgcta cctactattgccagcagtggagcagctatcctctgaccttcggacagggg actaaactggaaatcaagggtggaggatccggcggcggaggcgaggtgca gctggtggagtctgggggaggcttggtccagcctggagggtccctgagac tctcctgtgcagcctctggattcaccttcagcacatacgctatgaattgg gtccgccaggctccagggaaggggctggagtgggttggaaggatcaggtc caagtacaacaattatgcaacctactatgccgactctgtgaaggatagat tcaccatctcaagagatgattcaaagaactcactgtatctgcaaatgaac agcctgaaaaccgaggacacggccgtgtattactgtgtgagacacggtaa cttcggcaattcttacgtgtcttggtttgcttattggggacaggggacac tggtgactgtgtcttccggaggatgtggcggtggaaaagtggccgcactg aaggagaaagttgctgctttgaaagagaaggtcgccgcacttaaggaaaa ggtcgcagccctgaaagag
```

3. The gpA33×CD3 Bi-Specific Monovalent Diabody Having an Albumin-Binding Domain (ABD) ("DART-2 w/ABD")

In another embodiment of the invention, the gpA33×CD3 bi-specific monovalent diabody will comprise an Albumin-Binding Domain ("ABD") (gpA33×CD3 bi-specific monovalent diabody with ABD").

As disclosed in WO 2012/018687, in order to improve the in vivo pharmacokinetic properties of diabody molecules, the molecules may be modified to contain a polypeptide portion of a serum-binding protein at one or more of the termini of the diabody molecule. Most preferably, such polypeptide portion of a serum-binding protein will be installed at the C-terminus of the diabody molecule. A particularly preferred polypeptide portion of a serum-binding protein for this purpose is the albumin binding domain (ABD) from streptococcal protein G. The albumin binding domain 3 (ABD3) of protein G of Streptococcus strain G148 is particularly preferred.

The albumin binding domain 3 (ABD3) of protein G of Streptococcus strain G148 consists of 46 amino acid residues forming a stable three-helix bundle and has broad albumin binding specificity (Johansson, M. U. et al. (2002) "Structure, Specificity, And Mode Of Interaction For Bacterial Albumin-Binding Modules," J. Biol. Chem. 277(10): 8114-8120). Albumin is the most abundant protein in plasma and has a half-life of 19 days in humans. Albumin possesses several small molecule binding sites that permit it to non-covalently bind to other proteins and thereby extend their serum half-lives.

Thus, the first polypeptide chain or second polypeptide chain of a gpA33×CD3 bi-specific monovalent diabody having an Albumin-Binding Domain contains a third linker (Linker 3), which separates the E-coil (or K-coil) of such polypeptide chain from the Albumin-Binding Domain. A preferred sequence for such Linker 3 is GGGS (SEQ ID NO:32) or GGGNS (SEQ ID NO:33). A preferred Albumin-Binding Domain (ABD) has the amino acid sequence (SEQ ID NO:34):

LAQAKEAAIRELDKYGVSDYYKNLIDNAKSAEGVKALIDEILAALP

In order to illustrate this aspect of the invention, the first polypeptide chain of the above-described DART-2 was modified to contain an Albumin-Binding Domain, resulting in a gpA33×CD3 bi-specific monovalent diabody having an ABD, designated herein as "DART-2 w/ABD."

The first polypeptide chain of such DART-2 w/ABD has the amino acid sequence (SEQ ID NO:35):

QAVVTQEPSLTVSPGGTVTLTCRSSTGAVTTSNYANWVQQKPGQAPRGLI

GGTNKRAPWTPARFSGSLLGGKAALTITGAQAEDEADYYCALWYSNLWVF

GGGTKLTVLGGGGSGGGGQVQLVQSGAEVKKPGASVKVSCKASGYTFTGS

WMNWVRQAPGQGLEWIGRIYPGDGETNYNGKFKDRVTITADKSTSTAYME

LSSLRSEDTAVYYCARIYGNNVYFDVWGQGTTVTVSSGGCGGGEVAALEK

EVAALEKEVAALEKEVAALEKGGGSLAQAKEAAIRELDKYGVSDYYKNLI

DNAKSAEGVKALIDEILAALP

As will be recognized, residues 1-271 of SEQ ID NO:35 are identical to residues 1-271 of DART-2, and thus provide, in the N-terminal to C-terminal direction, the VL Domain of an antibody that binds CD3 (VL$_{CD3}$) (SEQ ID NO:5); the first intervening spacer peptide (Linker 1) (SEQ ID NO:1); the VH Domain of an antibody that binds gpA33 (VH$_{gpA33}$) (SEQ ID NO:27), the cysteine-containing spacer peptide (Linker 2) (SEQ ID NO:2), the heterodimer-promoting "E-coil" Domain (SEQ ID NO:3) and a C-terminus. Residues 272-275 are Linker 3 (SEQ ID NO:32), and residues 276-321 are an Albumin-Binding Domain (SEQ ID NO:34).

A preferred polynucleotide that encodes the first polypeptide chain of DART-2 w/ABD has the sequence (SEQ ID NO:36):

```
caggctgtggtgactcaggagccttcactgacgtgtcccccaggcggaac
tgtgaccctgacatgcagatccagcacaggcgcagtgaccacatctaact
acgccaattgggtgcagcagaagccaggacaggcaccaaggggcctgatc
gggggtacaaacaaaagggctccctggacccctgcacggttttctggaag
tctgctgggcgaaaggccgctctgactattaccggggcacaggccgagg
acgaagccgattactattgtgctctgtggtatagcaatctgtgggtgttc
gggggtggcacaaaactgactgtgctgggaggggtggatccggcggagg
tggacaggtccagctggtccagagcggggccgaagtcaaaaaacccggag
caagcgtgaaggtctcctgcaaagcatcaggctatacatttacaggcagc
tggatgaactgggtgaggcaggctccaggacagggactggagtggatcgg
gcgcatctaccctggagacggcgaaactaactataatggaaagttcaaag
accgagtgaccatcacagccgataagtctactagtaccgcctacatggag
ctgagctccctgcggtctgaagataccgccgtctactattgcgctagaat
ttacggaaacaatgtctattttgacgtgtgggggcagggaacaactgtga
ctgtctcctccggaggatgtggcggtggagaagtggccgcactggagaaa
gaggttgctgctttggagaaggaggtcgctgcacttgaaaaggaggtcgc
agccctggagaaaggcggcgggtctctggcccaggcaaaagaggcagcca
tccgcgaactggataaatatggcgtgagcgattattataagaacctgatt
gacaacgcaaaatccgcggaaggcgtgaaagcactgattgatgaaattct
ggccgccctgcct
```

The second polypeptide chain of DART-2 w/ABD is the same as the above-discussed second polypeptide chain of DART-2 (SEQ ID NO:30).

B. The gpA33×CD3 Bi-Specific Monovalent Diabodies Having an IgG Fc Domain ("DART-2 w/Fc")

In a further embodiment, the invention provides gpA33× CD3 bi-specific monovalent diabodies having an IgG Fc Domain. Such diabodies are accordingly referred to herein as "gpA33×CD3 bi-specific monovalent Fc diabodies." The Fc Domain of the Fc diabodies of the present invention may be either a complete Fc region (e.g., a complete IgG Fc region) or only a fragment of a complete Fc region. Although the Fc Domain of the bi-specific monovalent Fc diabodies of the present invention may possess the ability to bind to one or more Fc receptors (e.g., FcγR(s)), more preferably such Fc Domain will cause reduced binding to FcγRIA (CD64), FcγRIIA (CD32A), FcγRIIB (CD32B), FcγRIIIA (CD16a) or FcγRIIIB (CD16b) (relative to the binding exhibited by a wild-type Fc region) or will substantially eliminate the ability of such Fc Domain to bind to such receptor(s). The Fc Domain of the bi-specific monovalent Fc diabodies of the present invention may include some or all of the CH2 Domain and/or some or all of the CH3 Domain of a complete Fc region, or may comprise a variant CH2 and/or a variant CH3 sequence (that may include, for example, one or more insertions and/or one or more deletions with respect to the CH2 or CH3 domains of a complete Fc region). The Fc Domain of the bi-specific monovalent Fc diabodies of the present invention may comprise non-Fc polypeptide portions, or may comprise portions of non-naturally complete Fc regions, or may comprise non-naturally occurring orientations of CH2 and/or CH3 domains (such as, for example, two CH2 domains or two CH3 domains, or in the N-terminal to C-terminal direction, a CH3 Domain linked to a CH2 Domain, etc.).

Figure 2A:
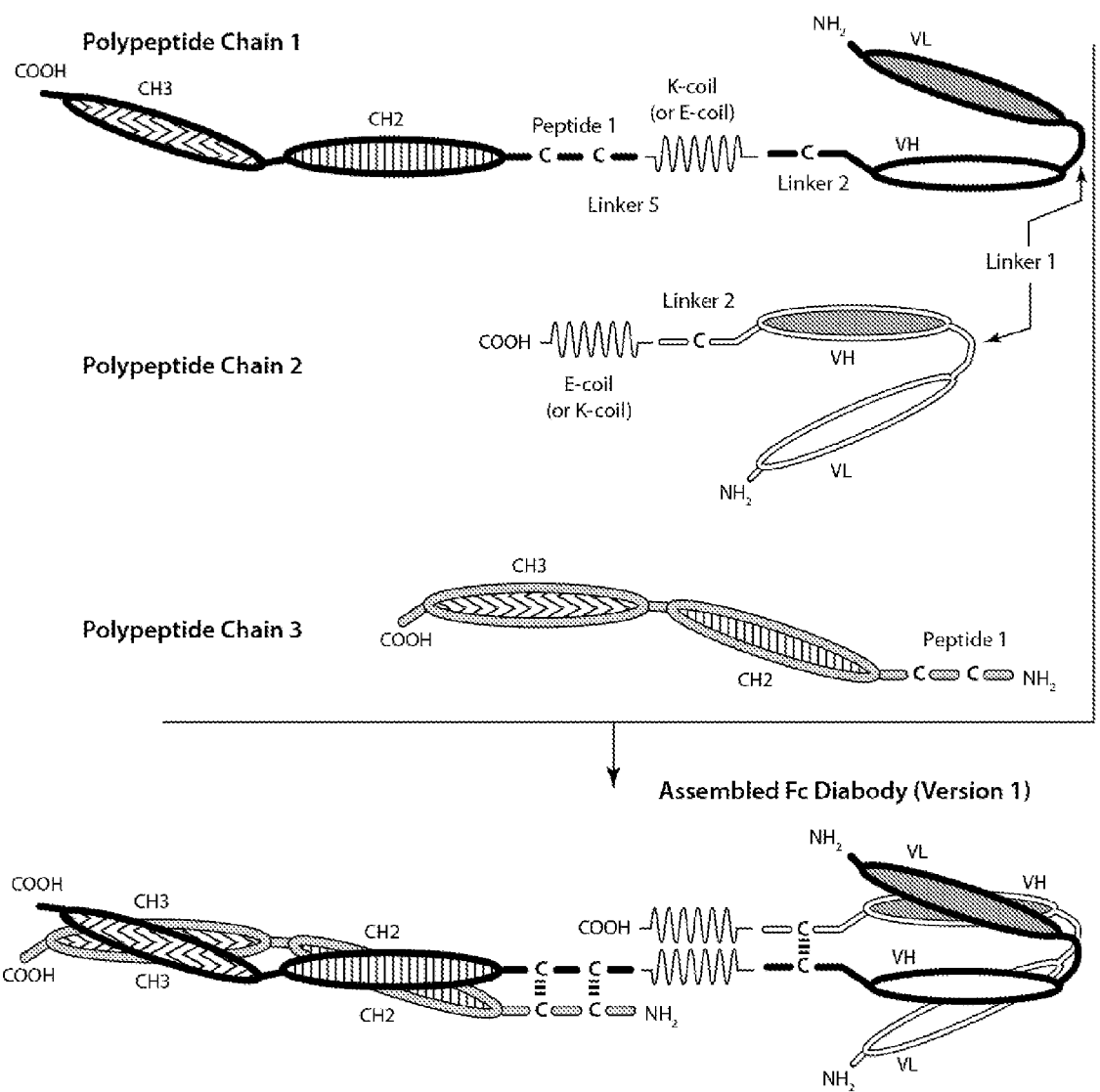
FIGS. 2A and 2B illustrate the structures of two versions of the first, second and third polypeptide chains of a three chain gpA33×CD3 bi-specific monovalent Fc diabody of the present invention (Version 1, FIG. 2A; Version 2, FIG. 2B).

In a first embodiment, denoted as "Version 1" and shown in FIG. 2A, the first polypeptide chain of an exemplary gpA33×CD3 bi-specific monovalent Fc diabody will comprise, in the N-terminal to C-terminal direction, an N-terminus, the VL Domain of a monoclonal antibody capable of binding to either gpA33 or CD3 (i.e., either VL$_{gpA33}$ or VL$_{CD3}$), an intervening spacer peptide (Linker 1), a VH Domain of a monoclonal antibody capable of binding to either gpA33 (if such first polypeptide chain contains VL$_{CD3}$) or CD3 (if such first polypeptide chain contains VL$_{gpA33}$), a cysteine-containing second intervening spacer peptide (Linker 2), a heterodimer-promoting Domain, a spacer peptide (Linker 5), a cysteine-containing peptide (Peptide 1), an IgG Fc Domain (preferably, all or a portion of the CH2 and CH3 domains of an antibody Fc region), and a C-terminus.

Figure 2B:
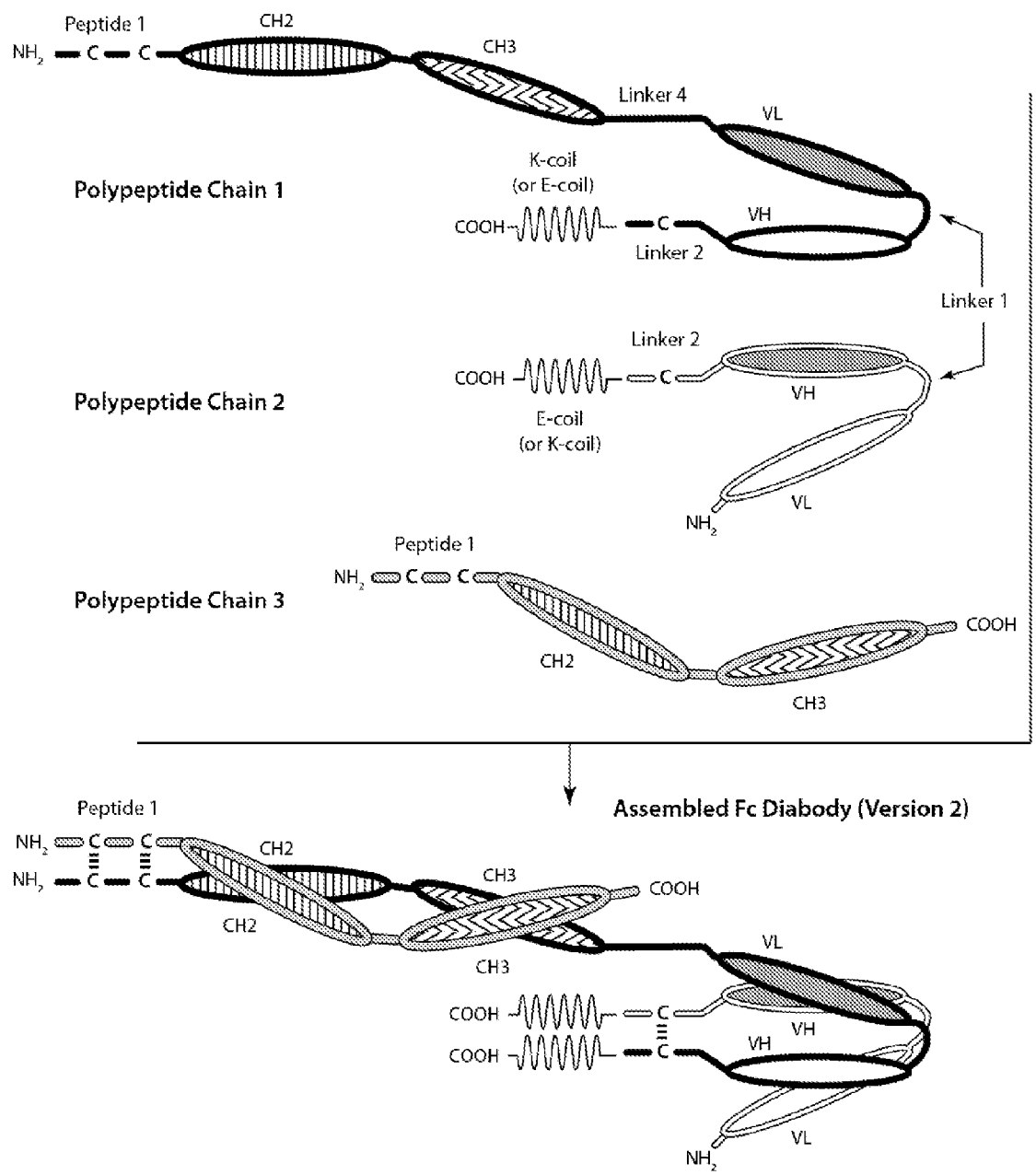

In a second embodiment, denoted as "Version 2" and shown in FIG. 2B, the first polypeptide chain of an exemplary gpA33×CD3 bi-specific monovalent Fc diabody will comprise, in the N-terminal to C-terminal direction, an N-terminus, a cysteine-containing peptide (Peptide 1), an IgG Fc Domain (preferably, all or a portion of the CH2 and CH3 domains of an antibody Fc region), an intervening spacer peptide (Linker 4); the VL Domain of a monoclonal antibody capable of binding to either gpA33 or CD3 (i.e., either VL$_{gpA33}$ or VL$_{CD3}$), an intervening spacer peptide (Linker 1), a VH Domain of a monoclonal antibody capable of binding to either gpA33 (if such first polypeptide chain contains VL$_{CD3}$) or CD3 (if such first polypeptide chain contains VL$_{gpA33}$), a cysteine-containing second intervening spacer peptide (Linker 2), a heterodimer-promoting Domain, and a C-terminus.

Preferably, in either embodiment, the Fc Domain of the first polypeptide chain will cause reduced binding to FcγRIA (CD64), FcγRIIA (CD32A), FcγRIIB (CD32B), FcγRIIIA (CD16a) or FcγRIIIB (CD16b) (relative to the binding exhibited by a wild-type Fc region) or will substantially eliminate the ability of such Fc Domain to bind to such receptor(s). Fc variants and mutant forms capable of mediating such altered binding are well known in the art and include amino acid substitutions at positions 234 and 235, a substitution at position 265 or a substitution at position 297 (see, for example, U.S. Pat. No. 5,624,821, herein incorporated by reference). In a preferred embodiment the CH2 and CH3 Domain includes a substitution at position 234 with alanine and 235 with alanine.

The second polypeptide chain of such exemplary gpA33× CD3 bi-specific monovalent Fc diabodies (Version 1 and Version 2) will comprise, in the N-terminal to C-terminal direction, an N-terminus, a VL Domain of a monoclonal antibody capable of binding to either gpA33 or CD3 (i.e., either VL$_{gpA33}$ or VL$_{CD3}$, depending upon the VL Domain selected for the first polypeptide chain of the diabody), an intervening linker peptide (Linker 1), a VH Domain of a monoclonal antibody capable of binding to either CD3 (if such second polypeptide chain contains $VL_{gpA33}$) or CD3 (if such second polypeptide chain contains $VL_{CD3}$), a cysteine-containing spacer peptide (Linker 2), a heterodimer-promoting Domain (preferably a K-coil Domain), and a C-terminus.

The exemplary gpA33×CD3 bi-specific monovalent Fc diabodies (Version 1 and Version 2) will additionally comprise a third polypeptide chain that will comprise, in the N-terminal to C-terminal direction, an N-terminus, a cysteine-containing peptide (Peptide 1), an IgG Fc Domain (preferably, all or a portion of the CH2 and CH3 domains of an antibody Fc region) having the same isotype as that of the Fc Domain of the first polypeptide chain and a C-terminus. Preferably, the Fc Domain of the third polypeptide chain will cause reduced binding to FcγRIA (CD64), FcγRIIA (CD32A), FcγRIIB (CD32B), FcγRIIIA (CD16a) or FcγRIIIB (CD16b) (relative to the binding exhibited by a wild-type Fc region) or will substantially eliminate the ability of such Fc Domain to bind to such receptor(s), as discussed above, with respect to the first polypeptide chain of the exemplary gpA33×CD3 bi-specific monovalent Fc diabodies.

The optionally present intervening spacer peptide (Linker 4) will preferably comprise the amino acid sequence (SEQ ID NO:37): APSSS, and more preferably have the amino acid sequence (SEQ ID NO:38): APSSSPME.

The cysteine-containing peptide (Peptide 1) of the first and third polypeptide chains may be comprised of the same amino acid sequence or of different amino acid sequences, and will contain 1, 2, 3 or more cysteine residues. A particularly preferred Peptide 1 has the amino acid sequence (SEQ ID NO:39): DKTHTCPPCP.

The intervening spacer peptide (Linker 1) preferably has the sequence of SEQ ID NO:1, described above. The cysteine-containing second intervening spacer peptide (Linker 2) preferably has the sequence of SEQ ID NO:2, described above.

The heterodimer-promoting Domain of the first and second polypeptide chains of the gpA33×CD3 bi-specific monovalent Fc diabodies will preferably by the above-described E-coil Domain (SEQ ID NO:3) and K-coil Domain (SEQ ID NO:4), and will be selected so that one of such polypeptide chains possesses an E-coil Domain, whereas the other possesses a K-coil Domain, as discussed above.

A preferred spacer peptide (Linker 5) has the sequence GGG.

The CH2 and/or CH3 domains of the first and third polypeptides need not be identical, and advantageously are modified to foster complexing between the two polypeptides. For example, an amino acid substitution (preferably a substitution with an amino acid comprising a bulky side group forming a 'knob', e.g., tryptophan) can be introduced into the CH2 or CH3 Domain such that steric interference will prevent interaction with a similarly mutated Domain and will obligate the mutated Domain to pair with a Domain into which a complementary, or accommodating mutation has been engineered, i.e., 'the hole' (e.g., a substitution with glycine). Such sets of mutations can be engineered into any pair of polypeptides comprising the bi-specific monovalent Fc diabody molecule, and further, engineered into any portion of the polypeptides chains of said pair. Methods of protein engineering to favor heterodimerization over homodimerization are well known in the art, in particular with respect to the engineering of immunoglobulin-like molecules, and are encompassed herein (see e.g., Ridgway et al. (1996) "'*Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety). Preferably the 'knob' is engineered into the CH2-CH3 domains of the first polypeptide chain and the 'hole' is engineered into the CH2-CH3 domains of the third polypeptide chain. Thus, the 'knob' will help in preventing the first polypeptide chain from homodimerizing via its CH2 and/or CH3 domains. As the third polypeptide chain preferably contains the 'hole' substitution it will heterodimerize with the first polypeptide chain as well as homodimerize with itself. A preferred knob is created by modifying an Fc Domain of a native IgG Fc region to contain the modification T366W. A preferred hole is created by modifying an Fc Domain of a native IgG Fc region to contain the modification T366S, L368A and Y407V. To aid in purifying the third polypeptide chain homodimer from the final bi-specific monovalent Fc diabody comprising the first, second and third polypeptide chains, the protein A binding site of the CH2 and CH3 domains of the third polypeptide chain is preferably mutated by amino acid substitution at position 435 (H435R). To aid in purifying the third polypeptide chain homodimer from the final bi-specific monovalent Fc diabody comprising the first, second and third polypeptide chains, the protein A binding site of the CH2 and CH3 domains of the third polypeptide chain is preferably mutated by amino acid substitution. Thus the third polypeptide chain homodimer will not bind to protein A, whereas the bi-specific monovalent Fc diabody will retain its ability to bind protein A via the protein A binding site on the first polypeptide chain.

A preferred sequence for the CH2 and CH3 domains of an antibody Fc Domain present in the first polypeptide chain is (SEQ ID NO:40):

```
APEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAKGQPREPQVYTLPPSREEMTKNQVSLWCLVKGFYPSDIAVE
WESNGQPENNYKTTPPVLDSDGSFFLYSKLTVDKSRWQQGNVFSCSVMHE
ALHNHYTQKSLSLSPGK
```

A preferred sequence for the CH2 and CH3 domains of an antibody Fc Domain present in the third polypeptide chain is (SEQ ID NO:41):

```
APEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAKGQPREPQVYTLPPSREEMTKNQVSLSCAVKGFYPSDIAVE
WESNGQPENNYKTTPPVLDSDGSFFLVSKLTVDKSRWQQGNVFSCSVMHE
ALHNRYTQKSLSLSPGK
```

1. DART-2 w/Fc Version 1

The first, second and third polypeptide chains of a preferred gpA33×CD3 bi-specific monovalent Fc diabody, designated herein as "DART-2 w/Fc Version 1," comprise polypeptide domains having the following sequences:

The first polypeptide chain of such DART-2 w/Fc Version 1 has the amino acid sequence (SEQ ID NO:42):

DIQLTQSPSFLSASVGDRVTITCSARSSISFMYWYQQKPGKAPKLLIYDT

SNLASGVPSRFSGSGSGTEFTLTISSLEAEDAATYYCQQWSSYPLTFGQG

TKLEIKGGGSGGGGEVQLVESGGGLVQPGGSLRLSCAASGFTFSTYAMNW

VRQAPGKGLEWVGRIRSKYNNYATYYADSVKDRFTISRDDSKNSLYLQMN

SLKTEDTAVYYCVRHGNFGNSYVSWFAYWGQGTLVTVSSGGCGGGEVAAL

EKEVAALEKEVAALEKEVAALEKGGGDKTHTCPPCPAPEAAGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLWCLVKGFYPSDIAVEWESNGQPENNYKTT

PPVLDSDGSFFLYSKLTVDKSRWQQGNVFSCSVMHEALHNHYTQKSLSLS

PGK

As will be appreciated, residues 1-106 of SEQ ID NO:42 are the VL Domain of an antibody that binds gpA33 (VL$_{gpA33}$) (SEQ ID NO:26); residues 107-114 of SEQ ID NO:42 are the first intervening spacer peptide (Linker 1) (SEQ ID NO:1); residues 115-239 of SEQ ID NO:42 are the VH Domain of an antibody that binds CD3 (VH$_{CD3}$) (SEQ ID NO:25); residues 240-245 of SEQ ID NO:42 are the cysteine-containing spacer peptide (Linker 2) (SEQ ID NO:2); residues 246-273 of SEQ ID NO:42 are the heterodimer-promoting "E-coil" Domain (SEQ ID NO:3); residues 274-276 are the spacer peptide GGG (Linker 5); residues 277-286 are Peptide 1 (SEQ ID NO:39), residues 277-503 are the sequence for the CH2 and CH3 domains of an antibody Fc Domain (SEQ ID NO:40).

A preferred polynucleotide that encodes the first polypeptide chain of DART-2 w/Fc Version 1 has the sequence (SEQ ID NO:43):

gacattcagctgactcagtcccctcttttctgtccgcatccgtcggaga tcgagtgactattacttgctctgctaggtcctcaatcagcttcatgtact ggtatcagcagaagcccggcaaagcacctaagctgctgatctacgacaca agcaacctggcctccggggtgccatctcggttctctggcagtgggtcagg aactgagtttaccctgacaattagctccctggaggctgaagatgccgcta cctactattgccagcagtggagcagctatcctctgaccttcggacagggg actaaactggaaatcaagggtggaggatccggcggcggaggcgaggtgca gctggtggagtctgggggaggcttggtccagcctggagggtccctgagac tctcctgtgcagcctctggattcaccttcagcacatacgctatgaattgg gtccgccaggctccagggaaggggctggagtgggttggaaggatcaggtc caagtacaacaattatgcaacctactatgccgactctgtgaaggatagat tcaccatctcaagagatgattcaaagaactcactgtatctgcaaatgaac agcctgaaaaccgaggacacggccgtgtattactgtgtgagacacggtaa cttcggcaattcttacgtgtcttggtttgcttattggggacaggggacac tggtgactgtgtcttccggaggatgtggcggtggagaagtggccgcactg gagaaagaggttgctgctttggagaaggaggtcgctgcacttgaaaagga ggtcgcagccctggagaaaggcggcgggacaaaactcacacatgccac cgtgcccagcacctgaagccgcgggggaccgtcagtcttcctcttccc ccaaaacccaaggacaccctcatgatctcccggacccctgaggtcacatg cgtggtggtggacgtgagccacgaagaccctgaggtcaagttcaactggt acgtggacggcgtggaggtgcataatgccaagacaaagccgcgggaggag cagtacaacagcacgtaccgtgtggtcagcgtcctcaccgtcctgcacca ggactggctgaatggcaaggagtacaagtgcaaggtctccaacaaagccc tcccagcccccatcgagaaaaccatctccaaagccaaagggcagccccga gaaccacaggtgtacaccctgcccccatcccgggaggagatgaccaagaa ccaggtcagcctgtggtgcctggtcaaaggcttctatcccagcgacatcg ccgtggagtgggagagcaatgggcagccggagaacaactacaagaccacg cctcccgtgctggactccgacggctccttcttcctctacagcaagctcac cgtggacaagagcaggtggcagcaggggaacgtcttctcatgctccgtga tgcatgaggctctgcacaaccactacacgcagaagagcctctccctgtct ccgggtaaa The second polypeptide chain of such DART-2 w/Fc Version 1 has the amino acid sequence (SEQ ID NO:44):

QAVVTQEPSLTVSPGGTVTLTCRSSTGAVTTSNYANWVQQKPGQAPRGLI

GGTNKRAPWTPARFSGSLLGGKAALTITGAQAEDEADYYCALWYSNLWVF

GGGTKLTVLGGGGSGGGGQVQLVQSGAEVKKPGASVKVSCKASGYTFTGS

WMNWVRQAPGQGLEWIGRIYPGDGETNYNGKFKDRVTITADKSTSTAYME

LSSLRSEDTAVYYCARIYGNNVYFDVWGQGTTVTVSSGGCGGGKVAALKE

KVAALKEKVAALKEKVAALKE

As will be appreciated, residues 1-110 of SEQ ID NO:44 are the VL Domain of an antibody that binds CD3 (VL$_{CD3}$) (SEQ ID NO:5); residues 111-118 of SEQ ID NO:44 are the first intervening spacer peptide (Linker 1) (SEQ ID NO:1); residues 119-237 of SEQ ID NO:44 are the VH Domain of an antibody that binds gpA33 (VH$_{gpA33}$) (SEQ ID NO:27), residues 238-243 of SEQ ID NO:44 are the cysteine-containing spacer peptide (Linker 2) (SEQ ID NO:2) and residues 244-271 of SEQ ID NO:44 are the heterodimer-promoting "K-coil" Domain (SEQ ID NO:4).

A preferred polynucleotide that encodes the second polypeptide chain of DART-2 w/Fc Version 1 has the sequence (SEQ ID NO:45):

caggctgtggtgactcaggagccttcactgaccgtgtcccaggcggaac tgtgacctgacatgcagatccagcacaggcgcagtgaccacatctaact acgccaattgggtgcagcagaagccaggacaggcaccaaggggcctgatc gggggtacaaacaaaagggctccctggacccctgcacggttttctggaag tctgctgggcgaaaggccgctctgactattaccggggcacaggccgagg acgaagccgattactattgtgctctgtggtatagcaatctgtgggtgttc ggggtggcacaaaactgactgtgctggggaggggtggatccggcggagg tggacaggtccagctggtccagagcggggccgaagtcaaaaaacccggag caagcgtgaaggtctcctgcaaagcatcaggctatacatttacaggcagc -continued
tggatgaactgggtgaggcaggctccaggacagggactggagtggatcgg gcgcatctaccctggagacggcgaaactaactataatggaaagttcaaag accgagtgaccatcacagccgataagtctactagtaccgcctacatggag ctgagctccctgcggtctgaagataccgccgtctactattgcgctagaat ttacggaaacaatgtctattttgacgtgtgggggcagggaacaactgtga ctgtctcctccggaggatgtggcggtggaaaagtggccgcactgaaggag aaagttgctgctttgaaagagaaggtcgccgcacttaaggaaaaggtcgc agccctgaaagag The third polypeptide chain of such DART-2 w/Fc Version 1 has the amino acid sequence (SEQ ID NO:46):

DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLSCAVK

GFYPSDIAVEWESNGQPENNYKTTPPVLDSDGSFFLVSKLTVDKSRWQQG

NVFSCSVMHEALHNRYTQKSLSLSPGK

As will be appreciated, residues 1-10 of SEQ ID NO:46 are Peptide 1 (SEQ ID NO:39) and residues 11-227 are the CH2 and CH3 domains of an antibody Fc Domain (SEQ ID NO:41).

A preferred polynucleotide that encodes the third polypeptide chain of DART-2 w/Fc Version 1 has the sequence (SEQ ID NO:47):

gacaaaactcacacatgcccaccgtgcccagcacctgaagccgcgggggg accgtcagtcttcctcttccccccaaaacccaaggacaccctcatgatct cccgacccctgaggtcacatgcgtggtggtggacgtgagccacgaagac cctgaggtcaagttcaactggtacgtggacggcgtggaggtgcataatgc caagacaaagccgcgggaggagcagtacaacagcacgtaccgtgtggtca gcgtcctcaccgtcctgcaccaggactggctgaatggcaaggagtacaag tgcaaggtctccaacaaagccctcccagccccatcgagaaaaccatctc caaagccaaagggcagccccgagaaccacaggtgtacaccctgcccccat cccgggaggagatgaccaagaaccaggtcagcctgagttgcgcagtcaaa ggcttctatcccagcgacatcgccgtggagtgggagagcaatgggcagcc ggagaacaactacaagaccacgcctcccgtgctggactccgacggctcct tcttcctcgtcagcaagctcaccgtggacaagagcaggtggcagcagggg aacgtcttctcatgctccgtgatgcatgaggctctgcacaaccgctacac gcagaagagcctctccctgtctccgggtaaa 2. DART-2 w/Fc Version 2

The first, second and third polypeptide chains of a second preferred gpA33×CD3 bi-specific monovalent Fc diabody, designated herein as "DART-2 w/Fc Version 2," comprise polypeptide domains having the following sequences. Among other differences, DART-2 w/Fc Version 1 differs from DART-2 w/Fc Version 22 in the positioning of the CH2 and CH3 sequences of the first polypeptide chain; these sequences are positioned C-terminal to the VL and VH sequences of DART-2 w/Fc Version 1, whereas they are positioned N-terminal to the VL and VH sequences of DART-2 w/Fc Version 2.

The first polypeptide chain of such DART-2 w/Fc Version 2 has the amino acid sequence (SEQ ID NO:48):

DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLWCLVK

GFYPSDIAVEWESNGQPENNYKTTPPVLDSDGSFFLYSKLTVDKSRWQQG

NVFSCSVMHEALHNHYTQKSLSLSPGKAPSSSPMEDIQLTQSPSFLSASV

GDRVTITCSARSSISFMYWYQQKPGKAPKLLIYDTSNLASGVPSRFSGSG

SGTEFTLTISSLEAEDAATYYCQQWSSYPLTFGQGTKLEIKGGGSGGGGE

VQLVESGGGLVQPGGSLRLSCAASGFTFSTYAMNWVRQAPGKGLEWVGRI

RSKYNNYATYYADSVKDRFTISRDDSKNSLYLQMNSLKTEDTAVYYCVRH

GNFGNSYVSWFAYWGQGTLVTVSSGGCGGGKVAALKEKVAALKEKVAALK

EKVAALKE

As will be appreciated, residues 1-10 of SEQ ID NO:48 are Peptide 1 (SEQ ID NO:39); residues 11-227 of SEQ ID NO:48 are the sequence for the CH2 and CH3 domains of an antibody Fc Domain (SEQ ID NO:40); residues 228-235 of SEQ ID NO:48 are intervening spacer peptide (Linker 4) (SEQ ID NO:38); residues 236-341 of SEQ ID NO:48 are the VL Domain of an antibody that binds gpA33 ($VL_{gpA33}$) (SEQ ID NO:26); residues 342-349 of SEQ ID NO:48 are the first intervening spacer peptide (Linker 1) (SEQ ID NO:1); residues 350-474 of SEQ ID NO:48 are the VH Domain of an antibody that binds CD3 ($VH_{CD3}$) (SEQ ID NO:25); residues 475-480 of SEQ ID NO:48 are the cysteine-containing spacer peptide (Linker 2) (SEQ ID NO:2); and residues 481-508 of SEQ ID NO:48 are the heterodimer-promoting "K-coil" Domain (SEQ ID NO:4).

The second polypeptide chain of such DART-2 w/Fc Version 2 has the amino acid sequence of the first polypeptide chain of DART-2 (i.e., SEQ ID NO:28) (described above).

The third polypeptide chain of such DART-2 w/Fc Version 2 has the amino acid sequence of SEQ ID NO:46 (described above).

Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of the gpA33×CD3 bi-specific monovalent diabodies or gpA33×CD3 bi-specific monovalent Fc diabodies disclosed herein and an additional therapeutic agent) and a pharmaceutically acceptable carrier. Preferably, compositions of the invention comprise a prophylactically or therapeutically effective amount of one or more molecules of the invention and a pharmaceutically acceptable carrier.

The invention also encompasses pharmaceutical compositions comprising such gpA33×CD3 bi-specific monovalent diabodies or gpA33×CD3 bi-specific monovalent Fc diabodies and a second therapeutic antibody (e.g., a cancer-antigen specific monoclonal antibody) that is specific for a particular antigen associated with a cancer, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers filled with such disclosed gpA33×CD3 bi-specific monovalent diabodies or gpA33×CD3 bi-specific monovalent Fc diabodies (alone or with additional therapeutic agent(s)) and such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more molecules of the invention. In another embodiment, a kit further comprises one or more other prophylactic or therapeutic agents useful for the treatment of a cancer, in one or more containers. In another embodiment, a kit further comprises one or more antibodies that bind one or more antigens associated with a cancer. In certain embodiments, the other prophylactic or therapeutic agent is a chemotherapeutic. In other embodiments, the prophylactic or therapeutic agent is a biological or hormonal therapeutic.

Uses of the Compositions of the Invention

The gpA33×CD3 bi-specific monovalent diabodies or gpA33×CD3 bi-specific monovalent Fc diabodies of the present invention have the ability to treat any disease or condition associated with or characterized by the expression of gpA33. Thus, without limitation, pharmaceutical compositions comprising such molecules may be employed in the diagnosis or treatment of colon cancers, colorectal cancers, and pancreatic cancers.

Methods of Administration

The compositions of the present invention may be provided for the treatment, prophylaxis, and amelioration of one or more symptoms associated with a disease, disorder or infection by administering to a subject an effective amount of a pharmaceutical composition of the invention. In a preferred aspect, such compositions are substantially purified (i.e., substantially free from substances that limit its effect or produce undesired side-effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) "*Receptor-Mediated In Vitro Gene Transformation By A Soluble DNA Carrier System*," J. Biol. Chem. 262: 4429-4432), construction of a nucleic acid as part of a retroviral or other vector, etc.

Methods of administering the gpA33×CD3 bi-specific monovalent diabodies or gpA33×CD3 bi-specific monovalent Fc diabodies of the present invention include, but are not limited to, parenteral administration (e.g., intradermal, intramuscular, intraperitoneal, intravenous and subcutaneous), epidural, and mucosal (e.g., intranasal and oral routes). In a specific embodiment, the molecules of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,800,078; and PCT Publication Nos. WO 92/19244; WO 97/32572; WO 97/44013; WO 98/31346; and WO 99/66903, each of which is incorporated herein by reference in its entirety.

The invention also provides that the gpA33×CD3 bi-specific monovalent diabodies or gpA33×CD3 bi-specific monovalent Fc diabodies of the invention are packaged in a hermetically sealed container such as an ampoule or sachette indicating the quantity of such molecules. In one embodiment, the gpA33×CD3 bi-specific monovalent diabodies or gpA33×CD3 bi-specific monovalent Fc diabodies of the invention are supplied as a dry sterilized lyophilized powder or water free concentrate in a hermetically sealed container and can be reconstituted, e.g., with water or saline to the appropriate concentration for administration to a subject. Preferably, the gpA33×CD3 diabodies or gpA33×CD3 Fc diabodies of the invention are supplied as a dry sterile lyophilized powder in a hermetically sealed container at a unit dosage of at least 5 µg, more preferably at least 10 µg, at least 15 µg, at least 25 µg, at least 50 µg, at least 100 µg, or at least 200 µg.

The lyophilized gpA33×CD3 bi-specific monovalent diabodies or gpA33×CD3 bi-specific monovalent Fc diabodies of the invention should be stored at between 2 and 8° C. in their original container and the molecules should be administered within 12 hours, preferably within 6 hours, within 5 hours, within 3 hours, or within 1 hour after being reconstituted. In an alternative embodiment, gpA33×CD3 bi-specific monovalent diabodies or gpA33×CD3 bi-specific monovalent Fc diabodies of the invention are supplied in liquid form in a hermetically sealed container indicating the quantity and concentration of the molecule, fusion protein, or conjugated molecule. Preferably, the liquid form of such bi-specific monovalent diabodies or bi-specific monovalent Fc diabodies is supplied in a hermetically sealed container in which the molecules are present at a concentration of least 1 µg/ml, more preferably at least 2.5 µg/ml, at least 5 µg/ml, at least 10 µg/ml, at least 50 µg/ml, or at least 100 µg/ml.

The amount of gpA33×CD3 bi-specific monovalent diabodies or gpA33×CD3 bi-specific monovalent Fc diabodies of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For gpA33×CD3 bi-specific monovalent diabodies or gpA33×CD3 bi-specific monovalent Fc diabodies encompassed by the invention, the dosage administered to a patient is typically at least about 0.01 µg/kg, at least about 0.05 µg/kg, at least about 0.1 µg/kg, at least about 0.2 µg/kg, at least about 0.5 µg/kg, at least about 1 µg/kg, at least about 2 µg/kg, at least about 3 µg/kg, at least about 5 µg/kg, at least about 10 µg/kg, at least about 20 µg/kg, at least about 30 µg/kg, at least about 50 µg/kg, at least about 0.1 mg/kg, at least about 0.15 mg/kg, or more of the subject's body weight.

The dosage and frequency of administration of the bi-specific monovalent diabodies or bi-specific monovalent Fc diabodies of the invention may be reduced or altered by enhancing uptake and tissue penetration of the bi-specific monovalent Fc diabodies by modifications such as, for example, lipidation.

In one embodiment, the dosage of the gpA33×CD3 bi-specific monovalent diabodies or gpA33×CD3 Fc bi-specific monovalent diabodies of the invention administered to a patient may be calculated for use as a single agent therapy. In another embodiment the bi-specific monovalent diabodies or bi-specific monovalent Fc diabodies of the invention are used in combination with other therapeutic compositions and the dosage administered to a patient are lower than when such bi-specific monovalent diabodies or bi-specific monovalent Fc diabodies are used as a single agent therapy.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

In another embodiment, the compositions can be delivered in a vesicle, in particular a liposome (See Langer (1990) "*New Methods Of Drug Delivery*," Science 249:1527-1533); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid.).

In yet another embodiment, the compositions can be delivered in a controlled release or sustained release system. Any technique known to one of skill in the art can be used to produce sustained release formulations comprising one or more molecules of the invention. See, e.g., U.S. Pat. No. 4,526,938; PCT publication WO 91/05548; PCT publication WO 96/20698; Ning et al. (1996) "*Intratumoral Radioimmunotheraphy Of A Human Colon Cancer Xenograft Using A Sustained-Release Gel*," Radiotherapy & Oncology 39:179-189, Song et al. (1995) "*Antibody Mediated Lung Targeting Of Long-Circulating Emulsions*," PDA Journal of Pharmaceutical Science & Technology 50:372-397; Cleek et al. (1997) "*Biodegradable Polymeric Carriers For A bFGF Antibody For Cardiovascular Application*," Pro. Int'l. Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety. In one embodiment, a pump may be used in a controlled release system (See Langer, supra; Sefton, (1987) "*Implantable Pumps*," CRC Crit. Rev. Biomed. Eng. 14:201-240; Buchwald et al. (1980) "*Long-Term, Continuous Intravenous Heparin Administration By An Implantable Infusion Pump In Ambulatory Patients With Recurrent Venous Thrombosis*," Surgery 88:507-516; and Saudek et al. (1989) "*A Preliminary Trial Of The Programmable Implantable Medication System For Insulin Delivery*," N. Engl. J. Med. 321:574-579). In another embodiment, polymeric materials can be used to achieve controlled release of antibodies (see e.g., MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Levy et al. (1985) "*Inhibition Of Calcification Of Bioprosthetic Heart Valves By Local Controlled-Release Diphosphonate*," Science 228:190-192; During et al. (1989) "*Controlled Release Of Dopamine From A Polymeric Brain Implant: In Vivo Characterization*," Ann. Neurol. 25:351-356; Howard et al. (1989) "*Intracerebral Drug Delivery In Rats With Lesion-Induced Memory Deficits*," J. Neurosurg. 7(1):105-112); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in MEDICAL APPLICATIONS OF CONTROLLED RELEASE, supra, vol. 2, pp. 115-138 (1984)). In another embodiment, polymeric compositions useful as controlled release implants are used according to Dunn et al. (See U.S. Pat. No. 5,945,115). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled release systems are discussed in the review by Langer (1990, "New Methods Of Drug Delivery," Science 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al. (1996) "Intratumoral Radioimmunotheraphy Of A Human Colon Cancer Xenograft Using A Sustained-Release Gel," Radiotherapy & Oncology 39:179-189, Song et al. (1995) "Antibody Mediated Lung Targeting Of Long-Circulating Emulsions," PDA Journal of Pharmaceutical Science & Technology 50:372-397; Cleek et al. (1997) "Biodegradable Polymeric Carriers For A bFGF Antibody For Cardiovascular Application," Pro. Intl. Symp. Control. Rel. Bioact. Mater. 24:853-854; and Lam et al. (1997) "Microencapsulation Of Recombinant Humanized Monoclonal Antibody For Local Delivery," Proc. Intl. Symp. Control Rel. Bioact. Mater. 24:759-760, each of which is incorporated herein by reference in its entirety.

In a specific embodiment where the composition of the invention is a nucleic acid encoding a bi-specific monovalent diabody or bi-specific monovalent Fc diabody of the invention, the nucleic acid can be administered in vivo to promote expression of its encoded bi-specific monovalent diabody or bi-specific monovalent Fc diabody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al. (1991) "Antennapedia Homeobox Peptide Regulates Neural Morphogenesis," Proc. Natl. Acad. Sci. (U.S.A.) 88:1864-1868), etc. Alternatively, a nucleic acid can be introduced intracellularly and incorporated within host cell DNA for expression by homologous recombination.

Treatment of a subject with a therapeutically or prophylactically effective amount of the gpA33×CD3 bi-specific monovalent diabodies or gpA33×CD3 bi-specific monovalent Fc diabodies of the invention can include a single treatment or, preferably, can include a series of treatments. In a preferred example, a subject is treated with molecules of the invention one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the molecules used for treatment may increase or decrease over the course of a particular treatment.

Having now generally described the invention, the same will be more readily understood through reference to the following examples, which are provided by way of illustration and are not intended to be limiting of the present invention unless specified.

Example 1

Characteristics of Anti-Human gpA33 Monoclonal Antibody

A murine monoclonal antibody capable of specific binding to human gpA33 was chimericized and humanized. The VL and VH chains of the original murine antibody have the sequences of SEQ ID NOs:13 and 17, respectively. The VL and VH chains of the humanized antibody have the sequences of SEQ ID NOs:26 and 27, respectively.

The Antigen Binding Domain of $VL_{gpA33}$ comprises CDR1 having the sequence (SEQ ID NO:14): SARSSISFMY; CDR2 having the sequence (SEQ ID NO:15): DTSNLAS; and CDR3 having the sequence (SEQ ID NO:16): QQWSSYPLT.

The Antigen Binding Domain of $VH_{gpA33}$ comprises CDR1 having the sequence (SEQ ID NO:18): GSWMN; CDR2 having the sequence (SEQ ID NO:19): RIYPGDGETNYNGKFKD; and CDR3 having the sequence (SEQ ID NO:20): IYGNNVYFDV.

Table 1 shows the effect of such alterations on the kinetics of binding.

TABLE 1

| Antibody | KD | ka | kd |
|---|---|---|---|
| Murine mAb 1 | 2.3 nM | $3.3 \times 10^5$ | $7.5 \times 10^{-4}$ |
| Chimeric mAb 1 | 2.4 nM | $5.8 \times 10^5$ | $1.4 \times 10^{-3}$ |
| Humanized mAb 1 | 3.4 nM | $5.6 \times 10^5$ | $1.9 \times 10^{-3}$ |

The data indicates that the modifications resulting in the humanization of the antibody VL and VH domains did not substantially affect gpA33 binding kinetics.

Example 2

Construction of gpA33×CD3 Bi-Specific Monovalent Diabodies and Fc Diabodies and Control Diabodies Table 2 contains a list of sequences of the polypeptide chains of the preferred gpA33×CD3 diabodies and gpA33×CD3 Fc diabodies that were expressed and purified. The diabodies were found to be capable of simultaneously binding to gpA33 and CD3, as judged by the detection of such simultaneous binding by the exemplary gpA33×CD3 bi-specific monovalent diabodies, DART-1 and DART-2, and by the exemplary gpA33×CD3 bi-specific monovalent Fc diabody (DART-2 w/Fc). Additionally, a control bi-specific monovalent diabody ("Control DART") was produced that was bi-specific monovalent for CD3 and FITC, and was found to be capable of simultaneously binding to CD3 and FITC.

TABLE 2

| Diabody | Substituent Polypeptides (in the N-Terminal to C-Terminal Direction) |
|---|---|
| gpA33 × CD3 bi-specific monovalent diabody (DART-1) | SEQ ID NO: 21<br>SEQ ID NO: 23 |
| gpA33 × CD3 bi-specific monovalent diabody (DART-2) | SEQ ID NO: 28<br>SEQ ID NO: 30 |
| gpA33 × CD3 bi-specific monovalent diabody having an Albumin-Binding Domain (DART-2 w/ABD)<br>Comprises an Albumin-Binding Domain (ABD) for extension of half-life in vivo | SEQ ID NO: 35<br>SEQ ID NO: 30 |
| gpA33 × CD3 bi-specific monovalent diabody having an IgG Fc Domain version 1 (DART-2 w/Fc Version 1)<br>Comprises an Fc Domain for extension of half-life in vivo | SEQ ID NO: 42<br>SEQ ID NO: 44<br>SEQ ID NO: 46 |
| gpA33 × CD3 bi-specific monovalent diabody having an IgG Fc Domain version 2 (DART-2 w/Fc Version 2)<br>Comprises an Fc Domain for extension of half-life in vivo | SEQ ID NO: 48<br>SEQ ID NO: 28<br>SEQ ID NO: 46 |

The gpA33×CD3 bi-specific monovalent diabodies are heterodimers composed of two polypeptide chains (one chain of each recited sequence) and the gpA33×CD3 bi-specific monovalent Fc diabodies are heterotrimers composed of three polypeptide chains (one chain of each recited amino acid sequence). Methods for forming bi-specific monovalent diabodies are provided in WO 2006/113665, WO 2008/157379, WO 2010/080538, WO 2012/018687, WO 2012/162068 and WO 2012/162067.

Figure 3:
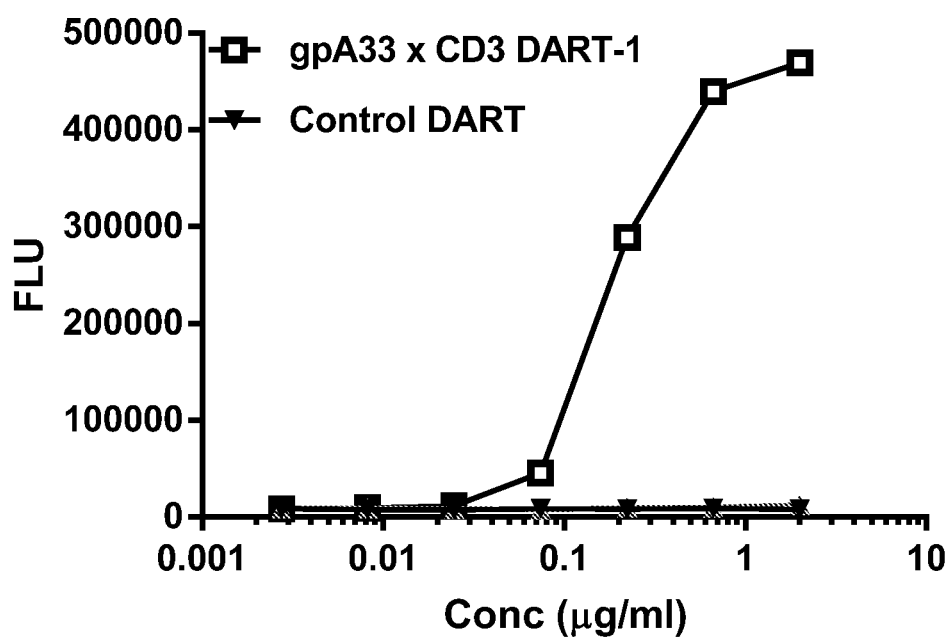
FIG. 3 demonstrates that the diabodies of the present invention are capable of simultaneously binding to CD3 and to gpA33.

The control CD3×FITC bi-specific monovalent diabody was found to be capable of simultaneously binding to CD3 and to FITC. The above-described gpA33×CD3 bi-specific monovalent diabodies and gpA33×CD3 bi-specific monovalent Fc diabodies were found to be capable of simultaneously binding to gpA33 and to CD3. In order to demonstrate such simultaneous binding, the gpA33×CD3 bi-specific monovalent diabody DART-1 was incubated in the presence of a soluble CD3 fragment that had been immobilized to a solid support. The detection of binding was assessed by the capacity of immobilized antibodies to additionally bind gpA33. The results confirm the capacity of the above-described gpA33×CD3 bi-specific monovalent diabodies and gpA33×CD3 bi-specific monovalent Fc diabodies to mediate simultaneous binding to gpA33 and CD3 (FIG. 3).

Example 3 gpA33×CD3 Bi-Specific Monovalent Diabodies are Cytotoxic to Cancer Cells

Figure 4A:
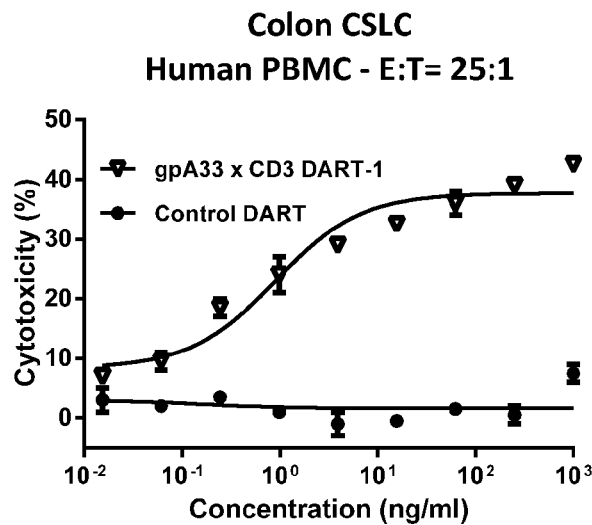
FIG. 4 illustrates the ability of the diabodies of the present invention to treat cancer. Colorectal or pancreatic cancer cells were incubated in the presence of the gpA33×CD3 bi-specific monovalent diabody ("DART-1) and either human PBMC (E:T=25:1) or activated human T cells (E:T=10:1), and cytotoxicity was measured (FIG. 4A (Colon CSCL colorectal cells), FIG. 4B (Colo205 colorectal cells), and FIG. 4C (ASPC-1 pancreatic cancer cells).
Figure 4B:
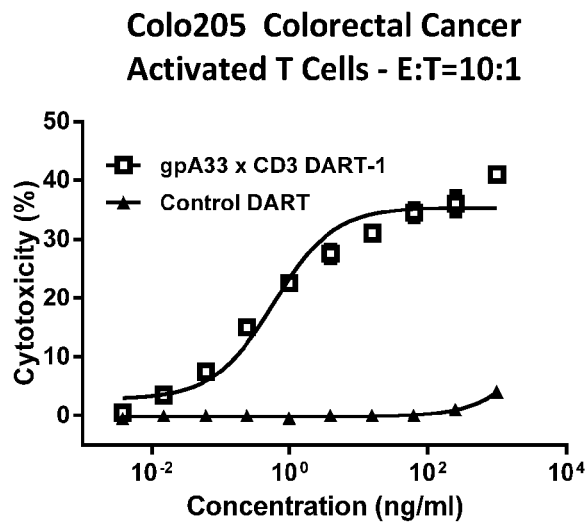
Figure 4C:
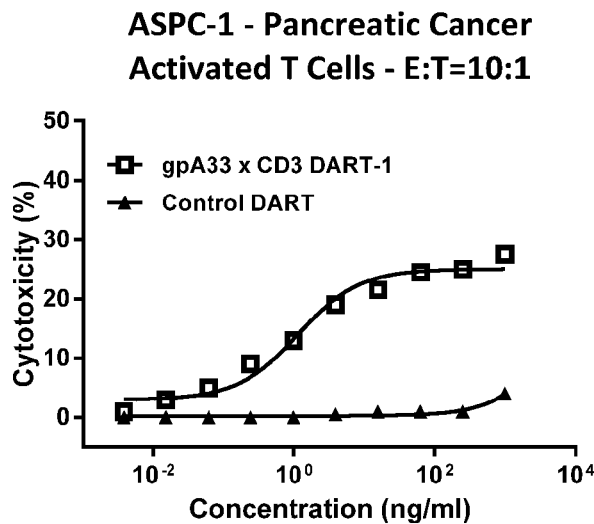

The ability of the gpA33×CD3 bi-specific monovalent diabodies of the present invention to treat cancer was illustrated by incubating colorectal or pancreatic cancer cells in the presence of the gpA33×CD3 bi-specific monovalent DART-1 and either human PBMC (E:T=25:1) or activated human T cells (E:T=10:1). gpA33×CD3 bi-specific monovalent diabody DART-1 exhibited potent redirected killing ability with concentrations required to achieve 50% maximal activity (EC50) in the sub-ng/mL to around 1 ng/mL range. In contrast, cytotoxicity was not observed when gpA33-negative cancer cell lines (e.g., HCT116) were employed. The results of the investigation are shown in FIG. 4A (colorectal cancer stem-like cells (Colon CSCL cells), FIG. 4B (Colo205 colorectal cells), and FIG. 4C (ASPC-1 pancreatic cancer cells). Results are summarized in Table 3.

TABLE 3

| Target Cell Line | EC50 of gpA33 × CD3 Bi-Specific Monovalent Diabody (ng/mL) | Effector:Target (E:T) | Max % Killing Observed |
|---|---|---|---|
| Colon CSLC | 0.9015 | 25:1 | 38 |
| Colo205 | 0.5853 | 10:1 | 35 |
| ASPC-1 | 1.142 | 10:1 | 25 |

Example 4

T Cell Activation in the Presence of gpA33×CD3 Bi-Specific Monovalent Diabodies

Figure 5A:
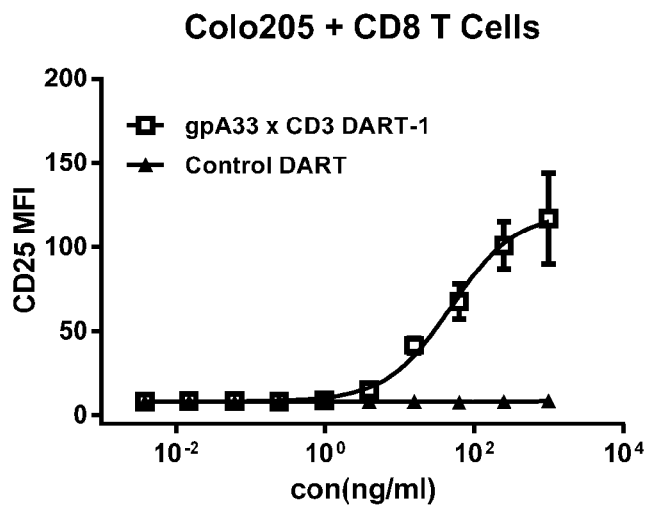
FIGS. 5A-5F show that activation of CD8 T cells occurred in the presence of the CD3 bi-specific monovalent diabody ("DART-1) only in the presence of cancer cells (FIGS. 5A-5C: CD8 T cells+colo205 cells (FIG. 5A), CD8 T cells+ASPC-1 cells (FIG. 5B), CD8 T cells alone (FIG. 5C)
Figure 5B:
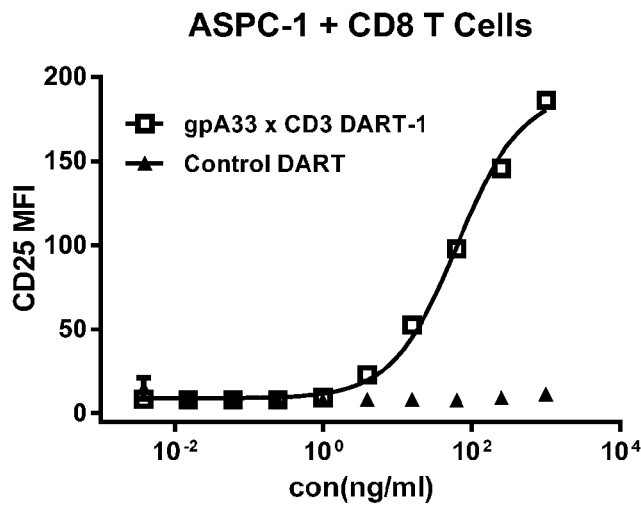
Figure 5C:
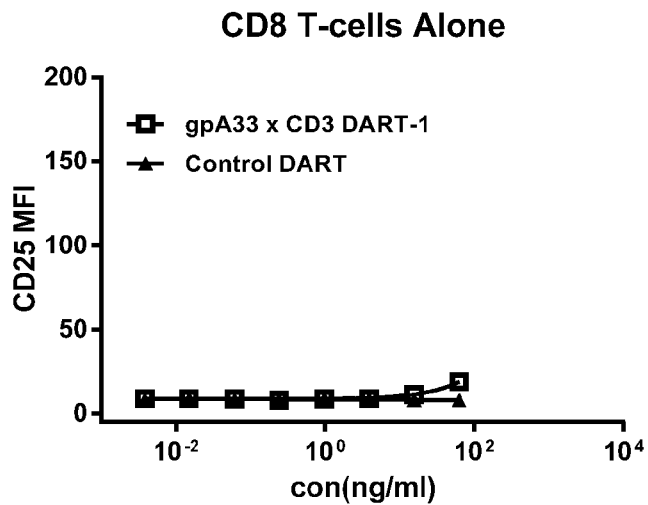
Figure 5D:
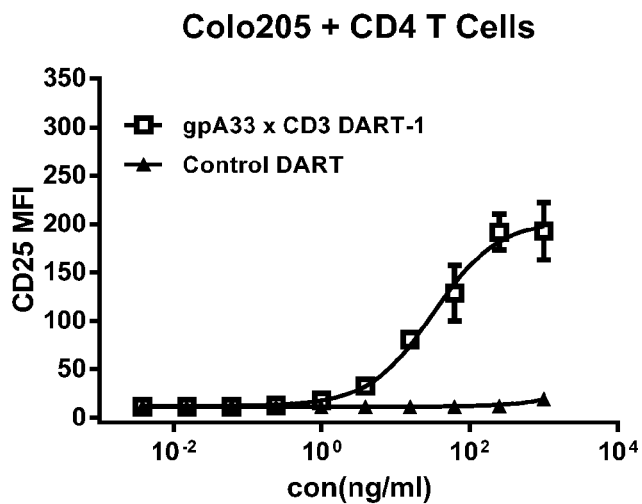
Figure 5E:
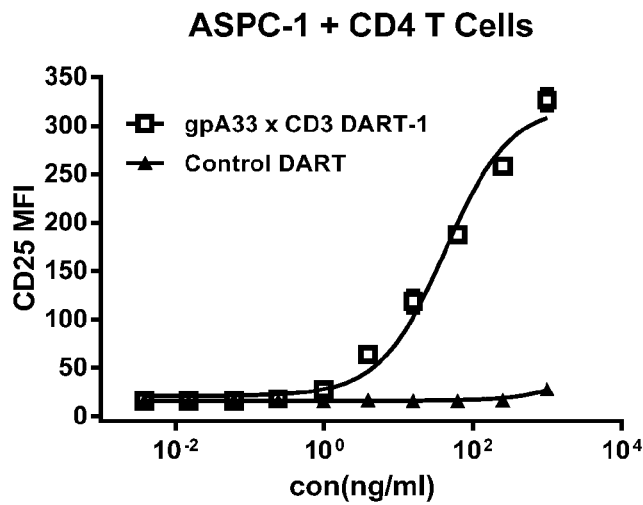
Figure 5F:
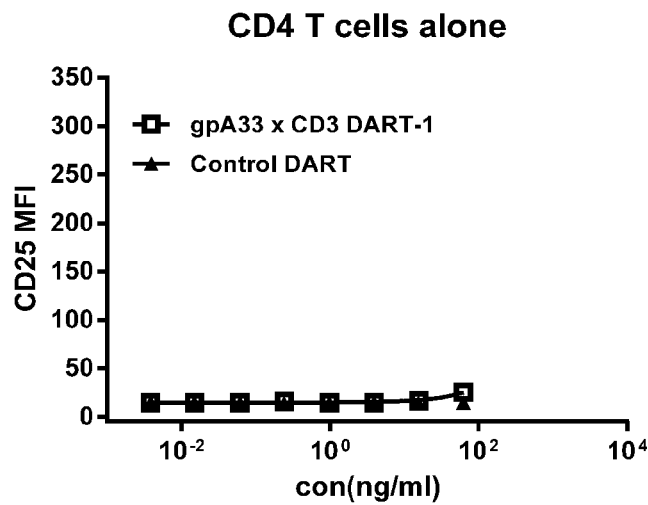

In order to further demonstrate the ability of the diabodies of the present invention to treat cancer, resting human T cells were incubated with the gpA33×CD3 bi-specific monovalent DART-1 in the presence or absence of cancer cells (colo205 or ASPC-1). To characterize T cell activation during gpA33×CD3 bi-specific monovalent diabody (DART-1)-mediated redirected killing process, T cells from redirected killing assays were stained for the T cell activation marker CD25 and analyzed by FACS. CD25 was upregulated in CD8 (FIGS. 5A-5B) and CD4 (FIGS. 5D-5E) T cells in a dose-dependent manner indicating that the gpA33×CD3 bi-specific monovalent diabodies induced T cell activation in the process of redirected killing. Conversely, in the absence of target cells there was no activation of CD8 (FIG. 5C) or CD4 (FIG. 5F) T cells indicating the gp-A33×CD3 diabodies do not activate T cells in the absence of target cells. Likewise, CD8 or CD4 T cells were not activated when incubated with target cells and a control bi-specific monovalent diabody (Control DART) (FIGS. 5A-5B, and FIGS. 5D-5F, respectively) indicating the requirement of cross-linking the T cell and target cell with the gpA33×CD3 bi-specific monovalent diabodies.

Example 5

Figure 6A:
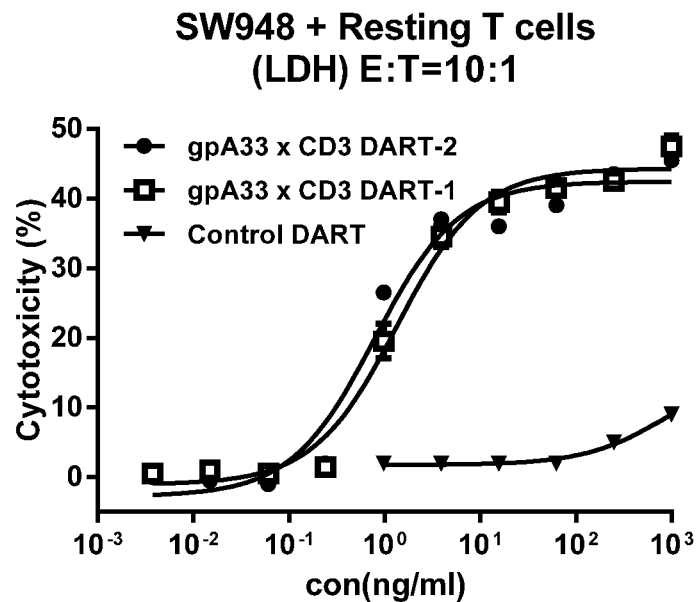
FIGS. 6A-6D demonstrate that gpA33×CD3 bi-specific monovalent diabodies (DART-1 and DART-2) mediated equivalent cytotoxicity for SW948 colorectal adenocarcinoma cells (FIG. 6A) and colo205 cells (FIG. 6B) and Colo205-Luc cells (FIG. 6C), and that neither diabody mediated cytotoxicity of the gpA33-negative cancer cell line, HCT116 (FIG. 6D).
Figure 6B:
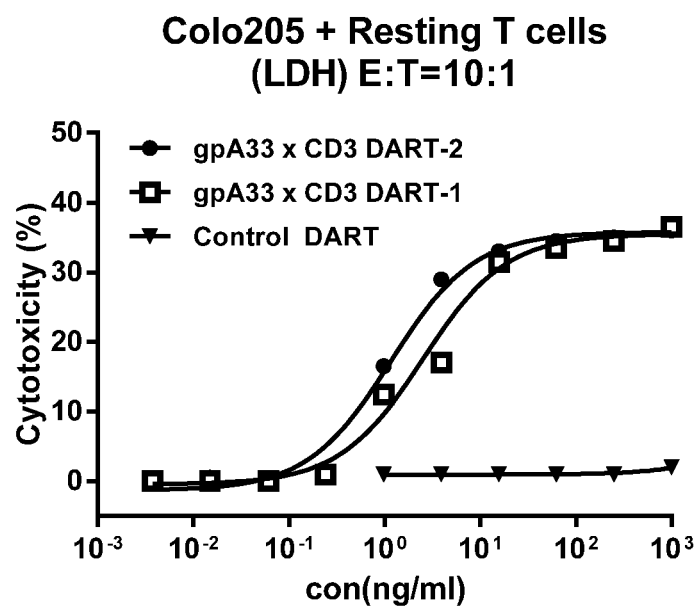
Figure 6C:
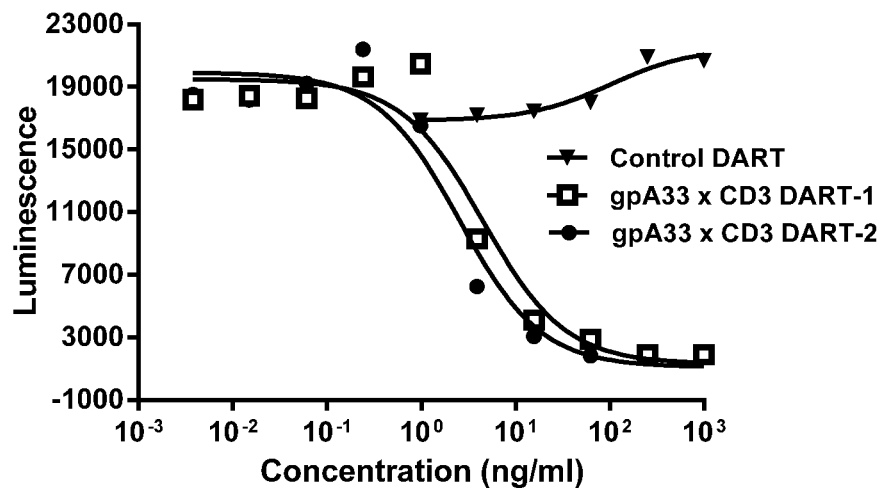
Figure 6D:
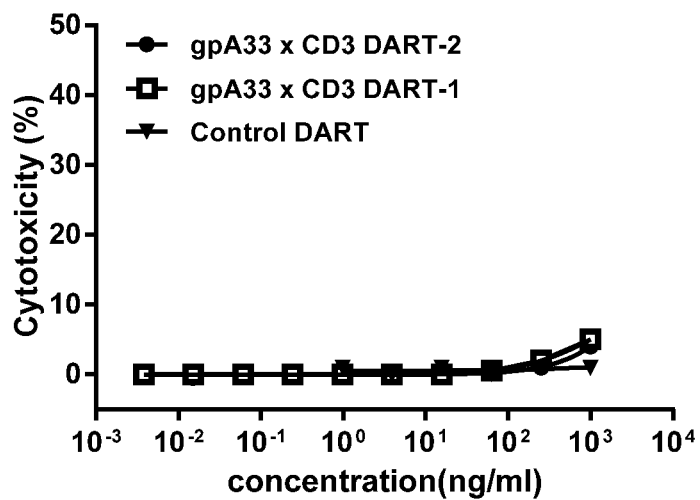

Equivalency of gpA33×CD3 Bi-Specific Monovalent Diabody (DART-1) Having Murine Anti-Human gpA33 Variable Domain Sequences and gpA33×CD3 Bi-Specific Monovalent Diabody (DART-2) Having Humanized Anti-Human gpA33 Variable Domain Sequences As discussed above, the gpA33×CD3 bi-specific monovalent diabody DART-1 contains $VL_{gpA33}$ and $VH_{gpA33}$ domains of a murine monoclonal antibody, whereas the gpA33×CD3 bi-specific monovalent diabody DART-2 contains humanized $VL_{gpA33}$ and humanized $VH_{gpA33}$ domains of the same murine antibody. In order to demonstrate the ability of the humanized $VL_{gpA33}$ and $VH_{gpA33}$ domains to promote T cell targeting to gpA33-expressing cancer cells, cancer cells that express gpA33 were incubated in the presence of resting T cells (LDH assay; E:T=10:1) in the presence of either DART-1, DART-1 or a control bi-specific monovalent diabody (Control DART). The results of this analysis (shown in FIGS. 6A-6D) demonstrate that DART-1 and DART-2 mediated equivalent cytotoxicity for SW948 colorectal adenocarcinoma cells (FIG. 6A) and colo205 cells (FIG. 6B). DART-1 and DART-2 both mediated cytotoxicity of a luciferase expressing Colo205 cell line which was stably transfected with firefly luciferase gene (luc2) (Colo205-Luc), as measured by decreased luminescence (FIG. 6C). Neither DART-1 nor DART-2 mediated cytotoxicity of the gpA33-negative cancer cell line, HCT116 (FIG. 6D). As shown in Table 4, DART-1 and DART-2 exhibited similar equivalent bioactivity against multiple tumor cell lines.

TABLE 4

| Effector/Target | | LDH Assay | | Luciferase Assay | |
| --- | --- | --- | --- | --- | --- |
| Donor T Cell | Tumor Cell Line | gpA33 × CD3 DART-2 | gpA33 × CD3 DART 1 | gpA33 × CD3 DART-2 | gpA33 × CD3 DART 1 |
| D54677 | SW948 | 0.79 | 1.34 | | |
| D54677 | Colo205 | 1.17 | 2.52 | | |
| D51031 | Colo205-Luc | 2.29 | 3.53 | 2.53 | 4.55 |
| D41440 | Colo205 | 2.29 | 3.37 | | |
| D41440 | Colo205-Luc | 2.80 | 4.26 | 2.57 | 3.26 |

Example 6

Cross-Reactivity of gpA33×CD3 Bi-Specific Monovalent Diabodies, gpA33×CD3 Bi-Specific Monovalent Diabodies Having an Albumin-Binding Domain and gpA33×CD3 Bi-Specific Monovalent Diabodies Having an IgG Fc Domain with PBMCs of Cynomolgus Monkey As shown above, the humanized $VL_{gpA33}$ and humanized $VH_{gpA33}$ domains of the gpA33×CD3 bi-specific monovalent diabody DART-2 mediate the cytotoxicity of gpA33-expressing cancer cells in the presence of human T cells. The $VL_{CD3}$ and $VH_{CD3}$ domains of the gpA33×CD3 bi-specific monovalent diabodies of the present invention were unexpectedly found to also be capable of binding to the CD3 of cynomolgus monkey T cells and redirect those cells to kill gpA33-expressing cells.

Figure 7A:
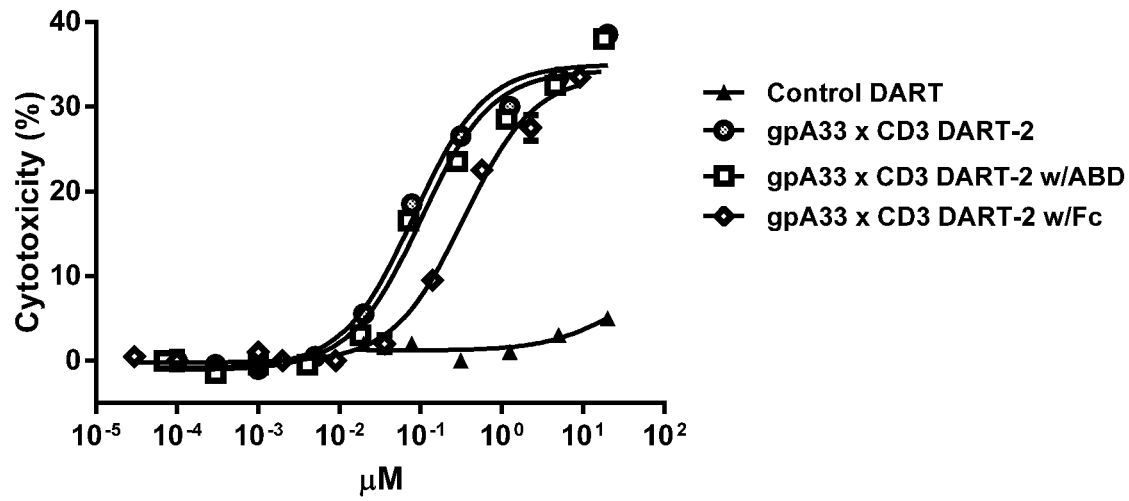
FIGS. 7A-7D demonstrate the ability of the gpA33×CD3 bi-specific monovalent diabody (DART-2), the gpA33×CD3 bi-specific monovalent diabody having an Albumin-Binding Domain (DART-2 with ABD "w/ABD") and the gpA33×CD3 bi-specific monovalent diabody having an immunoglobulin IgG Fc Domain (DART-2 with Fc "w/Fc") to promote the cytotoxicity of cancer cells in the presence of human or cynomolgus monkey PBMCs.
Figure 7B:
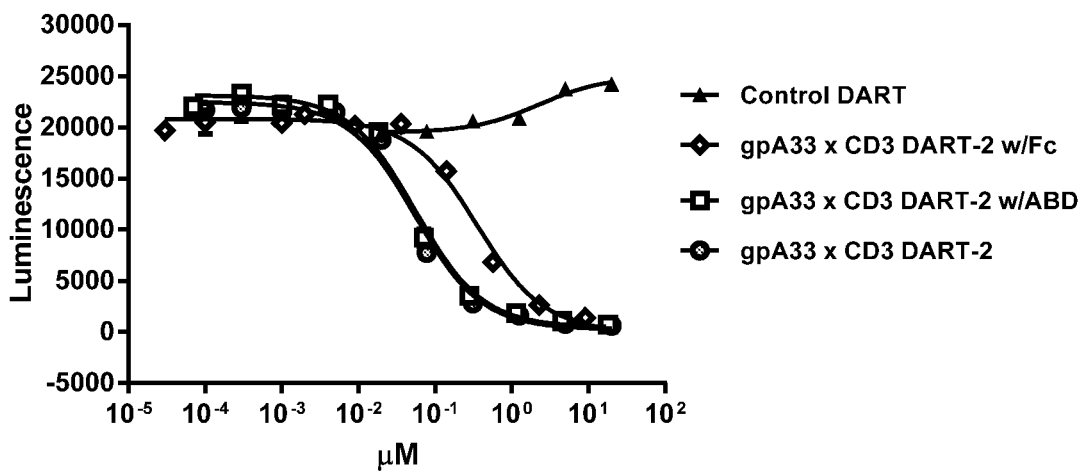
Figure 7C:
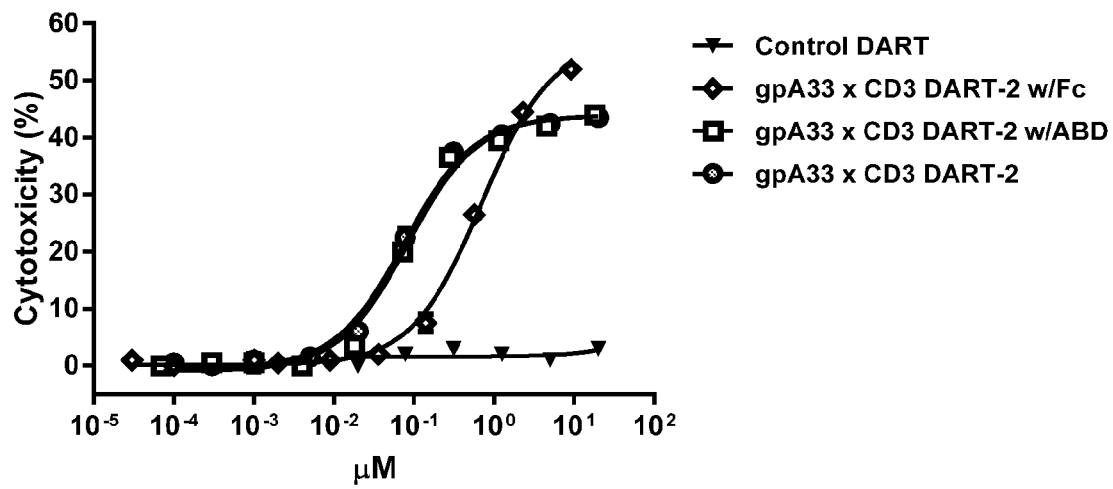
Figure 7D:
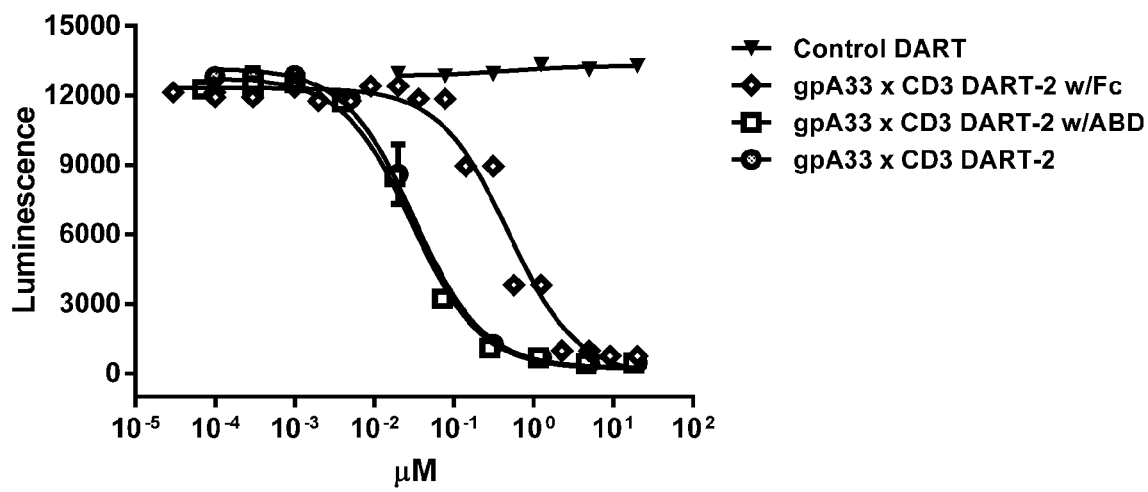

As shown in FIGS. 7A-7D, the gpA33×CD3 bi-specific monovalent DART-2 diabody, the gpA33×CD3 bi-specific monovalent diabody having an Albumin-Binding Domain (DART-2 w/ABD) and the gpA33×CD3 bi-specific monovalent DART-2 diabody having an IgG Fc Domain (DART-2 w/Fc) were all found to be capable of promoting the cytotoxicity of cancer cells in the presence of human or cynomolgus monkey PBMCs. FIGS. 7A-7B show the ability of the three diabodies to mediate cytotoxicity of Colo205-Luc cells that were incubated with human PBMC, as measured by LDH assay (FIG. 7A) or luciferase (FIG. 7B). FIGS. 7C-7D show the corresponding ability of the three diabodies to mediate cytotoxicity of Colo205-Luc cells that were incubated with cynomolgus monkey PBMC, as measured by LDH assay (FIG. 7A) or luciferase (FIG. 7B).

As shown in Table 5, the gpA33×CD3 bi-specific monovalent diabody DART-2 and the gpA33×CD3 bi-specific monovalent diabody having an Albumin-Binding Domain (DART-2 w/ABD) displayed comparable CTL activity. The bi-specific monovalent diabodies exhibited consistent activity with both human and cynomolgus monkey (cyno) PBMC effector cells.

TABLE 5

| | EC50 - CTL Activity (ng/mL) Colo205 Target Cells | | | |
| --- | --- | --- | --- | --- |
| | LDH Assay | | Luciferase Assay | |
| DART | Human PBMC | Cyno PBMC | Human PBMC | Cyno PBMC |
| gpA33 × CD3 bi-specific monovalent diabody (DART-2) | 4.09 | 3.81 | 2.73 | 1.55 |
| gpA33 × CD3 i-specific diabody having an Albumin-Binding Domain (DART-2 w/ABD) | 5.52 | 4.63 | 3.07 | 1.63 |

Example 7

In Vivo Reactivity of gpA33×CD3 Diabody in Murine Colon Tumor Model

In order to demonstrate the in vivo ability of the gpA33×CD3 diabodies of the present invention to provide a treatment for cancer, colo205 cells were co-implanted with activated T cells in immunodeficient NSG (NOD scid gamma) mice (Agliano, A. et al. (2008) "*Human Acute Leukemia Cells Injected In NOD/Ltsz-Scid/IL-2Rgamma Null Mice Generate A Faster And More Efficient Disease Compared To Other NOD/Scid-Related Strains*," Int. J. Cancer 123(9):2222-2227; Sanchez, P. V. et al. (2009) "*A Robust Xenotransplantation Model For Acute Myeloid Leukemia*," Leukemia 23(11):2109-2117; Racki, W. J. et al. (2010) "*NOD-Scid IL2rgamma(Null) Mouse Model Of Human Skin Transplantation And Allograft Rejection*," Transplantation 89(5):527-536; Choi, B. et al. (2011) "*Human B Cell Development And Antibody Production In Humanized NOD/SCID/IL-2Rγ(Null) (NSG) Mice Conditioned By Busulfan*," J. Clin. Immunol. 31(2):253-264; Sartelet, H. et al. (2012) "*Description Of A New Xenograft Model Of Metastatic Neuroblastoma Using NOD/SCID/Il2rg Null (NSG) Mice*," In Vivo 26(1):19-29; Spranger, S. et al. (2012) "*NOD/scid IL-2Rg(null) Mice: A Preclinical Model System To Evaluate Human Dendritic Cell-Based Vaccine Strategies in vivo*," J. Transl. Med. 10:30; von Bonin, M. et al. (2013) "*in vivo Expansion Of Co-Transplanted T Cells Impacts On Tumor Re-Initiating Activity Of Human Acute Myeloid Leukemia In NSG Mice*," PLoS One. 8(4):e60680).

Figure 8:
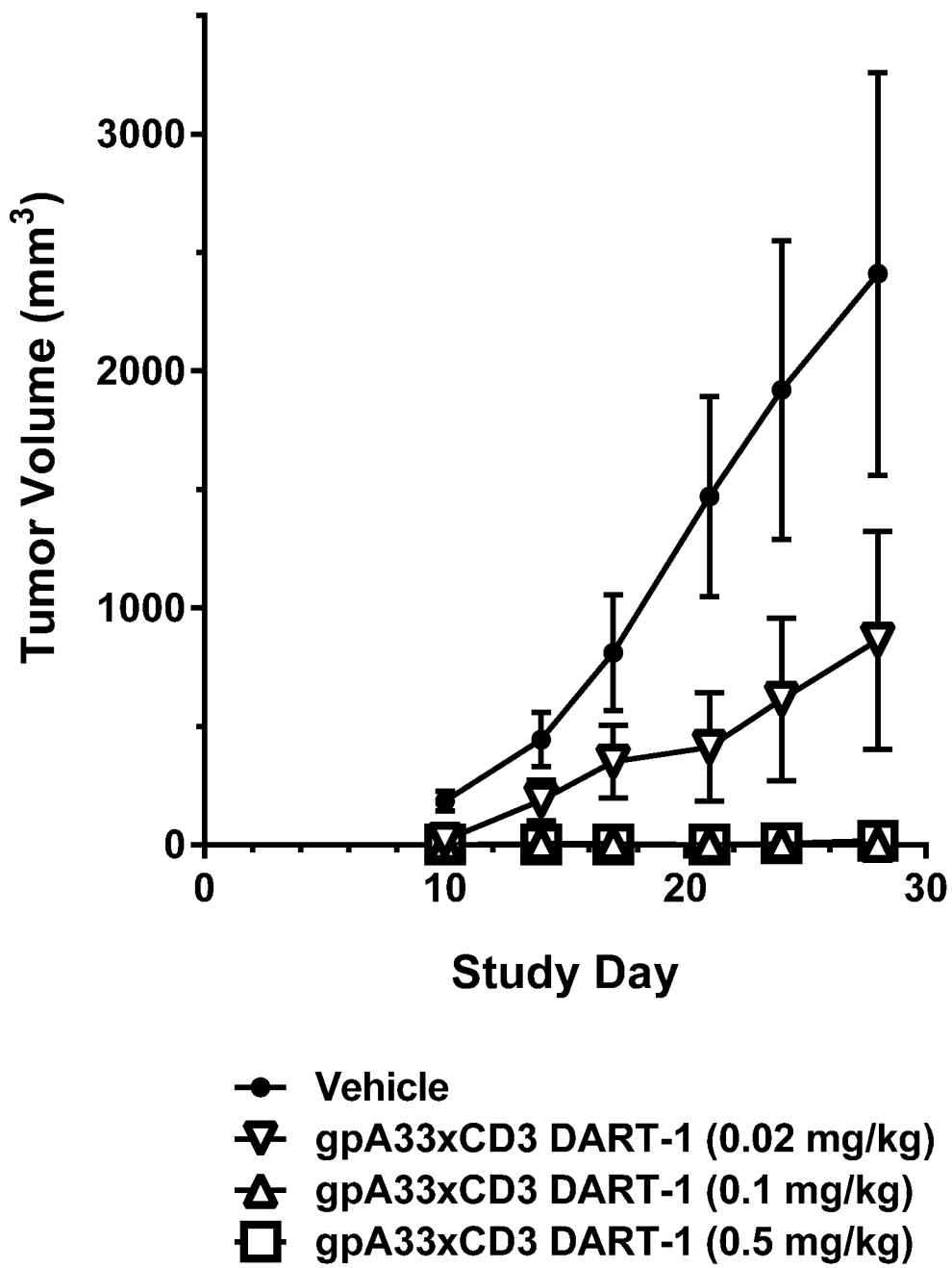
FIG. 8 demonstrates the in vivo ability of the gpA33×CD3 bi-specific monovalent diabody (DART-1) to decrease tumor volume in a murine Colo205 colon cancer model.

The gpA33×CD3 bi-specific monovalent diabody DART-1 was administered IV to the mice for once daily for 4 days (QD×4) starting at implantation. Colo205 tumor volume was found to increase in mice receiving the Vehicle control (FIG. 8). However, animals receiving DART-1 were found to exhibit lower or no Colo205 tumor volume (FIG. 8).

Imaging of NSG mice implanted with Colo205 cells showed that at day 2 of treatment mice receiving Vehicle (FIG. 9A) or the gpA33×CD3 bi-specific monovalent diabody DART-1 (FIG. 9B) had significant tumors. However, at day 12 of treatment mice receiving the gpA33×CD3 bi-specific monovalent diabody DART-1 had dramatically lower tumor volumes (FIG. 9D). At day 12 of treatment, mice receiving Vehicle showed increased tumor volume (FIG. 9C).

Figure 10:
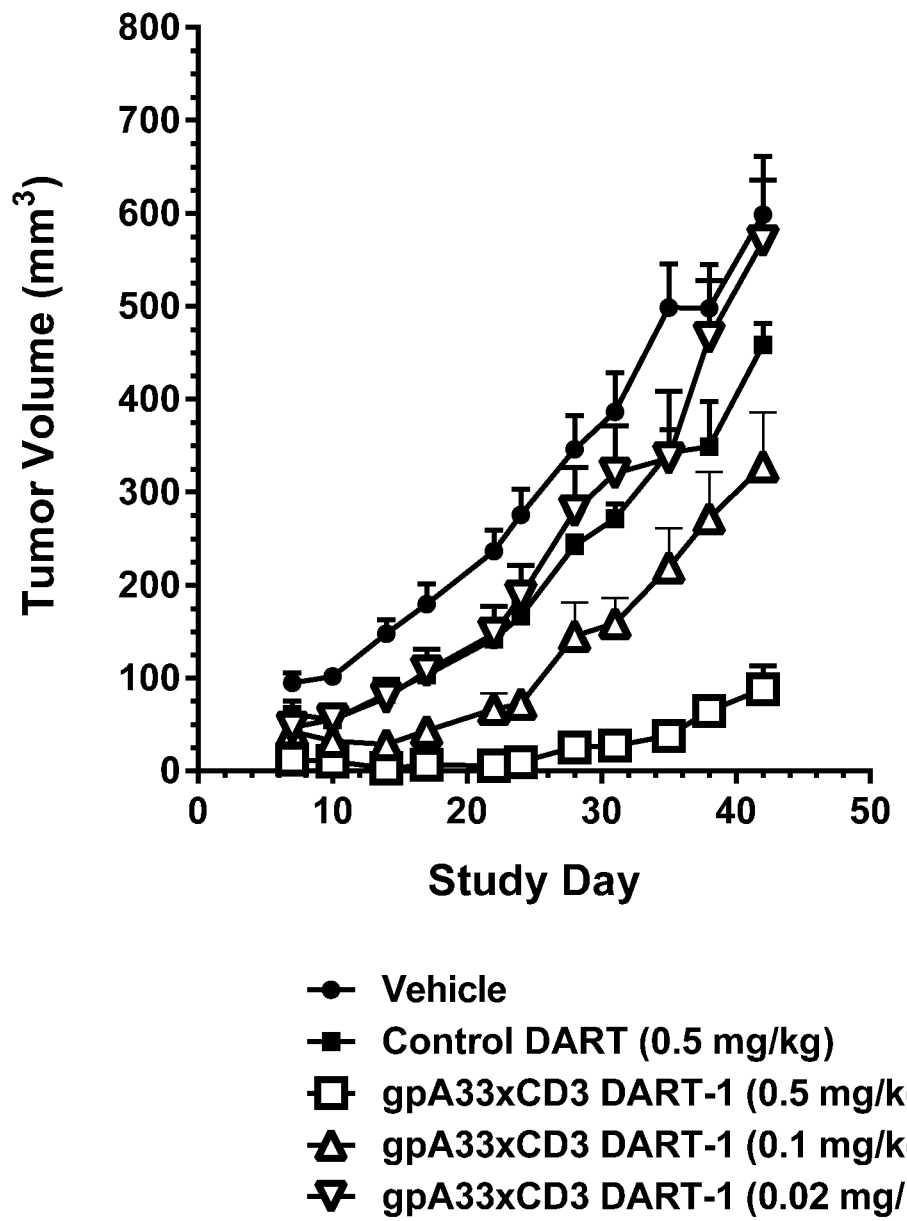
FIG. 10 demonstrates the in vivo ability of the gpA33×CD3 bi-specific monovalent diabody (DART-1) to decrease tumor volume in a murine ASPC-1 pancreatic cancer model.

As further evidence of the in vivo ability of the gpA33×CD3 diabodies of the present invention to provide a treatment for cancer, the above-described tumor model was conducted using ASPC-1 pancreatic tumor cells and activated human T cells (E:T=1:1). The gpA33×CD3 bi-specific monovalent diabody DART-1, a control bi-specific monovalent diabody (Control DART), or Vehicle were administered IV for once daily for 9 days (QD×9) starting at implantation. ASPC-1 tumor volume was found to increase in mice receiving the Vehicle control (FIG. 10). However, animals receiving DART-1 were found to exhibit lower tumor volume, in a dose-dependent manner (FIG. 10).

Example 8

Efficacy Determination of gpA33×CD3 Bi-Specific Monovalent Diabody Having an IgG Fc Domain Version 1 (DART-2 w/Fc Version 1)

In order to determine the efficacy of the gpA33×CD3 bi-specific monovalent diabody having an IgG Fc Domain version 1 (DART-2 w/Fc Version 1), mice were infused (using osmotic pumps) for 7 days with the above-described DART-2 w/Fc Version 1 at various dosage levels. 48 h after pump implantation (i.e., in the presence of a steady-state circulating level of DART-2 w/Fc Version 1), a mixture of Colo205 tumor cells and T cells were implanted subcutaneously into the mice, and the extent of tumor growth was monitored. Table 6 summarizes the design of the study; each group contained 8 female mice.

TABLE 6

| Group | Treatment | Dose (mg/kg) | Route/Schedule | Cell Implant(s) |
|---|---|---|---|---|
| 1 | Vehicle | 0 | IV/QDx5 | COLO205 (5E6) |
| 2 | gpA33 × CD3 bi-specific monovalent diabody having an IgG Fc Domain (DART-2 w/Fc Version 1) | 3.1 | IP/CIF | COLO205 (5E6) hT-cells (5E6) |
| 3 | DART-2 w/Fc Version 1 | 1.5 | IP/CIF | COLO205 (5E6) hT-cells (5E6) |
| 4 | DART-2 w/Fc Version 1 | 0.75 | IP/CIF | COLO205 (5E6) hT-cells (5E6) |
| 5 | DART-2 w/Fc Version 1 | 0.375 | IP/CIF | COLO205 (5E6) hT-cells (5E6) |
| 6 | DART-2 w/Fc Version 1 | 0.5 | IV/QDx5 | COLO205 (5E6) hT-cells (5E6) |

Figure 11:
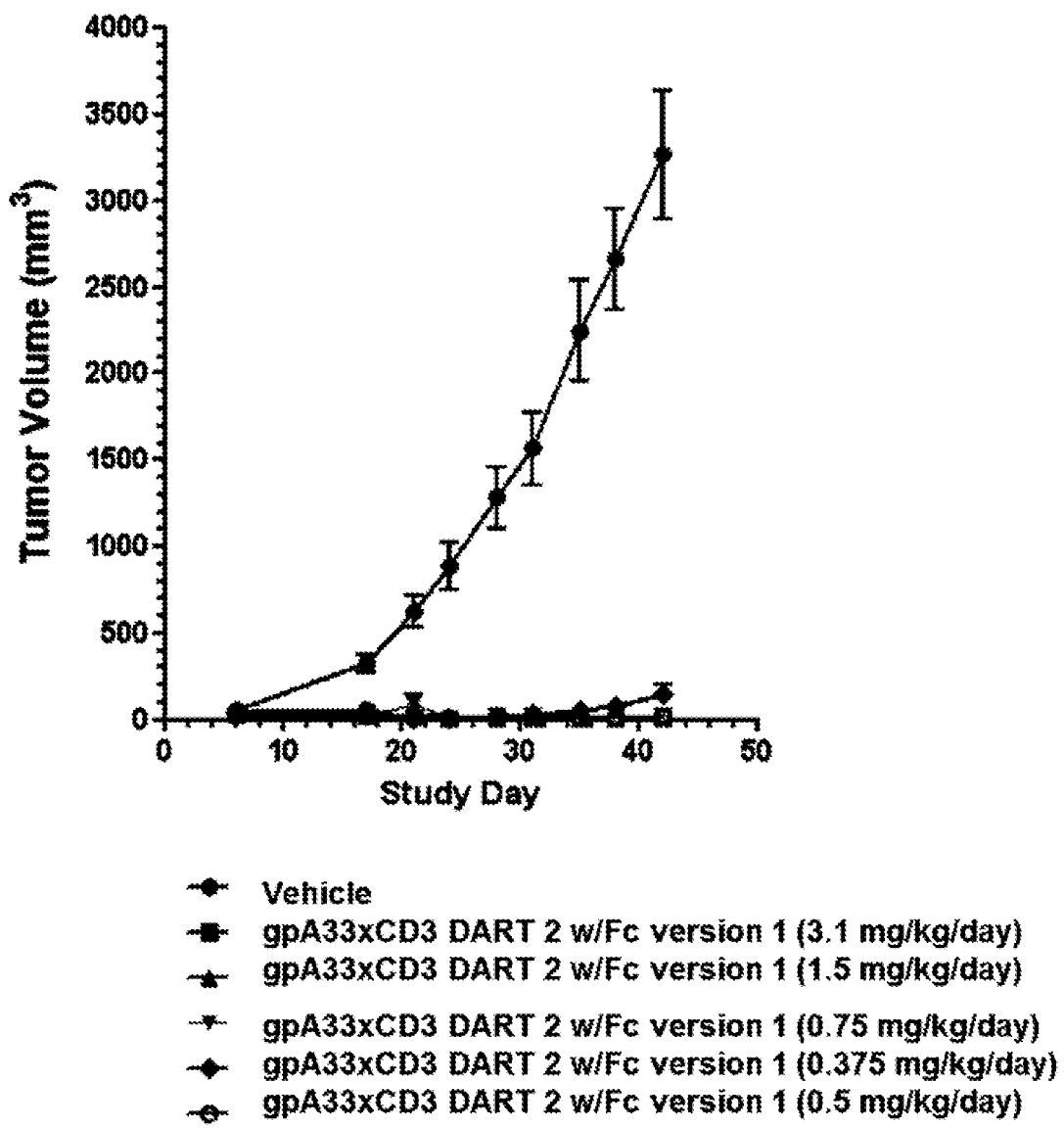
FIG. 11 shows the ability of the gpA33×CD3 bi-specific monovalent diabody having an immunoglobulin IgG Fc Domain (DART-2 w/Fc Version 1) to mediate a dramatic reduction in tumor volume in an in vivo colon cancer model.

The results of this study are shown in FIG. 11, and indicate that the administration of the above-described gpA33×CD3 bi-specific monovalent diabodies having an IgG Fc Domain (DART-2 w/Fc Version 1) mediated a dramatic reduction in tumor volume at all tested dosages.

In light of the dramatic reduction in tumor volume obtained in the above study, a further study was conducted to assess efficacy at much lower doses. Table 7 summarizes the design of this further study; each group contained 8 female mice.

TABLE 7

| Group | Treatment | Dose (mg/kg) | Route/Schedule | Cell Implant(s) |
|---|---|---|---|---|
| 1 | Vehicle | 0 | IV/QDx5 | COLO205 (5E6) |
| 2 | gpA33 × CD3 bi-specific monovalent diabody having an IgG Fc Domain (DART-2 w/Fc Version 1) | 0.2 | IP/CIF | COLO205 (5E6) hT-cells (5E6) |
| 3 | DART-2 w/Fc Version 1 | 0.04 | IP/CIF | COLO205 (5E6) hT-cells (5E6) |
| 4 | DART-2 w/Fc Version 1 | 0.008 | IP/CIF | COLO205 (5E6) hT-cells (5E6) |
| 5 | DART-2 w/Fc Version 1 | 0.0016 | IP/CIF | COLO205 (5E6) hT-cells (5E6) |
| 6 | DART-2 w/Fc Version 1 | 0.5 | IV/QDx5 | COLO205 (5E6) hT-cells (5E6) |

Figure 12:
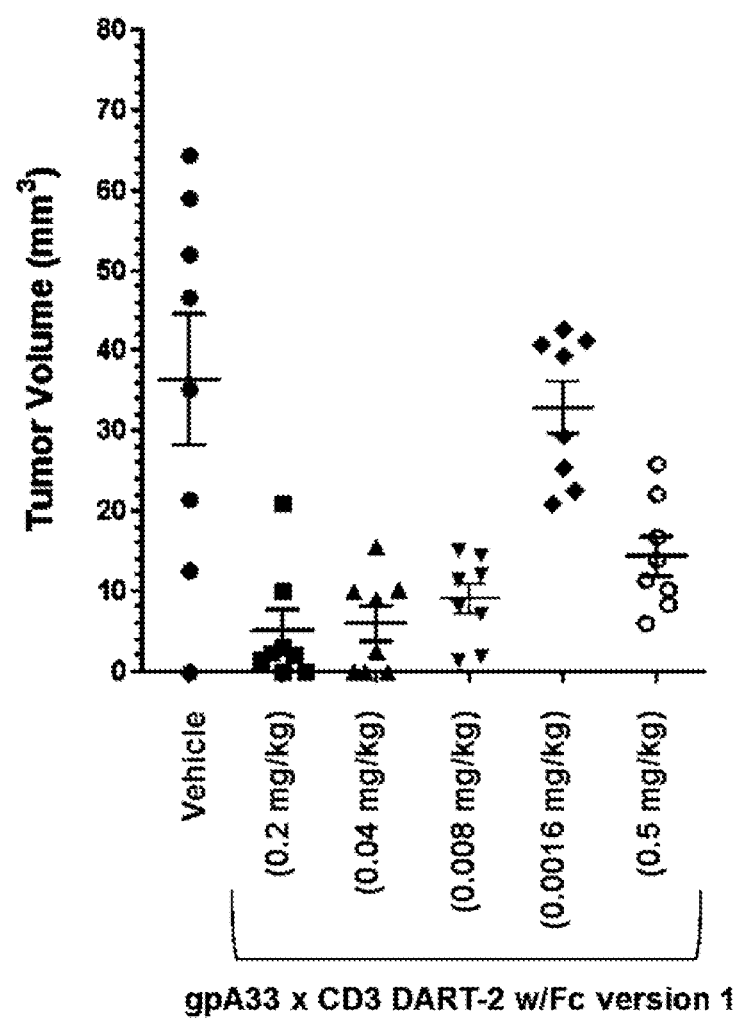
FIG. 12 shows the ability of the gpA33×CD3 bi-specific monovalent diabody having an immunoglobulin IgG Fc Domain (DART-2 w/Fc Version 1) to mediate a reduction in tumor volume in an in vivo colon cancer model even at extremely low doses.

The results of this further study are shown in FIG. 12. In FIG. 12, each symbol denotes an animal that received the indicated dosage of the above-described gpA33×CD3 bi-specific monovalent diabody having an IgG Fc Domain (DART-2 w/Fc Version 1) or Vehicle. The data show efficacy at all tested dosages.

Example 9

Pharmacokinetic Profile of gpA33×CD3 Bi-Specific Monovalent Diabody (DART-2) and gpA33×CD3 Bi-Specific Monovalent Diabody Having an IgG Fc Domain (DART-2 w/Fc) in Cynomolgus Monkey The ability of the $VL_{CD3}$ and $VH_{CD3}$ domains of the diabodies of the present invention to bind to the CD3 of cynomolgus monkey permits the use of such animals to measure the in vivo pharmacokinetics of the diabodies of the present invention.

Figure 13:
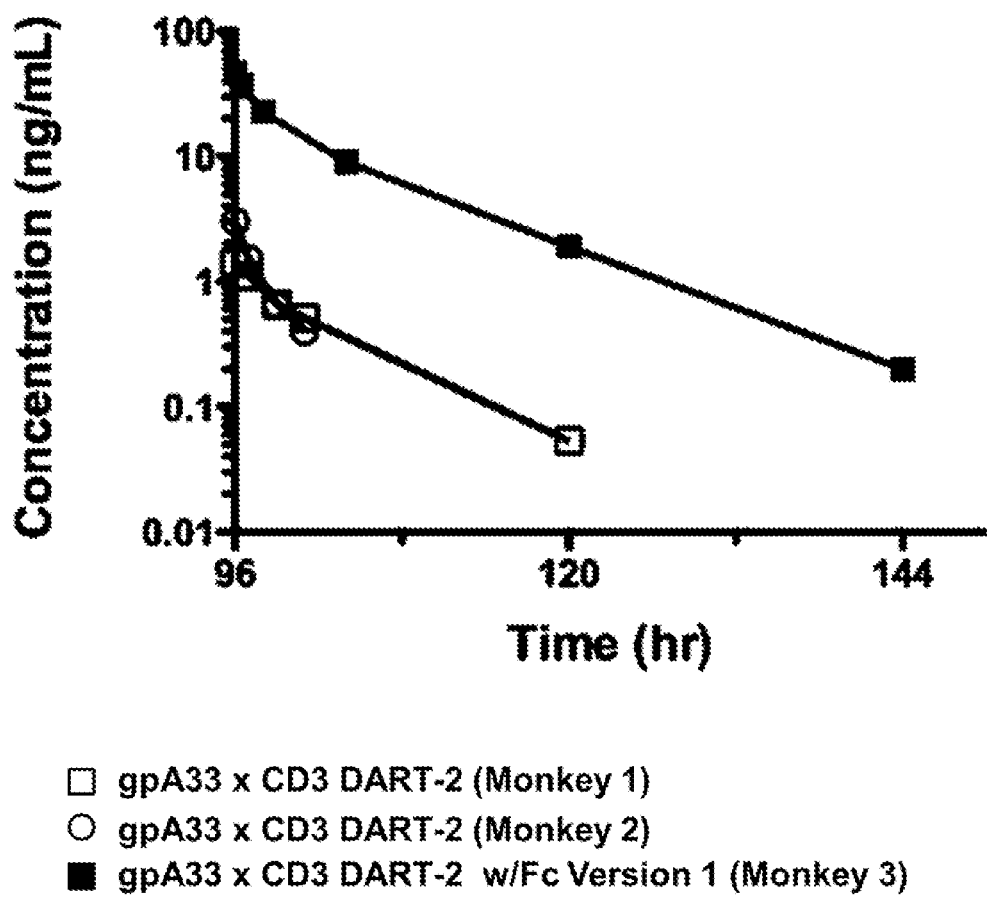
FIG. 13 shows the pharmacokinetics of the gpA33×CD3 bi-specific monovalent diabody (DART-2), and gpA33×CD3 bi-specific monovalent diabody having an immunoglobulin IgG Fc Domain (DART-2 w/Fc Version 1) diabodies in cynomolgus monkeys.

To measure such pharmacokinetics, the above-described gpA33×CD3 bi-specific monovalent diabody (DART-2) or gpA33×CD3 bi-specific monovalent diabody having an IgG Fc Domain (DART-2 w/Fc Version 1) were injected into cynomolgus monkeys (10 μg/kg/day) and the concentration of such molecules remaining in the circulation was monitored. FIG. 13 shows the result of this study, and indicates that DART-2 and DART-2 w/Fc Version 1 exhibit first-order elimination kinetics.

Example 10

SPR Analysis of gpA33×CD3 Bi-Specific Monovalent Fc Diabody (DART-1 w/Fc Version 1) Binding to Human and Cynomolgus Monkey CD3 and gpA33 gpA33×CD3 bi-specific Fc diabody (DART-2 w/Fc Version 1) binding to soluble versions of human and cynomolgus monkey CD3 receptor was analyzed by SPR on a BIAcore 3000 biosensor (GE, Healthcare). Receptors were immobilized on the CM5 sensor chip according to the procedure recommended by the manufacturer. Briefly, the carboxyl groups on the sensor chip surface were activated with an injection of a solution containing 0.2M N-ethyl-N-(3diethylamino-propyl) carbodiimide and 0.05M N-hydroxysuccinimide. Soluble CD3 receptor (1 µg/ml) was then injected over the activated CM5 surface in 10 mM sodium-acetate, pH 5.0, at flow rate 5 µL/min, followed by 1 M ethanolamine for deactivation.

The soluble versions of cynomolgus and human CD3 employed in such analysis were expressed in mammalian cells as a CD3ε/CD3δ heterodimer, stabilized by oppositely charged heterodimer-promoting E-coil and K-coil sequences at their C-termini. The soluble cynomolgus CD3ε contained the first 118 amino acid residues of cynomolgus monkey CD3ε, with the V35 allele (FN18+) followed by the above-described E-coil Domain (SEQ ID NO:3) at the carboxy terminus. The amino acid sequence of the V35 allele (FN18+) cynomolgus CD3ε is (SEQ ID NO:49):

```
MQSGTRWRVL GLCLLSIGVW GQDGNEEMGS ITQTPYQVSI

SGTTVILTCS QHLGSEAQWQ HNGKNKEDSG DRLFLPEFSE

MEQSGYYVCY PRGSNPEDAS HHLYLKARVC ENCMEMDVMA

VATIVIVDIC ITLGLLLLVY YWSKNRKAKA KPVTRGAGAG

GRQRGQNKER PPPVPNPDYE PIRKGQQDLY SGLNQRRI
```

The soluble cynomolgus CD3δ contained the first 101 amino acid residues of cynomolgus monkey CD3δ followed by the above-described K-coil Domain (SEQ ID NO:4) at the carboxy terminus. The amino acid sequence of the cynomolgus CD3δ is (SEQ ID NO:50):

```
MEHSTFLSGL VLATLLSQVS PFKIPVEELE DRVFVKCNTS

VTWVEGTVGT LLTNNTRLDL GKRILDPRGI YRCNGTDIYK

DKESAVQVHY RMCQNCVELD PATLAGIIVT DVIATLLLAL

GVFCFAGHET GRLSGAADTQ ALLRNDQVYQ PLRDRDDAQY

SRLGGNWARN K
```

The two proteins were co-expressed in mammalian CHO-S cells and purified using an anti-E/K-coil mAb coupled to SEPHAROSE®.

The soluble human CD3ε contained residues 1-127 of human CD3ε with C119S and C122S, followed by the above-described E-coil Domain (SEQ ID NO:3) at the carboxy terminus. The amino acid sequence of human CD3ε is (SEQ ID NO:51):

```
MQSGTHWRVL GLCLLSVGVW GQDGNEEMGG ITQTPYKVSI

SGTTVILTCP QYPGSEILWQ HNDKNIGGDE DDKNIGSDED

HLSLKEFSEL EQSGYYVCYP RGSKPEDANF YLYLRARVCE

NCMEMDVMSV ATIVIVDICI TGGLLLLVYY WSKNRKAKAK

PVTRGAGAGG RQRGQNKERP PPVPNPDYEP IRKGQRDLYS

GLNQRRI
```

The soluble human CD3δ contained residues 1-101 of human CD3δ followed by the above-described K-coil Domain (SEQ ID NO:4) at the carboxy terminus. The two proteins were co-expressed in mammalian CHO-S cells and purified using an anti-E/K-coil affinity column. The amino acid sequence of human CD3δ is (SEQ ID NO:52):

```
FKIPIEELE DRVFVNCNTS ITWVEGTVGT LLSDITRLDL

GKRILDPRGI YRCNGTDIYK DKESTVQVHY RMCQSCVELD

PATVAGIIVT DVIATLLLAL GVFCFAGHET GRLSGAADTQ

ALLRNDQVYQ PLRDRDDAQY SHLGGNWARN K
```

The soluble human gpA33 contained residues 1-235 of human gpA33 with (SEQ ID NO:53) HHHHHH ("6His") repeats at the carboxy terminal end. The soluble cynomolgus gpA33 contained residues 1-314 of cynomolgus monkey gpA33 Met 1 to Gln 314 with 6 His repeats at the carboxy terminal end. The proteins were expressed in mammalian CHO-S cells and purified using Ni SEPHAROSE®.

Binding experiments were performed in HBS-EP buffer, which contains 10 mM HEPES, pH 7.4, 150 mM NaCl, 3 mM EDTA and 0.005% P20 surfactant. Binding of DART-2 w/Fc Version 1 was analyzed (in duplicate) at concentrations of 0, 6.25, 12.5, 25, 50 and 100 nM, injected for 120 sec at a flow rate of 30 µL/min.

Regeneration of the immobilized receptor surfaces was performed by pulse injection of 10 mM glycine, pH 1.5. Reference curves were obtained by injection of each dilution of DART-2 w/Fc over the treated surface with no immobilized protein. Binding curves at zero concentration were subtracted as a blank. KD values were determined by a global fit of binding curves to the Langmuir 1:1 binding model (BIAevaluation™ software v4.1).

Figure 14A:
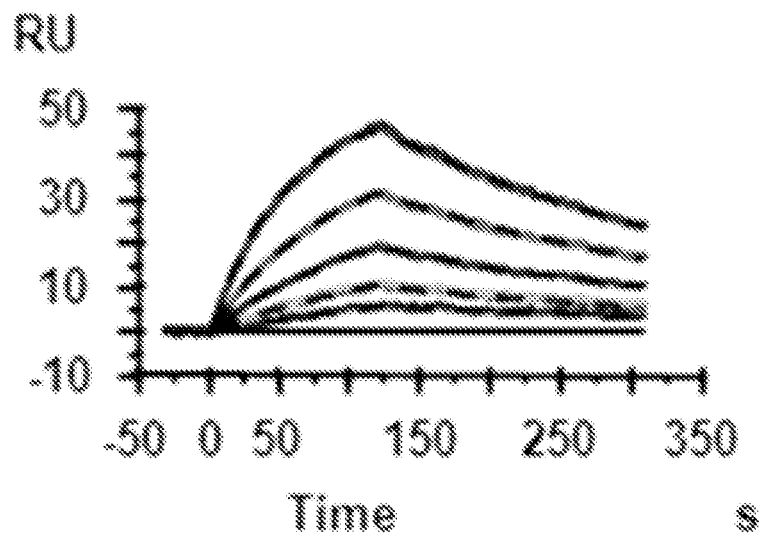
FIGS. 14A-14B show SPR analysis of the binding of DART-2 w/Fc Version 1 to immobilized human and cynomolgus monkey CD3. The black dashed lines represent the global fit to a 1:1 Langmuir model of binding curves obtained at DART-2 w/Fc concentrations of 0, 6.25, 12.5, 25, 50 or 100 nM. The data are representative of three independent experiments.
Figure 14B:
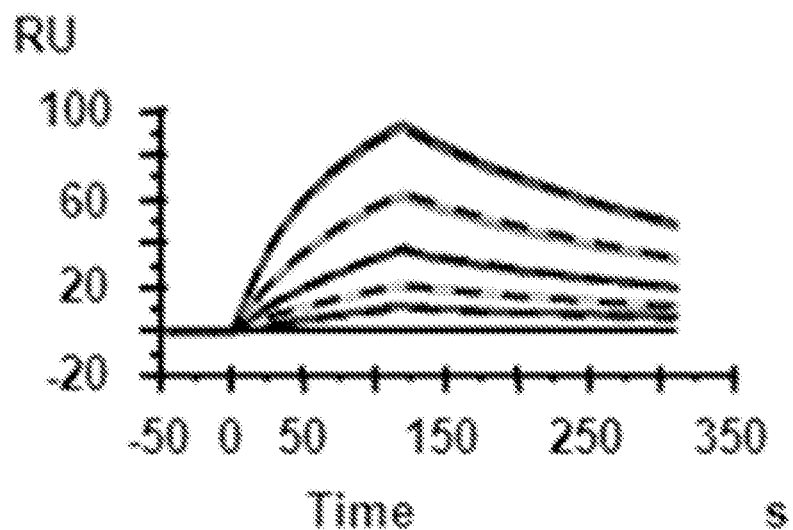
Figure 15A:
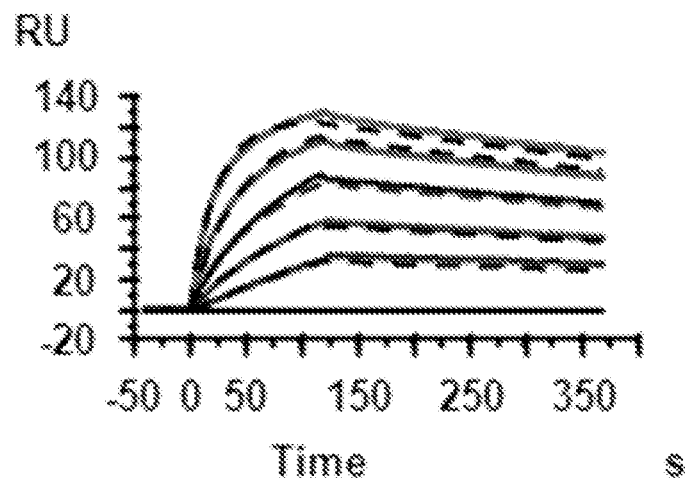
FIGS. 15A-15B show SPR analysis of the binding of DART-2 w/Fc Version 1 to captured human and cynomolgus monkey gpA33. The black dashed lines represent the global fit to a 1:1 Langmuir model of binding curves obtained at DART-2 w/Fc Version 1 concentration of 0, 6.25, 12.5, 25, 50 or 100 nM. The data are representative of three independent experiments.
Figure 15B:
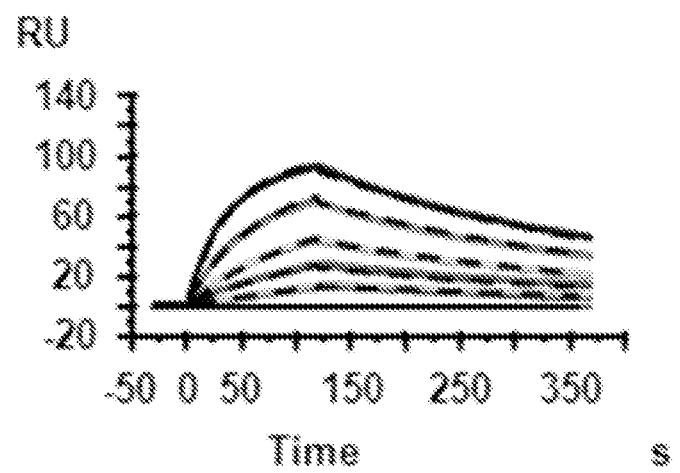

The SPR analysis of gpA33×CD3 bi-specific Fc diabody (DART-2 w/Fc Version 1) binding to human and cynomolgus monkey CD3 and gpA33 demonstrated a substantial similarity for the molecules from the two different species (FIGS. 14A-14B; FIGS. 15A-15B). Table 8 provides the equilibrium dissociation constants (KDs) calculated by global fit to a 1:1 Langmuir model affinity and kinetic constants for DART-2 w/Fc interactions. The KD values of DART-2 w/Fc Version 1 for human and cynomolgus monkey CD3 are nearly identical at 23 and 26 nM, respectively, despite some difference in the maximal binding responses between the two antigens. Random orientation of antigens with different amino acid sequences directly immobilized on the surface can result in different densities of available binding sites on the surface. The KD values for the interaction of DART-2 w/Fc Version 1 with human and monkey gpA33 are 2.2 nM and 12 nM, respectively (Table 8). The difference in affinity is the result of a relatively small decrease in association rate constant and increase in dissociation rate constant for the interaction of DART-2 w/Fc Version 1 with cynomolgus monkey gpA33 (Table 8). The data are averages of three independent experiments in duplicates (SD=standard deviation; h, human; cyno, cynomolgus monkey).

TABLE 8

Equilibrium Dissociation Constants (KD) For The Binding Of DART-2 W/Fc Version 1 To Antigens From Different Species

| Antigens | $k_a$ (±SD) $(M^{-1}s^{-1})$ | $k_d$ (±SD) $(s^{-1})$ | $K_D$ (±SD) (nM) |
|---|---|---|---|
| hCD3ε/δ | 1.5(±0.1) × $10^5$ | 3.5(±0.06) × $10^{-3}$ | 23 ± 2.0 |
| cynoCD3ε/δ | 1.3(±0.02) × $10^5$ | 3.4(±0.02) × $10^{-3}$ | 26 ± 0.6 |
| hgpA33-His | 4.2(±0.3) × $10^5$ | 9.0(±0.5) × $10^{-4}$ | 2.2 ± 0.2 |
| cynogpA33-His | 2.3(±0.2) × $10^5$ | 2.8(±0.1) × $10^{-3}$ | 12 ± 1.0 |

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A bi-specific monovalent diabody, wherein said bi-specific monovalent diabody is capable of specific binding to an epitope of gpA33 and to an epitope of CD3, wherein the bi-specific monovalent diabody comprises a first polypeptide chain and a second polypeptide chain, wherein said first and second polypeptide chains are covalently bonded to one another, and wherein:

A. the first polypeptide chain comprises, in the N-terminal to C-terminal direction:
  i. a Domain 1, comprising a sub-Domain (1A), which comprises a VL Domain of a monoclonal antibody capable of binding to CD3 ($VL_{CD3}$) (SEQ ID NO:5); and a sub-Domain (1B), which comprises a VH Domain of a monoclonal antibody capable of binding to gpA33 ($VH_{gpA33}$) (SEQ ID NO:27); wherein said sub-Domains (1A) and (1B) are separated from one another by a peptide linker (SEQ ID NO:1);
  ii. a Domain 2, wherein said Domain 2 is a K-coil Domain (SEQ ID NO:4) or an E-coil Domain (SEQ ID NO:3), wherein said Domain 2 is separated from said Domain 1 by a peptide linker (SEQ ID NO:2);

B. the second polypeptide chain comprises, in the N-terminal to C-terminal direction:
  i. a Domain 1, comprising a sub-Domain (1A), which comprises a VL Domain of a monoclonal antibody capable of binding to gpA33 ($VL_{gpA33}$) (SEQ ID NO:26) and a sub-Domain (1B), which comprises a VH Domain of a monoclonal antibody capable of binding to CD3 ($VH_{CD3}$) (SEQ ID NO:25), wherein said sub-Domains (1A) and (1B) are separated from one another by a peptide linker (SEQ ID NO:1);
  ii. a Domain 2, wherein said Domain 2 is an E-coil Domain (SEQ ID NO:3) or a K-coil Domain (SEQ ID NO:4), wherein said Domain 2 is separated from said Domain 1 by a peptide linker (SEQ ID NO:2); and wherein said Domain 2 of said first polypeptide chain and said Domain 2 of said second polypeptide chain are not both E-coil Domains or both K-coil Domains;

and wherein:
(a) said VL Domain of said first polypeptide chain and said VH Domain of said second polypeptide chain form an Antigen Binding Domain capable of specific binding to an epitope of CD3; and
(b) said VH Domain of said first polypeptide chain and said VL Domain of said second polypeptide chain form an Antigen Binding Domain capable of specific binding to an epitope of gpA33.

2. The bi-specific monovalent diabody of claim 1, wherein said first polypeptide chain comprises, an Albumin-Binding Domain (SEQ ID NO:34), said Albumin-Binding Domain being positioned C-terminally to said Domain 2, and separated from said Domain 2 by a Linker 3 (SEQ ID NO:32).

3. The bi-specific monovalent diabody of claim 1, wherein:

A. said second polypeptide chain additionally comprises:

iii. a Domain 3, comprising a sub-Domain (3A), which comprises a cysteine-containing peptide (Peptide 1) (SEQ ID NO:39) and a sub-Domain (3B), which comprises a polypeptide portion of an IgG Fc Domain having CH2 and CH3 domains of an IgG immunoglobulin Fc Domain; wherein:

(1) said Domain 3 is positioned C-terminally to said Domain 2, and is separated from said Domain 2 by a spacer peptide having sequence GGG (Linker 5); or (2) said Domain 3 is positioned N-terminally to said Domain 1, and is separated from said Domain 1 by a spacer peptide (Linker 4) (SEQ ID NO:38); and C. said bi-specific monovalent diabody additionally comprises a third polypeptide chain that comprises, in the N-terminal to C-terminal direction, a Domain 3 comprising:

(1) a sub-Domain (3A), which comprises a cysteine-containing peptide (Peptide 1) (SEQ ID NO:39); and (2) a sub-Domain (3B), which comprises a polypeptide portion of an IgG Fc Domain having CH2 and CH3 domains of an IgG immunoglobulin Fc Domain;

and wherein said polypeptide portions of the IgG Fc Domains of said second and third polypeptide chains form said IgG Fc Domain.

4. The bi-specific monovalent diabody of claim 3, wherein said sub-Domain (3B) of said second polypeptide chain comprises a sequence different from that of said sub-Domain (3B) of said third polypeptide chain.

5. The bi-specific monovalent diabody of claim 4, wherein said sub-Domain (3B) of said second polypeptide chain has the amino acid sequence of SEQ ID NO:40, and said sub-Domain (3B) of said third polypeptide chain has the amino acid sequence of SEQ ID NO:41.

6. The bi-specific monovalent diabody of claim 4, wherein said sub-Domain (3B) of said second polypeptide chain has the amino acid sequence of SEQ ID NO:41, and said sub-Domain (3B) of said third polypeptide chain has the amino acid sequence of SEQ ID NO:40.

7. The bi-specific monovalent diabody of claim 3, wherein said Domain 3 of said second polypeptide chain and/or said Domain 3 of said third polypeptide chain comprises a variant CH2-CH3 sequence that exhibits altered binding to an Fcγ receptor.

8. The bi-specific monovalent diabody of claim 1, wherein said Domain 2 of said first polypeptide chain comprises said E-coil (SEQ ID NO:3), and said Domain 2 of said second polypeptide chain comprises said K-coil (SEQ ID NO:4).

9. The bi-specific monovalent diabody of claim 1, wherein said Domain 2 of said first polypeptide chain comprises said K-coil (SEQ ID NO:4), and said Domain 2 of said second polypeptide chain comprises said E-coil (SEQ ID NO:3).

10. The bi-specific monovalent diabody of claim 1, wherein (1) said first polypeptide chain has the amino acid sequence of SEQ ID NO:28, and said second polypeptide chain has the amino acid sequence of SEQ ID NO:30; or (2) said first polypeptide chain has the amino acid sequence of SEQ ID NO:35, and said second polypeptide chain has the amino acid sequence of SEQ ID NO:30.

11. A pharmaceutical composition comprising the bi-specific monovalent diabody of claim 1; and a physiologically acceptable carrier.

12. A method for the treatment of a cancer characterized by the expression of gpA33, wherein said method comprises administering a therapeutically effective amount of the pharmaceutical composition of claim 11 to a subject in need of such treatment.

13. The method of claim 12, wherein said cancer is colorectal cancer, colon cancer, gastric cancer or pancreatic cancer.

14. A pharmaceutical composition comprising the bi-specific monovalent diabody of claim 3; and a physiologically acceptable carrier.

15. A method for the treatment of a cancer characterized by the expression of gpA33, wherein said method comprises administering a therapeutically effective amount of the pharmaceutical composition of claim 14 to a subject in need of such treatment.

16. The method of claim 15, wherein said cancer is colorectal cancer, colon cancer, gastric cancer or pancreatic cancer.

17. The bi-specific monovalent diabody of claim 3, wherein said bi-specific monovalent diabody is capable of specific binding to an epitope of CD3 and to an epitope of gpA33, and possesses an IgG Fc Domain, wherein said bi-specific monovalent diabody comprises:

(1) a first polypeptide chain having the amino acid sequence of SEQ ID NO:44, a second polypeptide chain having the amino acid sequence of SEQ ID NO:42, and a third polypeptide chain having the amino acid sequence of SEQ ID NO:46; or (2) a first polypeptide chain having the amino acid sequence of SEQ ID NO:28, a second polypeptide chain having the amino acid sequence of SEQ ID NO:48, and a third polypeptide chain having the amino acid sequence of SEQ ID NO:46;

wherein said first and said second polypeptide chains are covalently bonded to one another by a first disulfide bond and said second and third polypeptide chains are covalently bonded to one another by a second disulfide bond.

18. A pharmaceutical composition comprising the bi-specific monovalent diabody of claim 17, and a physiologically acceptable carrier.

19. A method for the treatment of a cancer characterized by the expression of gpA33, wherein said method comprises administering a therapeutically effective amount of the pharmaceutical composition of claim 18 to a subject in need of such treatment.

20. The method of claim 19, wherein said cancer is colorectal cancer, colon cancer, gastric cancer or pancreatic cancer.

* * * * *

```
                         SEQUENCE LISTING

<160> NUMBER OF SEQ ID NOS: 57

<210> SEQ ID NO 1
<211> LENGTH: 8
<212> TYPE: PRT
<213> ORGANISM: Artificial Sequence
<220> FEATURE:
<223> OTHER INFORMATION: Linker 1 Polypeptide

<400> SEQUENCE: 1

Gly Gly Gly Ser Gly Gly Gly Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Linker 2 Polypeptide

<400> SEQUENCE: 2

Gly Gly Cys Gly Gly Gly
1               5

<210> SEQ ID NO 3
<211> LENGTH: 28
<212> TYPE: PRT
<213> ORGANISM: Artificial Sequence
<220> FEATURE:
<223> OTHER INFORMATION: E-Coil Domain

<400> SEQUENCE: 3

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 4
<211> LENGTH: 28
<212> TYPE: PRT
<213> ORGANISM: Artificial Sequence
<220> FEATURE:
<223> OTHER INFORMATION: K-Coil Domain

<400> SEQUENCE: 4

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 5
<211> LENGTH: 110
<212> TYPE: PRT
<213> ORGANISM: Mus musculus
<220> FEATURE:
<221> NAME/KEY: MISC_FEATURE
<222> LOCATION: (1)..(110)
<223> OTHER INFORMATION: Light Chain Variable Domain of Murine Anti-CD3
      Antibody
```

-continued

<400> SEQUENCE: 5

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 6
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDR1 of Light Chain Variable Domain of Murine
      Anti-CD3 Antibody

<400> SEQUENCE: 6

Arg Ser Ser Thr Gly Ala Val Thr Thr Ser Asn Tyr Ala Asn
1               5                   10

<210> SEQ ID NO 7
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDR2 of Light Chain Variable Domain of Murine
      Anti-CD3 Antibody

<400> SEQUENCE: 7

Gly Thr Asn Lys Arg Ala Pro
1               5

<210> SEQ ID NO 8
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDR3 of Light Chain Variable Domain of Murine
      Anti-CD3 Antibody

<400> SEQUENCE: 8

Ala Leu Trp Tyr Ser Asn Leu Trp Val
1               5

<210> SEQ ID NO 9
<211> LENGTH: 125
<212> TYPE: PRT
<213> ORGANISM: Mus musculus
<220> FEATURE:
<221> NAME/KEY: MISC_FEATURE
<222> LOCATION: (1)..(125)

<223> OTHER INFORMATION: Heavy Chain Variable Domain of Murine Anti-CD3
    Antibody

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 10
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDR1 of Heavy Chain Variable Domain of Murine
    Anti-CD3 Antibody

<400> SEQUENCE: 10

Thr Tyr Ala Met Asn
1               5

<210> SEQ ID NO 11
<211> LENGTH: 19
<212> TYPE: PRT
<213> ORGANISM: Mus musculus
<220> FEATURE:
<221> NAME/KEY: MISC_FEATURE
<222> LOCATION: (1)..(19)
<223> OTHER INFORMATION: CDR2 of Heavy Chain Variable Domain of Murine
    Anti-CD3 Antibody

<400> SEQUENCE: 11

Arg Ile Arg Ser Lys Tyr Asn Asn Tyr Ala Thr Tyr Tyr Ala Asp Ser
1               5                   10                  15

Val Lys Asp

<210> SEQ ID NO 12
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: CDR3 of Heavy Chain Variable Domain of Murine
    Anti-CD3 Antibody

<400> SEQUENCE: 12

His Gly Asn Phe Gly Asn Ser Tyr Val Ser Trp Phe Ala Tyr
1               5                   10

```
<210> SEQ ID NO 13
<211> LENGTH: 106
<212> TYPE: PRT
<213> ORGANISM: Mus musculus
<220> FEATURE:
<221> NAME/KEY: misc_feature
<223> OTHER INFORMATION: Light Chain Variable Domain of Murine
      Anti-gpA33 Antibody

<400> SEQUENCE: 13

Gln Ile Val Leu Thr Gln Ser Pro Ala Ile Met Ser Ala Ser Pro Gly
1               5                   10                  15

Glu Arg Val Thr Met Thr Cys Ser Ala Arg Ser Ser Ile Ser Phe Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Ser Gly Thr Lys Leu Glu Leu Lys
            100                 105

<210> SEQ ID NO 14
<211> LENGTH: 10
<212> TYPE: PRT
<213> ORGANISM: Mus musculus
<220> FEATURE:
<221> NAME/KEY: misc_feature
<222> LOCATION: (1)..(10)
<223> OTHER INFORMATION: CDR1 of Light Chain Variable Domain of Murine
      Anti-gpA33 Antibody

<400> SEQUENCE: 14

Ser Ala Arg Ser Ser Ile Ser Phe Met Tyr
1               5                   10

<210> SEQ ID NO 15
<211> LENGTH: 7
<212> TYPE: PRT
<213> ORGANISM: Mus musculus
<220> FEATURE:
<221> NAME/KEY: misc_feature
<222> LOCATION: (1)..(7)
<223> OTHER INFORMATION: CDR2 of Light Chain Variable Domain of Murine
      Anti-gpA33 Antibody

<400> SEQUENCE: 15

Asp Thr Ser Asn Leu Ala Ser
1               5

<210> SEQ ID NO 16
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDR3 of Light Chain Variable Domain of Murine
      Anti-gpA33 Antibody

<400> SEQUENCE: 16

Gln Gln Trp Ser Ser Tyr Pro Leu Thr
```

```
<210> SEQ ID NO 17
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: Heavy Chain Variable Domain of Murine
      Anti-gpA33 Antibody

<400> SEQUENCE: 17

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Ser Gly Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Glu Thr Asn Tyr Asn Gly Lys Phe
    50                  55                  60

Lys Asp Lys Ala Thr Leu Thr Ala Asp Lys Ser Ser Thr Thr Ala Tyr
65                  70                  75                  80

Met Glu Leu Ser Ser Leu Thr Ser Val Asp Ser Ala Val Tyr Phe Cys
                85                  90                  95

Ala Arg Ile Tyr Gly Asn Asn Val Tyr Phe Asp Val Trp Gly Ala Gly
            100                 105                 110

Thr Thr Val Thr Val Ser Ser
        115

<210> SEQ ID NO 18
<211> LENGTH: 5
<212> TYPE: PRT
<213> ORGANISM: Mus musculus
<220> FEATURE:
<221> NAME/KEY: misc_feature
<223> OTHER INFORMATION: CDR1 of Heavy Chain Variable Domain of Murine
      Anti-gpA33 Antibody

<400> SEQUENCE: 18

Gly Ser Trp Met Asn
1               5

<210> SEQ ID NO 19
<211> LENGTH: 17
<212> TYPE: PRT
<213> ORGANISM: Mus musculus
<220> FEATURE:
<221> NAME/KEY: misc_feature
<223> OTHER INFORMATION: CDR2 of Heavy Chain Variable Domain of Murine
      Anti-gpA33 Antibody

<400> SEQUENCE: 19

Arg Ile Tyr Pro Gly Asp Gly Glu Thr Asn Tyr Asn Gly Lys Phe Lys
1               5                   10                  15

Asp

<210> SEQ ID NO 20
<211> LENGTH: 10
<212> TYPE: PRT
<213> ORGANISM: Mus musculus
<220> FEATURE:
<221> NAME/KEY: misc_feature
<223> OTHER INFORMATION: CDR3 of Heavy Chain Variable Domain of Murine
```

Anti-gpA33 Antibody

<400> SEQUENCE: 20

Ile Tyr Gly Asn Asn Val Tyr Phe Asp Val
1               5                   10

<210> SEQ ID NO 21
<211> LENGTH: 271
<212> TYPE: PRT
<213> ORGANISM: Artificial Sequence
<220> FEATURE:
<223> OTHER INFORMATION: First Polypeptide Chain of DART-1

<400> SEQUENCE: 21

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Gln Gln Ser Gly Pro Glu
        115                 120                 125

Leu Val Lys Pro Gly Ala Ser Val Lys Ile Ser Cys Lys Ala Ser Gly
    130                 135                 140

Tyr Thr Phe Ser Gly Ser Trp Met Asn Trp Val Lys Gln Arg Pro Gly
145                 150                 155                 160

Gln Gly Leu Glu Trp Ile Gly Arg Ile Tyr Pro Gly Asp Gly Glu Thr
                165                 170                 175

Asn Tyr Asn Gly Lys Phe Lys Asp Lys Ala Thr Leu Thr Ala Asp Lys
            180                 185                 190

Ser Ser Thr Thr Ala Tyr Met Glu Leu Ser Ser Leu Thr Ser Val Asp
        195                 200                 205

Ser Ala Val Tyr Phe Cys Ala Arg Ile Tyr Gly Asn Asn Val Tyr Phe
    210                 215                 220

Asp Val Trp Gly Ala Gly Thr Thr Val Thr Val Ser Ser Gly Gly Cys
225                 230                 235                 240

Gly Gly Gly Glu Val Ala Ala Leu Glu Lys Glu Val Ala Ala Leu Glu
                245                 250                 255

Lys Glu Val Ala Ala Leu Glu Lys Glu Val Ala Ala Leu Glu Lys
            260                 265                 270

<210> SEQ ID NO 22
<211> LENGTH: 813
<212> TYPE: DNA
<213> ORGANISM: Artificial Sequence
<220> FEATURE:
<223> OTHER INFORMATION: Nucleic Acid Molecule Encoding First
      Polypeptide Chain of DART-1

<400> SEQUENCE: 22

```
caggctgtgg tgactcagga gccttcactg accgtgtccc caggcggaac tgtgaccctg    60
acatgcagat ccagcacagg cgcagtgacc acatctaact acgccaattg ggtgcagcag   120
aagccaggac aggcaccaag gggcctgatc ggggtacaa acaaaagggc tccctggacc    180
cctgcacggt tttctggaag tctgctgggc ggaaaggccg ctctgactat accggggca    240
caggccgagg acgaagccga ttactattgt gctctgtggt atagcaatct gtgggtgttc   300
gggggtggca aaaactgac tgtgctggga gtggtggat ccggcggagg tggacaggtc    360
cagctgcagc agtctggacc tgagctggtg aagcctgggg cctcagtgaa gatttcctgc   420
aaagcttcag gctacacatt cagtggctct tggatgaact gggtgaagca gaggcctgga   480
cagggtcttg agtggattgg acggatctac cctggagatg gagaaactaa ctacaatggg   540
aagtttaagg acaaggccac actgactgca gacaaatcat ccaccacagc ctacatggag   600
ctcagcagcc tgacctctgt ggactctgcg gtctatttct gtgcaagaat ctatggtaat   660
aacgtttact tcgatgtctg gggcgcaggg accacggtca ccgtgtcttc cggaggatgt   720
ggcggtggag aagtggccgc actggagaaa gaggttgctg ctttggagaa ggaggtcgct   780
gcacttgaaa aggaggtcgc agccctggag aaa                                813
```

<210> SEQ ID NO 23
<211> LENGTH: 274
<212> TYPE: PRT
<213> ORGANISM: Artificial Sequence
<220> FEATURE:
<223> OTHER INFORMATION: Second Polypeptide Chain of DART-1

<400> SEQUENCE: 23

```
Gln Ile Val Leu Thr Gln Ser Pro Ala Ile Met Ser Ala Ser Pro Gly
1               5                   10                  15

Glu Arg Val Thr Met Thr Cys Ser Ala Arg Ser Ser Ile Ser Phe Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Ser Gly Thr Lys Leu Glu Leu Lys Arg Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
    130                 135                 140

Asn Thr Tyr Ala Met Asn Trp Val Arg Gln Ala Pro Gly Lys Gly Leu
145                 150                 155                 160

Glu Trp Val Ala Arg Ile Arg Ser Lys Tyr Asn Asn Tyr Ala Thr Tyr
                165                 170                 175

Tyr Ala Asp Ser Val Lys Asp Arg Phe Thr Ile Ser Arg Asp Asp Ser
            180                 185                 190

Lys Asn Ser Leu Tyr Leu Gln Met Asn Ser Leu Lys Thr Glu Asp Thr
        195                 200                 205

Ala Val Tyr Tyr Cys Val Arg His Gly Asn Phe Gly Asn Ser Tyr Val
    210                 215                 220
```

Ser Trp Phe Ala Tyr Trp Gly Gln Gly Thr Leu Val Thr Val Ser Ser
225                 230                 235                 240

Gly Gly Cys Gly Gly Gly Lys Val Ala Ala Leu Lys Glu Lys Val Ala
                245                 250                 255

Ala Leu Lys Glu Lys Val Ala Ala Leu Lys Glu Lys Val Ala Ala Leu
            260                 265                 270

Lys Glu

<210> SEQ ID NO 24
<211> LENGTH: 822
<212> TYPE: DNA
<213> ORGANISM: Artificial Sequence
<220> FEATURE:
<223> OTHER INFORMATION: Nucleic Acid Molecule Encoding Second
      Polypeptide Chain of DART-1

<400> SEQUENCE: 24
caaattgttc tcacccagtc tccagcaatc atgtctgcat ctccagggga gagggtcacc      60
atgacctgca gtgccaggtc aagtataagt ttcatgtact ggtaccagca gaagccagga    120
tcctccccca gactcctgat ttatgacaca tccaacctgg cttctggagt ccctgttcgc    180
ttcagtggca gtgggtctgg gacctcttat tctctcacaa tcagccgaat ggaggctgaa    240
gatgctgcca cttattactg ccagcagtgg agtagttacc cactcacgtt cggttctggg    300
accaagctgg agctgaaacg gggtggagga tccggcggag gcggagaggt gcagctggtg    360
gagtctgggg gaggcttggt ccagcctgga gggtccctga ctctcctg tgcagcctct     420 ggattcacct tcaacacata cgctatgaat tgggtccgcc aggctccagg aaggggctg    480 gagtgggttg caaggatcag gtccaagtac aacaattatg caacctacta tgccgactct    540
gtgaaggata gattcaccat ctcaagagat gattcaaaga actcactgta tctgcaaatg    600
aacagcctga aaaccgagga cacggccgtg tattactgtg tgagacacgg taacttcggc    660
aattcttacg tgtcttggtt tgcttattgg ggacagggga cactggtgac tgtgtcttcc    720
ggaggatgtg gcggtggaaa agtggccgca ctgaaggaga agttgctgc tttgaaagag    780 aaggtcgccg cacttaagga aaaggtcgca gccctgaaag ag                       822

<210> SEQ ID NO 25
<211> LENGTH: 125
<212> TYPE: PRT
<213> ORGANISM: Mus musculus
<220> FEATURE:
<221> NAME/KEY: MISC_FEATURE
<222> LOCATION: (1)..(125)
<223> OTHER INFORMATION: Heavy Chain Variable Domain of Anti-CD3
      Antibody

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

```
Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 26
<211> LENGTH: 106
<212> TYPE: PRT
<213> ORGANISM: Artificial Sequence
<220> FEATURE:
<223> OTHER INFORMATION: Light Chain Variable Domain of Humanized
      Anti-gpA33 Antibody

<400> SEQUENCE: 26

Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Glu Ala Glu
65                  70                  75                  80

Asp Ala Ala Thr Tyr Tyr Cys Gln Gln Trp Ser Ser Tyr Pro Leu Thr
                85                  90                  95

Phe Gly Gln Gly Thr Lys Leu Glu Ile Lys
            100                 105

<210> SEQ ID NO 27
<211> LENGTH: 119
<212> TYPE: PRT
<213> ORGANISM: Artificial Sequence
<220> FEATURE:
<223> OTHER INFORMATION: Heavy Chain Variable Domain of Humanized
      Anti-gpA33 Antibody

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Glu Thr Asn Tyr Asn Gly Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Gly Asn Asn Val Tyr Phe Asp Val Trp Gly Gln Gly
            100                 105                 110

Thr Thr Val Thr Val Ser Ser
            115

<210> SEQ ID NO 28
<211> LENGTH: 271
```

<212> TYPE: PRT
<213> ORGANISM: Artificial Sequence
<220> FEATURE:
<223> OTHER INFORMATION: First Polypeptide Chain of DART-2

<400> SEQUENCE: 28

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Ala Glu
        115                 120                 125

Val Lys Lys Pro Gly Ala Ser Val Lys Val Ser Cys Lys Ala Ser Gly
130                 135                 140

Tyr Thr Phe Thr Gly Ser Trp Met Asn Trp Val Arg Gln Ala Pro Gly
145                 150                 155                 160

Gln Gly Leu Glu Trp Ile Gly Arg Ile Tyr Pro Gly Asp Gly Glu Thr
                165                 170                 175

Asn Tyr Asn Gly Lys Phe Lys Asp Arg Val Thr Ile Thr Ala Asp Lys
            180                 185                 190

Ser Thr Ser Thr Ala Tyr Met Glu Leu Ser Ser Leu Arg Ser Glu Asp
        195                 200                 205

Thr Ala Val Tyr Tyr Cys Ala Arg Ile Tyr Gly Asn Asn Val Tyr Phe
    210                 215                 220

Asp Val Trp Gly Gln Gly Thr Thr Val Thr Val Ser Ser Gly Gly Cys
225                 230                 235                 240

Gly Gly Gly Glu Val Ala Ala Leu Glu Lys Glu Val Ala Ala Leu Glu
                245                 250                 255

Lys Glu Val Ala Ala Leu Glu Lys Glu Val Ala Ala Leu Glu Lys
            260                 265                 270
```

<210> SEQ ID NO 29
<211> LENGTH: 813
<212> TYPE: DNA
<213> ORGANISM: Artificial Sequence
<220> FEATURE:
<223> OTHER INFORMATION: Nucleic Acid Molecule Encoding First
      Polypeptide Chain of DART-2

<400> SEQUENCE: 29

```
caggctgtgg tgactcagga gccttcactg accgtgtccc caggcggaac tgtgaccctg    60
acatgcagat ccagcacagg cgcagtgacc acatctaact acgccaattg ggtgcagcag   120
aagccaggac aggcaccaag gggcctgatc gggggtacaa acaaaagggc tccctggacc   180
cctgcacggt tttctggaag tctgctgggc ggaaaggccg ctctgactat taccggggca   240
caggccgagg acgaagccga ttactattgt gctctgtggt atagcaatct gtgggtgttc   300
```

```
gggggtggca caaaactgac tgtgctggga ggtggtggat ccggcggagg tggacaggtc    360
cagctggtcc agagcgggc cgaagtcaaa aacccggag caagcgtgaa ggtctcctgc      420
aaagcatcag gctatacatt acaggcagc tggatgaact gggtgaggca ggctccagga     480
cagggactgg agtggatcgg gcgcatctac cctggagacg gcgaaactaa ctataatgga    540
aagttcaaag accgagtgac catcacagcc gataagtcta ctagtaccgc ctacatggag    600
ctgagctccc tgcggtctga agataccgcc gtctactatt gcgctagaat ttacggaaac    660
aatgtctatt ttgacgtgtg ggggcaggga acaactgtga ctgtctcctc cggaggatgt    720
ggcggtggag aagtggccgc actggagaaa gaggttgctg ctttggagaa ggaggtcgct    780
gcacttgaaa aggaggtcgc agccctggag aaa                                 813
```

<210> SEQ ID NO 30
<211> LENGTH: 273
<212> TYPE: PRT
<213> ORGANISM: Artificial Sequence
<220> FEATURE:
<223> OTHER INFORMATION: Second Polypeptide Chain of DART-2

<400> SEQUENCE: 30

```
Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Glu Ala Glu
65                  70                  75                  80

Asp Ala Ala Thr Tyr Tyr Cys Gln Gln Trp Ser Ser Tyr Pro Leu Thr
                85                  90                  95

Phe Gly Gln Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
    130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Asp Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
    210                 215                 220

Trp Phe Ala Tyr Trp Gly Gln Gly Thr Leu Val Thr Val Ser Ser Gly
225                 230                 235                 240

Gly Cys Gly Gly Gly Lys Val Ala Ala Leu Lys Glu Lys Val Ala Ala
                245                 250                 255

Leu Lys Glu Lys Val Ala Ala Leu Lys Glu Lys Val Ala Ala Leu Lys
            260                 265                 270
```

Glu

<210> SEQ ID NO 31
<211> LENGTH: 819
<212> TYPE: DNA
<213> ORGANISM: Artificial Sequence
<220> FEATURE:
<223> OTHER INFORMATION: Nucleic Acid Molecule Encoding Second
      Polypeptide Chain of DART-2

<400> SEQUENCE: 31

```
gacattcagc tgactcagtc cccctctttt ctgtccgcat ccgtcggaga tcgagtgact    60
attacttgct ctgctaggtc ctcaatcagc ttcatgtact ggtatcagca gaagcccggc   120
aaagcaccta agctgctgat ctacgacaca agcaacctgg cctccggggt gccatctcgg   180
ttctctggca gtgggtcagg aactgagttt accctgacaa ttagctccct ggaggctgaa   240
gatgccgcta cctactattg ccagcagtgg agcagctatc ctctgacctt cggacagggg   300
actaaactgg aaatcaaggg tggaggatcc ggcggcggag gcgaggtgca gctggtggag   360
tctgggggag gcttggtcca gcctggaggg tccctgagac tctcctgtgc agcctctgga   420
ttcaccttca gcacatacgc tatgaattgg gtccgccagg ctccagggaa ggggctggag   480
tgggttggaa ggatcaggtc caagtacaac aattatgcaa cctactatgc cgactctgtg   540
aaggatagat tcaccatctc aagagatgat tcaaagaact cactgtatct gcaaatgaac   600
agcctgaaaa ccgaggacac ggccgtgtat tactgtgtga cacggtaa cttcggcaat    660
tcttacgtgt cttggtttgc ttattgggga caggggacac tggtgactgt gtcttccgga   720
ggatgtggcg gtggaaaagt ggccgcactg aaggagaaag ttgctgcttt gaaagagaag   780
gtcgccgcac ttaaggaaaa ggtcgcagcc ctgaaagag                          819
```

<210> SEQ ID NO 32
<211> LENGTH: 4
<212> TYPE: PRT
<213> ORGANISM: Artificial Sequence
<220> FEATURE:
<223> OTHER INFORMATION: Linker 3 Polypeptide

<400> SEQUENCE: 32

Gly Gly Gly Ser
1

<210> SEQ ID NO 33
<211> LENGTH: 5
<212> TYPE: PRT
<213> ORGANISM: Artificial Sequence
<220> FEATURE:
<223> OTHER INFORMATION: Linker 3 Polypeptide

<400> SEQUENCE: 33

Gly Gly Gly Asn Ser
1               5

<210> SEQ ID NO 34
<211> LENGTH: 46
<212> TYPE: PRT
<213> ORGANISM: Artificial Sequence
<220> FEATURE:
<223> OTHER INFORMATION: Albumin Binding Domain

<400> SEQUENCE: 34

Leu Ala Gln Ala Lys Glu Ala Ala Ile Arg Glu Leu Asp Lys Tyr Gly
1               5                   10                  15

Val Ser Asp Tyr Tyr Lys Asn Leu Ile Asp Asn Ala Lys Ser Ala Glu
             20                  25                  30

Gly Val Lys Ala Leu Ile Asp Glu Ile Leu Ala Ala Leu Pro
         35                  40                  45

<210> SEQ ID NO 35
<211> LENGTH: 321
<212> TYPE: PRT
<213> ORGANISM: Artificial Sequence
<220> FEATURE:
<223> OTHER INFORMATION: First Polypeptide Chain of DART-2 w/ABD

<400> SEQUENCE: 35

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
             20                  25                  30

Asn Tyr Ala Asn Trp Val Gln Gln Lys Pro Gly Gln Ala Pro Arg Gly
         35                  40                  45

Leu Ile Gly Gly Thr Asn Lys Arg Ala Pro Trp Thr Pro Ala Arg Phe
     50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Ala Glu
        115                 120                 125

Val Lys Lys Pro Gly Ala Ser Val Lys Val Ser Cys Lys Ala Ser Gly
130                 135                 140

Tyr Thr Phe Thr Gly Ser Trp Met Asn Trp Val Arg Gln Ala Pro Gly
145                 150                 155                 160

Gln Gly Leu Glu Trp Ile Gly Arg Ile Tyr Pro Gly Asp Gly Glu Thr
                165                 170                 175

Asn Tyr Asn Gly Lys Phe Lys Asp Arg Val Thr Ile Thr Ala Asp Lys
            180                 185                 190

Ser Thr Ser Thr Ala Tyr Met Glu Leu Ser Ser Leu Arg Ser Glu Asp
        195                 200                 205

Thr Ala Val Tyr Tyr Cys Ala Arg Ile Tyr Gly Asn Asn Val Tyr Phe
210                 215                 220

Asp Val Trp Gly Gln Gly Thr Thr Val Thr Val Ser Ser Gly Gly Cys
225                 230                 235                 240

Gly Gly Gly Glu Val Ala Ala Leu Glu Lys Glu Val Ala Ala Leu Glu
                245                 250                 255

Lys Glu Val Ala Ala Leu Glu Lys Glu Val Ala Ala Leu Glu Lys Gly
            260                 265                 270

Gly Gly Ser Leu Ala Gln Ala Lys Glu Ala Ala Ile Arg Glu Leu Asp
        275                 280                 285

Lys Tyr Gly Val Ser Asp Tyr Tyr Lys Asn Leu Ile Asp Asn Ala Lys
290                 295                 300

Ser Ala Glu Gly Val Lys Ala Leu Ile Asp Glu Ile Leu Ala Ala Leu
305                 310                 315                 320

Pro

<210> SEQ ID NO 36
<211> LENGTH: 963
<212> TYPE: DNA
<213> ORGANISM: Artificial Sequence
<220> FEATURE:
<223> OTHER INFORMATION: Nucleic Acid Molecule Encoding First
      Polypeptide Chain of DART-2 w/ABD

<400> SEQUENCE: 36

```
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc ggggtacaa acaaaagggc tccctggacc      180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca aaaactgac tgtgctggga ggggtggat ccggcggagg tggacaggtc      360
cagctggtcc agagcggggc cgaagtcaaa aacccggag caagcgtgaa ggtctcctgc      420 aaaagcatcag gctatacatt tacaggcagc tggatgaact gggtgaggca ggctccagga     480
cagggactgg agtggatcgg cgcatctac cctggagacg gcgaaactaa ctataatgga      540
aagttcaaag accgagtgac catcacagcc gataagtcta ctagtaccgc ctacatggag     600
ctgagctccc tgcggtctga agataccgcc gtctactatt gcgctagaat ttacggaaac     660
aatgtctatt ttgacgtgtg ggggcaggga acaactgtga ctgtctcctc cggaggatgt     720
ggcggtggag aagtggccgc actggagaaa gaggttgctg ctttggagaa ggaggtcgct     780
gcacttgaaa aggaggtcgc agccctggag aaaggcggcg gtctctggc ccaggcaaaa     840 gaggcagcca tccgcgaact ggataaatat ggcgtgagcg attattataa gaacctgatt     900
gacaacgcaa atccgcgga aggcgtgaaa gcactgattg atgaaattct ggccgccctg     960
cct                                                                   963
```

<210> SEQ ID NO 37
<211> LENGTH: 5
<212> TYPE: PRT
<213> ORGANISM: Artificial Sequence
<220> FEATURE:
<223> OTHER INFORMATION: Linker 4 Polypeptide

<400> SEQUENCE: 37

Ala Pro Ser Ser Ser
1               5

<210> SEQ ID NO 38
<211> LENGTH: 8
<212> TYPE: PRT
<213> ORGANISM: Artificial Sequence
<220> FEATURE:
<223> OTHER INFORMATION: Linker 4 Polypeptide

<400> SEQUENCE: 38

Ala Pro Ser Ser Ser Pro Met Glu
1               5

<210> SEQ ID NO 39
<211> LENGTH: 10
<212> TYPE: PRT
<213> ORGANISM: Artificial Sequence
<220> FEATURE:
<223> OTHER INFORMATION: Peptide 1

<400> SEQUENCE: 39

Asp Lys Thr His Thr Cys Pro Pro Cys Pro
1               5                   10

<210> SEQ ID NO 40
<211> LENGTH: 217
<212> TYPE: PRT
<213> ORGANISM: Artificial Sequence
<220> FEATURE:
<223> OTHER INFORMATION: CH2 and CH3 Domains of Modified Fc Domain of
      First DART Polypeptide Chain

<400> SEQUENCE: 40

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 41
<211> LENGTH: 217
<212> TYPE: PRT
<213> ORGANISM: Artificial Sequence
<220> FEATURE:
<223> OTHER INFORMATION: CH2 and CH3 Domains of Modified Fc Domain of
      Third DART Polypeptide Chain

<400> SEQUENCE: 41

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu

```
                    50                  55                  60
Gln Tyr Asn Ser Thr Tyr Arg Val Val Ser Val Leu Thr Val His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Lys
    210                 215
```

<210> SEQ ID NO 42
<211> LENGTH: 503
<212> TYPE: PRT
<213> ORGANISM: Artificial Sequence
<220> FEATURE:
<223> OTHER INFORMATION: First Polypeptide Chain of DART-2 w/Fc Version
      1 Construct

<400> SEQUENCE: 42

```
Asp Ile Gln Leu Thr Gln Ser Pro Ser Phe Leu Ser Ala Ser Val Gly
  1               5                  10                  15

Asp Arg Val Thr Ile Thr Cys Ser Ala Arg Ser Ser Ile Ser Phe Met
             20                  25                  30

Tyr Trp Tyr Gln Gln Lys Pro Gly Lys Ala Pro Lys Leu Leu Ile Tyr
         35                  40                  45

Asp Thr Ser Asn Leu Ala Ser Gly Val Pro Ser Arg Phe Ser Gly Ser
 50                  55                  60

Gly Ser Gly Thr Glu Phe Thr Leu Thr Ile Ser Ser Leu Glu Ala Glu
 65                  70                  75                  80

Asp Ala Ala Thr Tyr Tyr Cys Gln Gln Trp Ser Ser Tyr Pro Leu Thr
                 85                  90                  95

Phe Gly Gln Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Asp Arg Phe Thr Ile Ser Arg Asp Asp Ser Lys
            180                 185                 190
```

```
Asn Ser Leu Tyr Leu Gln Met Asn Ser Leu Lys Thr Glu Asp Thr Ala
            195                 200                 205
Val Tyr Tyr Cys Val Arg His Gly Asn Phe Gly Asn Ser Tyr Val Ser
210                 215                 220
Trp Phe Ala Tyr Trp Gly Gln Gly Thr Leu Val Thr Val Ser Ser Gly
225                 230                 235                 240
Gly Cys Gly Gly Gly Glu Val Ala Ala Leu Glu Lys Glu Val Ala Ala
                245                 250                 255
Leu Glu Lys Glu Val Ala Ala Leu Glu Lys Glu Val Ala Ala Leu Glu
            260                 265                 270
Lys Gly Gly Asp Lys Thr His Thr Cys Pro Pro Cys Pro Ala Pro
            275                 280                 285
Glu Ala Ala Gly Gly Pro Ser Val Phe Leu Phe Pro Pro Lys Pro Lys
290                 295                 300
Asp Thr Leu Met Ile Ser Arg Thr Pro Glu Val Thr Cys Val Val Val
305                 310                 315                 320
Asp Val Ser His Glu Asp Pro Glu Val Lys Phe Asn Trp Tyr Val Asp
                325                 330                 335
Gly Val Glu Val His Asn Ala Lys Thr Lys Pro Arg Glu Glu Gln Tyr
            340                 345                 350
Asn Ser Thr Tyr Arg Val Val Ser Val Leu Thr Val Leu His Gln Asp
        355                 360                 365
Trp Leu Asn Gly Lys Glu Tyr Lys Cys Lys Val Ser Asn Lys Ala Leu
    370                 375                 380
Pro Ala Pro Ile Glu Lys Thr Ile Ser Lys Ala Lys Gly Gln Pro Arg
385                 390                 395                 400
Glu Pro Gln Val Tyr Thr Leu Pro Pro Ser Arg Glu Glu Met Thr Lys
                405                 410                 415
Asn Gln Val Ser Leu Trp Cys Leu Val Lys Gly Phe Tyr Pro Ser Asp
            420                 425                 430
Ile Ala Val Glu Trp Glu Ser Asn Gly Gln Pro Glu Asn Asn Tyr Lys
        435                 440                 445
Thr Thr Pro Pro Val Leu Asp Ser Asp Gly Ser Phe Phe Leu Tyr Ser
    450                 455                 460
Lys Leu Thr Val Asp Lys Ser Arg Trp Gln Gln Gly Asn Val Phe Ser
465                 470                 475                 480
Cys Ser Val Met His Glu Ala Leu His Asn His Tyr Thr Gln Lys Ser
                485                 490                 495
Leu Ser Leu Ser Pro Gly Lys
            500

<210> SEQ ID NO 43
<211> LENGTH: 1509
<212> TYPE: DNA
<213> ORGANISM: Artificial Sequence
<220> FEATURE:
<223> OTHER INFORMATION: Nucleic Acid Molecule Encoding First
      Polypeptide Chain of DART-2 w/Fc Version 1 Construct

<400> SEQUENCE: 43
gacattcagc tgactcagtc ccctctcttt ctgtccgcat ccgtcggaga tcgagtgact     60
attacttgct ctgctaggtc ctcaatcagc ttcatgtact ggtatcagca gaagcccggc    120
aaagcaccta agctgctgat ctacgacaca agcaacctgg cctccggggt gccatctcgg    180
ttctctggca gtgggtcagg aactgagttt accctgacaa ttgctcccct ggaggctgaa    240
```

```
gatgccgcta cctactattg ccagcagtgg agcagctatc ctctgacctt cggacagggg    300
actaaactgg aaatcaaggg tggaggatcc ggcggcggag gcgaggtgca gctggtggag    360
tctgggggag gcttggtcca gcctggaggg tccctgagac tctcctgtgc agcctctgga    420
ttcaccttca gcacatacgc tatgaattgg gtccgccagg ctccagggaa ggggctggag    480
tgggttggaa ggatcaggtc caagtacaac aattatgcaa cctactatgc cgactctgtg    540
aaggatagat tcaccatctc aagagatgat tcaaagaact cactgtatct gcaaatgaac    600
agcctgaaaa ccgaggacac ggccgtgtat tactgtgtga cacggtaa cttcggcaat    660 tcttacgtgt cttggtttgc ttattgggga caggggacac tggtgactgt gtcttccgga    720
ggatgtggcg gtggagaagt ggccgcactg gagaaagagg ttgctgcttt ggagaaggag    780
gtcgctgcac ttgaaaagga ggtcgcagcc ctggagaaag cggcggggga caaaactcac    840
acatgcccac cgtgcccagc acctgaagcc gcgggggac cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg   1020
cataatgcca agacaaagcc gcgggaggag cagtacaaca gcacgtaccg tgtggtcagc   1080
gtcctcaccg tcctgcacca ggactggctg aatggcaagg agtacaagtg caaggtctcc   1140
aacaaagccc tcccagcccc catcgagaaa accatctcca aagccaaagg gcagccccga   1200
gaaccacagg tgtacaccct gcccccatcc cgggaggaga tgaccaagaa ccaggtcagc   1260
ctgtggtgcc tggtcaaagg cttctatccc agcgacatcg ccgtggagtg ggagagcaat   1320
gggcagccgg agaacaacta caagaccacg cctcccgtgc tggactccga cggctccttc   1380
ttcctctaca gcaagctcac cgtggacaag agcaggtggc agcaggggaa cgtcttctca   1440
tgctccgtga tgcatgaggc tctgcacaac cactacacgc agaagagcct ctccctgtct   1500
ccgggtaaa                                                            1509
```

<210> SEQ ID NO 44
<211> LENGTH: 271
<212> TYPE: PRT
<213> ORGANISM: Artificial Sequence
<220> FEATURE:
<223> OTHER INFORMATION: Second Polypeptide Chain of DART-2 w/Fc Version
      1 Construct

<400> SEQUENCE: 44

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Ala Glu
        115                 120                 125

```
Val Lys Lys Pro Gly Ala Ser Val Lys Val Ser Cys Lys Ala Ser Gly
    130                 135                 140
Tyr Thr Phe Thr Gly Ser Trp Met Asn Trp Val Arg Gln Ala Pro Gly
145                 150                 155                 160
Gln Gly Leu Glu Trp Ile Gly Arg Ile Tyr Pro Gly Asp Gly Glu Thr
                165                 170                 175
Asn Tyr Asn Gly Lys Phe Lys Asp Arg Val Thr Ile Thr Ala Asp Lys
                180                 185                 190
Ser Thr Ser Thr Ala Tyr Met Glu Leu Ser Ser Leu Arg Ser Glu Asp
            195                 200                 205
Thr Ala Val Tyr Tyr Cys Ala Arg Ile Tyr Gly Asn Asn Val Tyr Phe
    210                 215                 220
Asp Val Trp Gly Gln Gly Thr Thr Val Thr Val Ser Ser Gly Gly Cys
225                 230                 235                 240
Gly Gly Gly Lys Val Ala Ala Leu Lys Glu Lys Val Ala Ala Leu Lys
                245                 250                 255
Glu Lys Val Ala Ala Leu Lys Glu Lys Val Ala Ala Leu Lys Glu
            260                 265                 270
```

<210> SEQ ID NO 45
<211> LENGTH: 813
<212> TYPE: DNA
<213> ORGANISM: Artificial Sequence
<220> FEATURE:
<223> OTHER INFORMATION: Nucleic Acid Molecule Encoding Second
      Polypeptide Chain of DART-2 w/Fc Version 1 Construct

<400> SEQUENCE: 45

```
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc ggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca aaaactgac tgtgctggga ggggtggat ccggcggagg tggacaggtc     360
cagctggtcc agagcggggc cgaagtcaaa aacccggag caagcgtgaa ggtctcctgc     420
aaagcatcag gctatacatt tacaggcagc tggatgaact gggtgaggca ggctccagga     480
cagggactgg agtggatcgg cgcatctac cctggagacg gcgaaactaa ctataatgga     540
aagttcaaag accgagtgac catcacagcc gataagtcta ctagtaccgc ctacatggag     600
ctgagctccc tgcggtctga agataccgcc gtctactatt gcgctagaat ttacggaaac     660
aatgtctatt ttgacgtgtg gggcaggga acaactgtga ctgtctcctc cggaggatgt     720
ggcggtggaa agtggccgc actgaaggag aaagttgctg ctttgaaaga aaggtcgcc     780
gcacttaagg aaaaggtcgc agccctgaaa gag                                 813
```

<210> SEQ ID NO 46
<211> LENGTH: 227
<212> TYPE: PRT
<213> ORGANISM: Artificial Sequence
<220> FEATURE:
<223> OTHER INFORMATION: Third Polypeptide Chain of DART-2 w/Fc Version
      1 Construct

<400> SEQUENCE: 46

```
Asp Lys Thr His Thr Cys Pro Pro Cys Pro Ala Pro Glu Ala Ala Gly
1               5                   10                  15
```

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
210                 215                 220

Pro Gly Lys
225

<210> SEQ ID NO 47
<211> LENGTH: 681
<212> TYPE: DNA
<213> ORGANISM: Artificial Sequence
<220> FEATURE:
<223> OTHER INFORMATION: Nucleic acid Molecule Encoding Third
      Polypeptide Chain of DART-2 w/Fc Version 1 Construct

<400> SEQUENCE: 47
gacaaaactc acacatgccc accgtgccca gcacctgaag ccgcggggggg accgtcagtc    60 ttcctcttcc ccccaaaacc caaggacacc ctcatgatct cccggacccc tgaggtcaca   120
tgcgtggtgg tggacgtgag ccacgaagac cctgaggtca agttcaactg gtacgtggac   180
ggcgtggagg tgcataatgc caagacaaag ccgcgggagg agcagtacaa cagcacgtac   240
cgtgtggtca gcgtcctcac cgtcctgcac caggactggc tgaatggcaa ggagtacaag   300
tgcaaggtct ccaacaaagc cctcccagcc ccatcgaga aaaccatctc aaagccaaa    360 gggcagcccc gagaaccaca ggtgtacacc ctgcccccat cccgggagga gatgaccaag   420
aaccaggtca gcctgagttg cgcagtcaaa ggcttctatc ccagcgacat cgccgtggag   480
tgggagagca atgggcagcc ggagaacaac tacaagacca cgcctcccgt gctggactcc   540
gacggctcct tcttcctcgt cagcaagctc accgtggaca agagcaggtg gcagcagggg   600
aacgtcttct catgctccgt gatgcatgag gctctgcaca accgctacac gcagaagagc   660
ctctccctgt ctccgggtaa a                                            681

<210> SEQ ID NO 48
<211> LENGTH: 508
<212> TYPE: PRT
<213> ORGANISM: Artificial Sequence
<220> FEATURE:
<223> OTHER INFORMATION: First Polypeptide Chain of DART-2 w/Fc Version 2 Construct

<400> SEQUENCE: 48

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Ala Pro Ser Ser Pro Met Glu Asp Ile Gln Leu Thr
225                 230                 235                 240

Gln Ser Pro Ser Phe Leu Ser Ala Ser Val Gly Asp Arg Val Thr Ile
                245                 250                 255

Thr Cys Ser Ala Arg Ser Ser Ile Ser Phe Met Tyr Trp Tyr Gln Gln
            260                 265                 270

Lys Pro Gly Lys Ala Pro Lys Leu Leu Ile Tyr Asp Thr Ser Asn Leu
        275                 280                 285

Ala Ser Gly Val Pro Ser Arg Phe Ser Gly Ser Gly Ser Gly Thr Glu
    290                 295                 300

Phe Thr Leu Thr Ile Ser Ser Leu Glu Ala Glu Asp Ala Ala Thr Tyr
305                 310                 315                 320

Tyr Cys Gln Gln Trp Ser Ser Tyr Pro Leu Thr Phe Gly Gln Gly Thr
                325                 330                 335

Lys Leu Glu Ile Lys Gly Gly Ser Gly Gly Gly Gly Glu Val Gln
            340                 345                 350

Leu Val Glu Ser Gly Gly Gly Leu Val Gln Pro Gly Gly Ser Leu Arg
        355                 360                 365
```

```
Leu Ser Cys Ala Ala Ser Gly Phe Thr Phe Ser Thr Tyr Ala Met Asn
    370                 375                 380

Trp Val Arg Gln Ala Pro Gly Lys Gly Leu Glu Trp Val Gly Arg Ile
385                 390                 395                 400

Arg Ser Lys Tyr Asn Asn Tyr Ala Thr Tyr Tyr Ala Asp Ser Val Lys
                405                 410                 415

Asp Arg Phe Thr Ile Ser Arg Asp Asp Ser Lys Asn Ser Leu Tyr Leu
                420                 425                 430

Gln Met Asn Ser Leu Lys Thr Glu Asp Thr Ala Val Tyr Tyr Cys Val
                435                 440                 445

Arg His Gly Asn Phe Gly Asn Ser Tyr Val Ser Trp Phe Ala Tyr Trp
450                 455                 460

Gly Gln Gly Thr Leu Val Thr Val Ser Ser Gly Gly Cys Gly Gly Gly
465                 470                 475                 480

Lys Val Ala Ala Leu Lys Glu Lys Val Ala Ala Leu Lys Glu Lys Val
                485                 490                 495

Ala Ala Leu Lys Glu Lys Val Ala Ala Leu Lys Glu
                500                 505

<210> SEQ ID NO 49
<211> LENGTH: 198
<212> TYPE: PRT
<213> ORGANISM: Macaca fascicularis
<220> FEATURE:
<221> NAME/KEY: MISC_FEATURE
<222> LOCATION: (1)..(198)
<223> OTHER INFORMATION: V35 allele (FN18+) of CD3 epsilon

<400> SEQUENCE: 49

Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
                20                  25                  30

Gln Thr Pro Tyr Gln Val Ser Ile Ser Gly Thr Thr Val Ile Leu Thr
                35                  40                  45

Cys Ser Gln His Leu Gly Ser Glu Ala Gln Trp Gln His Asn Gly Lys
50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
                100                 105                 110

Cys Met Glu Met Asp Val Met Ala Val Ala Thr Ile Val Ile Val Asp
                115                 120                 125

Ile Cys Ile Thr Leu Gly Leu Leu Leu Val Tyr Tyr Trp Ser Lys
130                 135                 140

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Val Pro Asn
                165                 170                 175

Pro Asp Tyr Glu Pro Ile Arg Lys Gly Gln Gln Asp Leu Tyr Ser Gly
                180                 185                 190

Leu Asn Gln Arg Arg Ile
                195
```

<210> SEQ ID NO 50
<211> LENGTH: 171
<212> TYPE: PRT
<213> ORGANISM: Macaca fascicularis
<220> FEATURE:
<221> NAME/KEY: MISC_FEATURE
<222> LOCATION: (1)..(171)
<223> OTHER INFORMATION: CD3 delta

<400> SEQUENCE: 50

Met Glu His Ser Thr Phe Leu Ser Gly Leu Val Leu Ala Thr Leu Leu
1               5                   10                  15

Ser Gln Val Ser Pro Phe Lys Ile Pro Val Glu Glu Leu Glu Asp Arg
            20                  25                  30

Val Phe Val Lys Cys Asn Thr Ser Val Thr Trp Val Glu Gly Thr Val
        35                  40                  45

Gly Thr Leu Leu Thr Asn Asn Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Ala Val Gln Val His Tyr Arg Met Cys Gln Asn Cys
                85                  90                  95

Val Glu Leu Asp Pro Ala Thr Leu Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser Arg Leu Gly Gly Asn Trp Ala Arg Asn Lys
                165                 170

<210> SEQ ID NO 51
<211> LENGTH: 207
<212> TYPE: PRT
<213> ORGANISM: Homo sapiens
<220> FEATURE:
<221> NAME/KEY: MISC_FEATURE
<222> LOCATION: (1)..(207)
<223> OTHER INFORMATION: CD3 epsilon

<400> SEQUENCE: 51

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

```
Ser Val Ala Thr Ile Val Ile Val Asp Ile Cys Ile Thr Gly Gly Leu
        130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
                180                 185                 190

Lys Gly Gln Arg Asp Leu Tyr Ser Gly Leu Asn Gln Arg Arg Ile
                195                 200                 205

<210> SEQ ID NO 52
<211> LENGTH: 150
<212> TYPE: PRT
<213> ORGANISM: Homo sapiens
<220> FEATURE:
<221> NAME/KEY: MISC_FEATURE
<222> LOCATION: (1)..(150)
<223> OTHER INFORMATION: CD3 delta

<400> SEQUENCE: 52

Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
            20                  25                  30

Asp Ile Thr Arg Leu Asp Leu Gly Lys Arg Ile Leu Asp Pro Arg Gly
        35                  40                  45

Ile Tyr Arg Cys Asn Gly Thr Asp Ile Tyr Lys Asp Lys Glu Ser Thr
    50                  55                  60

Val Gln Val His Tyr Arg Met Cys Gln Ser Cys Val Glu Leu Asp Pro
65                  70                  75                  80

Ala Thr Val Ala Gly Ile Ile Val Thr Asp Val Ile Ala Thr Leu Leu
                85                  90                  95

Leu Ala Leu Gly Val Phe Cys Phe Ala Gly His Glu Thr Gly Arg Leu
            100                 105                 110

Ser Gly Ala Ala Asp Thr Gln Ala Leu Leu Arg Asn Asp Gln Val Tyr
        115                 120                 125

Gln Pro Leu Arg Asp Arg Asp Asp Ala Gln Tyr Ser His Leu Gly Gly
    130                 135                 140

Asn Trp Ala Arg Asn Lys
145                 150

<210> SEQ ID NO 53
<211> LENGTH: 6
<212> TYPE: PRT
<213> ORGANISM: Artificial Sequence
<220> FEATURE:
<223> OTHER INFORMATION: 6His Peptide

<400> SEQUENCE: 53

His His His His His His
1               5

<210> SEQ ID NO 54
<211> LENGTH: 7
<212> TYPE: PRT
<213> ORGANISM: Artificial Sequence
<220> FEATURE:
<223> OTHER INFORMATION: Heterodimerization Domain
```

```
<400> SEQUENCE: 54

Gly Val Glu Pro Lys Ser Cys
1               5

<210> SEQ ID NO 55
<211> LENGTH: 6
<212> TYPE: PRT
<213> ORGANISM: Artificial Sequence
<220> FEATURE:
<223> OTHER INFORMATION: Heterodimerization Domain

<400> SEQUENCE: 55

Val Glu Pro Lys Ser Cys
1               5

<210> SEQ ID NO 56
<211> LENGTH: 7
<212> TYPE: PRT
<213> ORGANISM: Artificial Sequence
<220> FEATURE:
<223> OTHER INFORMATION: Heterodimerization Domain

<400> SEQUENCE: 56

Gly Phe Asn Arg Gly Glu Cys
1               5

<210> SEQ ID NO 57
<211> LENGTH: 6
<212> TYPE: PRT
<213> ORGANISM: Artificial Sequence
<220> FEATURE:
<223> OTHER INFORMATION: Heterodimerization Domain

<400> SEQUENCE: 57

Phe Asn Arg Gly Glu Cys
1               5
```